United States Patent [19]

Cochran et al.

[11] Patent Number: 5,599,544
[45] Date of Patent: Feb. 4, 1997

[54] RECOMBINANT INFECTIOUS BOVINE RHINOTRACHEITIS VIRUS

[75] Inventors: Mark D. Cochran, Carlsbad; Richard D. Macdonald, San Diego, both of Calif.

[73] Assignees: PruTech Research and Development Partnership, San Jose, Calif.; Syntro Corporation, Lenexa, Kans.

[21] Appl. No.: 479,650

[22] Filed: Jun. 7, 1995

Related U.S. Application Data

[63] Continuation of Ser. No. 247,475, May 23, 1994, which is a continuation of Ser. No. 732,584, Jul. 18, 1991, abandoned, which is a continuation-in-part of Ser. No. 696,262, Apr. 30, 1991, abandoned, which is a continuation of Ser. No. 933,107, Nov. 20, 1986, abandoned, and a continuation-in-part of Ser. No. 649,380, Jan. 31, 1991, abandoned, which is a continuation of Ser. No. 78,519, Jul. 27, 1987, abandoned, and a continuation-in-part of Ser. No. 225,032, Jul. 27, 1988, Pat. No. 5,223,424, Ser. No. 823,102, Jan. 27, 1986, Pat. No. 5,068,192, and Ser. No. 192,866, May 11, 1988, Pat. No. 5,047,237.

[51] Int. Cl.$^6$ .............................. A61K 39/265; C12N 7/01
[52] U.S. Cl. ........................................... 424/229.1; 435/235.1
[58] Field of Search .......................... 435/235.1; 424/229.1

[56] References Cited

U.S. PATENT DOCUMENTS 4,992,051  2/1991  Kit et al. ............................ 435/235.1

*Primary Examiner*—Mindy Fleisher
*Assistant Examiner*—Terry A. McKelvey
*Attorney, Agent, or Firm*—John P. White

[57] ABSTRACT

The present invention provides recombinant infectious bovine rhinotracheitis (IBR) viruses useful in vaccines to protect bovines from infectious bovine rhinotracheitis and other bovine diseases. The present invention further provides methods for distinguishing an animal vaccinated with the vaccine of the present invention

FIGURE 3

SEQ. ID. NO. 1

TTAAGCGTTGCCCGTGGCGGTCGCCATGGTGACTATAGTCACGTGTGGCCGATAGGCCGG
MetValThrIle..............

GCGCCTTCCAGGCAAGCCCAGACGTGCCGCCGGGTGTGGCGTTCCTTGCCGAGCAG
AGCCGGGCGCTGACGGCAAGCGGCTGGGGACGACGGCAAGGCGGTCGTTGTCTTCACGCCCTA
GTAAAAACGGCGAAGGGCTGCACGTCGACGTCAAGCGTCAAGCCAGCGGCGGGTGGCTT
TTGTCGACACAGCGCCCTTGGCGCGCCTTAGCGCGCCTTACCGCCAACCGGCGAG
TGGGTCAGCTGGTCGACGGCTACAAACTGCTGAAACTCGGCCGCGAGGGCTCGGCCC
TTCCACATGTGGGTTTTTGCGCCGATTTGTACGCGCCCTATTTTGCGCACATTGCC
GCCACGACGCGCTTGGTTTACGCGGACTGGAGCCCGTACGTTTGCGGAGCGGCGTGGCGG
CTCCCGCGGCCGCCGGCCCATCGCTAGCCGTGGCCCTACGATACCCCGACACTC
CCTGAGCTGGTGGCCGCGTGGTGTCCTTTTCCGGTCTCTACGAAGTCGTAGACCGCGGG
CGGCGCCCCCGCCAAACGCCGAGCCCCAGGGGCGCTCGCCCCCCCGCCGCGC
CATGTGCTATCCTTTAAAGGCCCGCCGGTTTGGTTCATTTGCTTTGTGACC
GCGCCGAGGACAGAGAGGCGCACCCGTCGTCCCGGCACCCCAAACCGTGGTGATCAGCACAGTGCC
GTTGAGCAGAGAGGCGGACCGGACCCGGCCGCGCCGGATGCGAGGGGGG
GCTTGGTGGCTGGCGACTCTTTACAGTGCCGCCAAGAAGACGCCTGTATGCTA
TCGTCCCGCCGGACTATTTTCCGGTGGGTCGGCCCTCGTGCTGCTGGTGAAAGTTC
..............ProSerProCysTrp---

CCGCTCCCCGGCGAGTCCCCGACCCGAACTGGGGCCAGTTCACTTTGAATGTGTTCCCG
CGCCGCCGGGACCCGCTGCAGTTCTTTCGTCAGCTTTTACGACGGTTCATTCGTTAAGCTT

| | | |
|---|---|---|
| SEQ. ID. NO. 2 IBR US2 | 115 | H-MWVFGAADLYAPIFAHI |
| SEQ. ID. NO. 3 HSV-1 US2 | 124 | H-LWVVGAADLCVPFLEYA |
| SEQ. ID. NO. 4 PRV US2 | 148 | H-LWILGAADLCDQVLLAA |
| SEQ. ID. NO. 5 HSV-2 US2 | 123 | H-LWVVGAADLCVPFFEYA |
| SEQ. ID. NO. 6 MDV US2 | 132 | HSLWIVGAADICRIALECI |

FIGURE 5B

```
SEQ. ID. NO. 7   IBR Cooper    HindIII O   TGAGGCGCGCCGCTGCATGCTGGTGCGAACTCACGCCGAGCCGGTGCGAGCAAGCTT
                                                                                                  HindIII
                                           |||||||||||||||||||||||||||||||||||||||||||||||||||||||||
SEQ. ID. NO. 8   IBR Nasalgen  HindIII K   CTAGTAAAAACGGGCGAAGGGCTGGTGCGAACTCACGCCGAGCCGGTGCGAGCAAGCTT
                                           ||||||||||||||||||||||||
SEQ. ID. NO. 9   IBR Cooper    HindIII K   CTAGTAAAAACGGGCGAAGGGCGAACGTCGACGTCAACGTCAAGCCAGCGGCGCGGGTGG L  V  K  T  A  K  G  C  T  S  T  S  S  Q  R  R  G  W
                                                                  |
                                                                US2 (58)
```

| DNA | Origin | Sites | Size |
|---|---|---|---|
| Vector | pSP65 | SmaI - HindIII | ~2975 BP |
| Fragment 1 | IBR HindIII A | NcoI - BamHI | ~ 860 BP |
| Fragment 2 | HSV-1 BamHI N | PvuII - BamHI | ~ 490 BP |
| Fragment 3 | Tn5 | BglII - BamHI | ~1541 BP |
| Fragment 4 | HSV-1 BamHI Q | SmaI - SmaI | ~ 784 BP |
| Fragment 5 | IBR HindIII A | BglII - StuI | ~1741 BP |

FIGURE 7C

SEQ. ID. NO. 13

Junction D   GGA CCT TGC ACA GAT·AGC GTG GTC CGG CCA·GGA CGA CGA GGC
             　　　　　　　　　　  BamHI            [SmaI]
             TTG·CAG GAT CCT CTA GAG·TCG GGA GAT GGG GGA·GGC TAA CTG AAA CAC·GGA AGG AGA
                     　　　　　　　　　　　　　 Gly Asp Gly Gly·Gly Gly
                     |————> Tn5             |————> TK (350)
                                            |————> HSV-1 BamHI Q

SEQ. ID. NO. 14

Junction E   GTG TTG CTG CGT TCC·CGA CCT GCA GCC CAA·GCT CTA GAG TCG
                                      PstI            XbaI  SalI
             |————> HSV-1 BamHI Q                [SmaI]

BglII
             ACC·TGC AGC CCA AGC TCA·GAT CTG CTC ATG CTC·GCG GCC ATG CCC·CCG GAA GCG
               PstI                                        Ala MET Leu Ala Ala·MET Pro Pro Glu Ala
                                         Asp Leu Leu MET
                                              |————> TK (156)
                                              |————> HindIII A

SEQ. ID. NO. 15

Junction F   AGG CAG ATC TGA GCT·TGG CGT AAT CAT GGT·CAT AGC TGT TTC CTG·TGT GAA ATT GTT ATC·
             [StuI] BglII [HindIII]
             |————> pSP65

|————> HindIII A

FIGURE 8

SEQ. ID. NO. 16

GCGATCATGCCTGCCGCCCGGACCGGCACCTTGGCCGCCGTCGCCCTAATCCTGCTCTGC
MetProAlaAlaArg..........

GGGGCCGCCGTTTGCGGCCCCGCGCCCGACGACCTCTGTTTCGCCGACGTGCCGCCGCAC
TGGCATGGCGCCCTCCCCGCCCGCTGGGGCCCGTCCTGAACCTAGCGCCTCGGATTTGAC
CTCGCGGGTTTCGTGCGCGGTGCCCGGAGCTTCGCGCTGCCCTGGCCCTCTTGGACA
TGGCGGAGACGGTGGTGCCCGGACCGGCGAGCCSCACGTCGTCGACGTCGGCTGGGCT
TACCAAGACGGGACTGCATGGTGCCTCTGCATATCGCCAGTACTTTAACTGCACGGGG
GGCGCGCTGCCCGCGCCAAAACGTCTGCGCCGGGACGTCTCTGAGACCCGCATCCGCGGTGGC
TTTGAACCTCCGACTACGCGCTCTACTTCCTTGGATACGCCCAGACGTACTGCGCCCGGCCTGTAC
GACCGGGACCTACATCTACTTCCTTGGATACGCCCCAGACGACATCTACGTGGGCAGC
GTCACGCTCATGGTGGGCGCCGACATCCACAAATACCCCTGCGGCTGGACCGAGGGCTC
GGTGTGCCCTGCACCACAAGAGCGGACGCCGACCTCTGACAGAGGACGACGCCACC
GGCGACTGGGCCTGCGGCTGCTTCCCCGCCCTGTTGAGGTTGACGCGGTGTGGGCAAC
GTAAGCGCCAGAGCTGGGGCCTGGCCTGGGAGCCCGACCTACGCCGACGAAGGGGTGAG
GTCGAAGTGCTCGAGGACGAAGCCGGGACACCCGGAGCGCCAGCGAAACCTGCCGACGACCCC
GACCCCGACCTCGCAGATTGCCGGACCTCGGGCTCTTTAGCGAAAGCGACATGTTCCGG
ACCGCCACGGCCCGAATCGCTGCTGCTCTTACGAGCCCTTGCCAAGGACGCTGGAGTGC
CCCTCAATCTGCCCCGCCGCTCTTACGAGCCCTGCGAAACGCATGCTGGAGTGC
AACTCCCGCGAGCCGCGAGACCGGCGAGCCCAGCGGTGGTGATGTCTCTCCAGGAGCCC
GCTGCCTCGAGATGACCCCGTGCCCGCGGCATTCTACCTCCGATCGCTCTTTGGC
CTGCCCGATGACCCGTGCCGCGGCATTCTATCGGCCTCCGATCGCTCTGCTGG
TGCTGCTGTGTTCGCTGTGATCGTCGTCGCCCTGCCTCGCCGCTCGCCGCCCCAGCCAA
GGCTGCGGACGCCCCGCGCACGTTCGCCAAGAGCAACCCGCGTACGAGCCGATG
CTCAGCGTCTGATCGCCGGACACCCCGCTGTCCCGCGTTTACAAT
...SerVal---

AAACAG

IBR gpG (4412)

PRV gpG (498)

```
SEQ. ID. NO. 17
    IBR gpG    95   VGWAYQDGDCMVPLAYRQYFNCTGGALPGNVLCA
                    | |   | | ||  | |  | | | |        |
SEQ. ID. NO. 18
    PRV gpX    89   VAWFFDGGHCKVPLVHREYYGCPGDAMPSVETCT
                         | |   | | ||| |   ||   ||
SEQ. ID. NO. 19
    HSV-2 gpG  111  VTYYRLTRACRQPILLRQYGGCRGGEPPSPKTCG
                    |     | |   | |  ||  ||   |     |
                    V         C P   R Y  C G   P     C
```

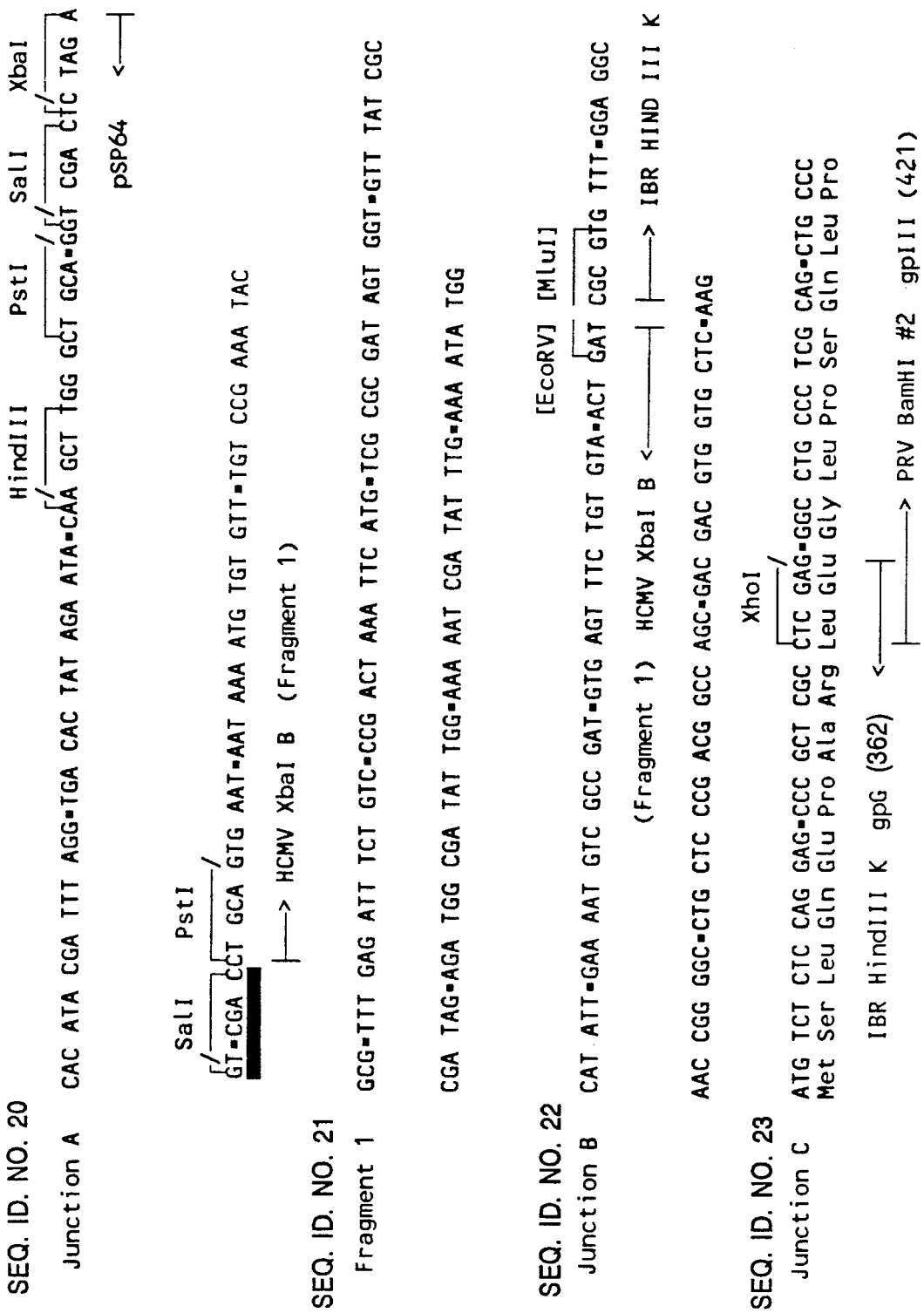

FIGURE 11C

```
GTC TTC GAG-GAC ACG CAG CGC TAC-GAC GCC TCC CCC GCG-TCC GTG AGC TGG
Val Phe Glu Asp Thr Gln Arg Tyr Asp Ala Ser Pro Ala Ser Val Ser Trp (Fragment 3)
                                                              BamHI
SEQ. ID. NO. 24                                                 ⌐
Junction D   CCC-GTG AGC AGC ATG ATC-GTC GTC ATC GCC GGC-ATC GGG ATC CTG GCC-ATC
             Pro Val Ser Ser MET Ile Val Val Ile Ala Gly Ile Gly Ile Leu Ala Ile (Fragment 3)              PRV BamHI #2  ←

NdeI
             GTG CTG GTC ATC-CAT ATG GCG ATC ATC-AGG GCC CGG GCC CGG AAC GAC GGC
             Val Leu Val Ile His MET Ala Ile Ile Arg Ala Arg Ala Arg Asn Asp Gly gpIII (467) ←     ────→ gpX (480)
                           ────→ PRV BamHI #7
                                        SalI    XbaI   SalI       PstI
SEQ. ID. NO. 25                           ⌐       ⌐     ⌐           ⌐
Junction E   GGG CCA GTA CCG GCG-CCT GGT GTC CGT CGA-CTC TAG AGT CGA CCT-GCA GCC PRV BamHI #7      ──────→ pSP65

HindIII
                ⌐
             CAA GCT TTG GCG TAA TCA TGG TCA
```

FIGURE 12A

| FIGURE 12A |
|------------|
| FIGURE 12B |
| FIGURE 12C |
| FIGURE 12D |

| DNA | Origin | Sites | Size |
|---|---|---|---|
| Vector | pSP64 | HindIII - SmaI | ~2965 BP |
| Fragment 1 | IBR HindIII K | HindIII - XhoI | ~3593 BP |
| Fragment 2 | PRV BamHI #7 | SalI - NdeI* | ~ 753 BP |
| Fragment 3 | pJF751 | BalI - BamHI | ~3347 BP |
| Fragment 4 | HCMV XbaI B | AvaII - PstI | ~1191 BP |
| Fragment 5 | IBR HindIII K | XhoI - NdeI | ~ 785 BP |

* resected with ExoIII/S1

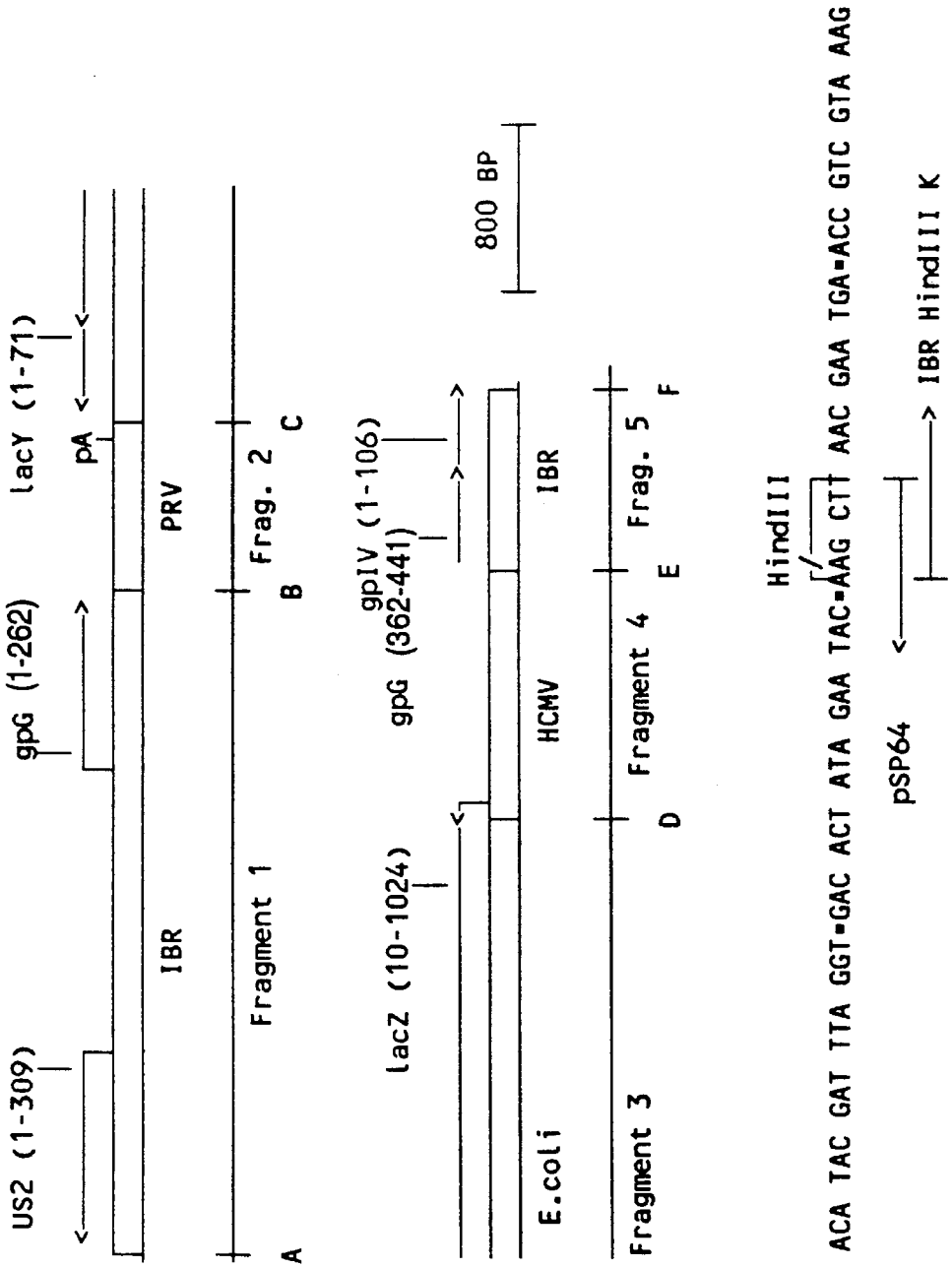

| DNA | Origin | Sites | Size |
|---|---|---|---|
| Vector | pSP64 | HindIII - SmaI | ~2965 BP |
| Fragment 1 | IBR HindIII K | MluI - SmaI | ~888 BP |
| Fragment 2 | PRV BamHI #7 | SalI - NdeI* | ~753 BP |
| Fragment 3 | pJF751 | BalI - BamHI | ~3347 BP |
| Fragment 4 | HCMV XbaI B | AvaII - PstI | ~1191 BP |
| Fragment 5 | IBR HindIII K | XhoI - NdeI | ~785 BP |

* resected with ExoIII/S1

SEQ. ID. NO. 33

Junction A  ATA CAC ATA CGA TTT-AGG TGA CAC TAT AGA-ATA CAA GCT CGC GTG-TTT GGA GGC AAC

FIGURE 13C

SEQ. ID. NO. 30

Junction D    TCC CAG TCA CGA CGT·TGT AAA ACG ACG GGA·TCC ATG GTC CCG GTG·TCT TCT ATG GAG BamHI   NcoI   AvaII lacZ (10) <─┘
pJF751 <─
Met <─┘
─> HCMV IE promoter
─> HCMV XbaI B

SEQ. ID. NO. 31

Junction E    ATT CAC TGC AGG TCG·ACT CTA GAG GAT CCC·CGG GCG AGC TCG AAT·TCG AGC CGC CGC
                           PstI   SalI   XbaI   BamHI       SacI   [EcoRI] [XhoI]         Glu Arg Arg HCMV IE promoter <─┘
HCMV XbaI B <─
├─> gpG (362)
├─> IBR HindIII K

SEQ. ID. NO. 32

Junction F    GCG CGC GCG TAC AAC·GCC ACG GTC ATA GGG·CGA GCT CGA ATT CGT·AAT CAT GGT CAT
            Ala Arg Ala Tyr Asn Ala Thr Val Ile     [NdeI] [SmaI]   SacI     EcoRI gpIV (106) <─┘
IBR HindIII K <─
───────> pSP64

SEQ. ID. NO. 33

Junction A    ATA CAC ATA CGA TTT•AGG TGA CAC TAT AGA•ATA CAA GCT CGC GTG•TTT GGA GGC AAC

FIGURE 14B

SEQ. ID. NO. 35

Junction B

```
                    [SmaI][EcoRI]  SacI              BamHI        XbaI      BamHI              SacI
                         /           /                  /           /         /                  /
     CGG GGT AGC  CCC AAT▪TCG  AGC TCG CCC GGG▪GAT CCT CTA GAG GAT▪CCC CGG GCG AGC
  IBR HindIII K <──┘
```

```
       [EcoRI] [XhoI]
          /     /
     TCG▪AAT TTC GAG CGC CGC▪CCC GAT GCC
             Glu Arg Arg Pro Asp Ala
     ├─────────> gpG (362)
     ├─────────> IBR HindIII K
```

SEQ. ID. NO. 32

Junction C

```
                                         [NdeI][SmaI]  SacI           EcoRI
                                              /  /       /              /
     GCG CGC GCG TAC AAC▪GCC ACG GTC ATA GGG▪CGA GCT CGA ATT CGT▪AAT CAT GGT CAT
     Ala Arg Ala Tyr Asn Ala Thr Val Ile
                         ├─────> gpIV (106) <┐
                         IBR HindIII K <─────┤
                                             ├─────> pSP64
```

FIGURE 15A

| FIGURE 15A |
|---|
| FIGURE 15B |

SEQ. ID. NO. 36

GCGGGCAAGGCGAGGAAGACCGGGGCAGGAGCTGCGTGGAGGGCGAGCCGTTGAGCG
GCCCGACCGCCCGGGTTGTTAAATGGGTCTCGCGGCTCGTGGTTCCACACCGCGCC
MetGlyLeuAlaArg...........

GGAGAACCAGCCGCGCCAGCTTCGCTGCCTGTGTCCCGGAGCTGCGTTCCGGGAACGGCG
CGCGCGAGAGGGTTCGAAAAGGGCATTTGGCAATGCAACCCACCGCGCCCCGGCSSG
GTTGCCGCCGCTGCTGCTGCCGCAGTTATTGCTTTTCGGGCTGATGGCTGAGGCCAAGCCC
GCGACCGAAACCCCGGGCTCGGCTTCGGTCGACACGGTCTCTTCACGGCGCGCTGGCGCG
CCCGTCTTTCTCCCAGGCCCCGCCTGCTCGCCGCCCGTGCCGCGCCCGTTCGCGGCTGGAGC
GTCCTCGCGGGCCCTGCTCGCCCTCGACACGCGTGCCCCTGCCGGAGCCCGTCTGCGACACCGCGAG
TGCTTCACCGACGTGGCCCGAGCTCGCGGACGCGCCCGACTCAACGGCGACAAAGAGTTTGTTCTCGCC
GCCATCGCGGAGCTCGCGGCAGCTCGCGCGCCCTGGGTCGCAACGGGCGACAAAGAGTTTGTTCTCGCC
GACCCGCCACGTCTCGCGGCAGCTCGTGTACTTCCTGTACGACCCGGCTCATCGGCGACGCCGGCGCA
GCCGAGGAGGACGCGCAGTTGGCGGCGGTGTACTTCCTGTACGACCGGCTCATCGGCGACGCCGGCGAC
GAGGAGAGACGACGAGTTGGCGGCGGTGTACCAGCGGCGAACGGGCGACACCGGCCCGCAGGGGCCGCCGCG
CGGGACGAGGAGGAGGGAACCAGCGAACCAGCGGCACGCGGCCCCCCACCCCCCGCGCTTCCCGCGTCTGCCGCCACCGCACG
ACGACACGCGCACCCCCGGGCGATTCCTTTCTGCTATCGGTCGTCTGCAGTCTGAGTTTTTC
CACGTATACACCCCCGGGCGATTCCTTTCTGCTATCGGTCGTCTGCAGTCTGAGTTTTTC
GACGAGGCTCCCTTCTCGCCAGCATCGACTCTTCCACCCGAGCCCTGCCTGCCTGCACGACCGGACTGC
GCGCTCATCCGACATACGAGACGCTTCGCATCTTCCACCCCGAGCACCGGCCTGCCTGCAC
CCCGCCACGCGCAGTGCCGCCCGAGACCCTCGGTCGCGGTCGCGTCCCGGCTCGACCGTGTACAGCCGG
CTGTACGAGCAGTGCCCGCCCCGAGACCCTCGGTCGCGGTCGCGTCCCGACGAGTGCCGAGGCGCC
GCGTACGACGCGCGGCGCCGGCCCTGCGCAATAACAGCGTAGACCTGGTCTTT
GACGACGCGCGGCCGGCCCTCCGGGCTTTACGTCTCTTTGCTGTCGCAGTACAACGGCCAC

FIGURE 15B

```
GTGGAAGCTTGGGACTACTGCCCTAGTCGTTACTTCGGACCCGTTTGGTGCGCGGCGTCACC
GACCACACGCGCCGCCCCCGAGGCCCGCAGCCCGACGCGCTCCCGAGCCAGGCCCACCGCTCACC
AGCGAGCCGCGGGGSGCCCACCGGGCGCCGCCCCTGGCTTGTGTGGTGCTTGGTGGCGCG
CTTGGACTCGCGGGACTGGTGGGCATCGCAGCCCTCGCGTTCGGTGTGCGCGCCCGC
GCAAGCCAGAGAAGCGCACCTACGACCATCCTCAACCCCTTCGGCCCGTATACCAGCTTG
CCGACCAACGAGCCGCTCGACGTGGTGTGCCAGTTAGCGACGACGAATTTTCCCTCGAC
GAAGACTCTTTTGCGGATGACGACAGCAGCCCCAGAGACGACCAACTAGCGGGTTTGCGCGAGCCCTGCG
GATGCCTACGACCCTCGCGCTCGAGTCGCTTCTGGGTTTCAAAGTTTGGTTTAGGACCCGCTTGAAGAC
AACGGCACGCGCTCGAGTCGCTTCTGGGTTTCAAAGTTTGGTTTAGGACCCGCTTGAAGAC
GATGCCCGCGCCAGCGCGGACCCCGCGCCACCAGATTACACCGTGGTAGCAGCGCGACTC
AAGTCCATCCTCCCGCTAGCGCCCCCCGGCCTGTGCCCGTCTGACGGAAAAGCACCC
......IleLeuArg---

GCGTGTAGGGCTGCATATAAATGGAGCGCTCACACAAAGCCTCGTGCGGCTGCTTCGAAG
```

FIGURE 16B

```
SEQ. ID. NO. 37
HSV-1 gpE    262  WLRFDVPTSCAEMRIYESCLYHPQLPECLSPADAPC--AASTWTSRLAVRSY
                  |   |   |    |  |    |||||     |
SEQ. ID. NO. 38
PRV gI       265  WYYARAPPRCLLYYVYEPCIYHPRAPECLRPVDPACSFTSPARAALVARRAY
                  |   |   |    |  |    |||||     |
SEQ. ID. NO. 39
VZV gpI      378  WLYVPIDPTCQPMRLYSTCLYHPNAPQCLSHMNSGCTFTSPHLAQRVASTVY
                  |   |   |    |  |    |||||     |
SEQ. ID. NO. 40
IBR gpE      303  WYFLRTAGDCALIRIYETCIFHPEAPACLHPADAQCSFASPYRSETVYSRLY
                  W   C   Y   C   HP  P CL    C                    Y
```

FIGURE 17B

SEQ. ID. NO. 42

Junction B

```
                                                               HindIII
                                                                 /
         TCC GGG CTT TAC GTC-TTT GTG CTG CAG TAC-AAC GGC CAC GTG CTG-GCT TGG GAC
         Ser Gly Leu Tyr Val Phe Val Leu Gln Tyr Asn Gly His Val Glu Ala Trp Asp
```

———> IBR SmaI 2.5 KB

IBR HindIII K <———

```
         TAC AGC-CTA GTC GTT ACT TCG-GAC CGT TTG
         Tyr Ser Leu Val Val Thr Ser Asp Arg Leu
```

SEQ. ID. NO. 43

Junction C

```
                                                                              SacI
                                                                               /
         CCT TCA CCG CCG-GAA GGC TCC ATC GTG-TCC ATC CCC ATC CTC-GAG CTC GAA
```

———> pSP65

IBR SmaI 2.5 KB <———

```
         [SmaI] BamHI  XbaI   SalI  PstI
            /     /     /      /     /
         TTG GGG-ATC CTC TAG AGT CGA-CCT GCA GCC
```

FIGURE 18A

| FIGURE 18A |
|---|
| FIGURE 18B |
| FIGURE 18C |
| FIGURE 18D |
| FIGURE 18E |

| DNA | Origin | Sites | Size |
|---|---|---|---|
| Vector | pSP65 | SmaI - HindIII | ~2975 BP |
| Fragment 1 | IBR HindIII K | SmaI - SmaI | ~1704 BP |
| Fragment 2 | PRV BamHI #10 | SalI - BamHI | ~413 BP |
| Fragment 3 | pJF751 | BamHI - PvuII | ~3010 BP |
| Fragment 4 | PRV BamHI #7 | NdeI - SalI | ~754 BP |
| Fragment 5 | IBR SmaI 2.5KB | NheI - BglI | ~742 BP |

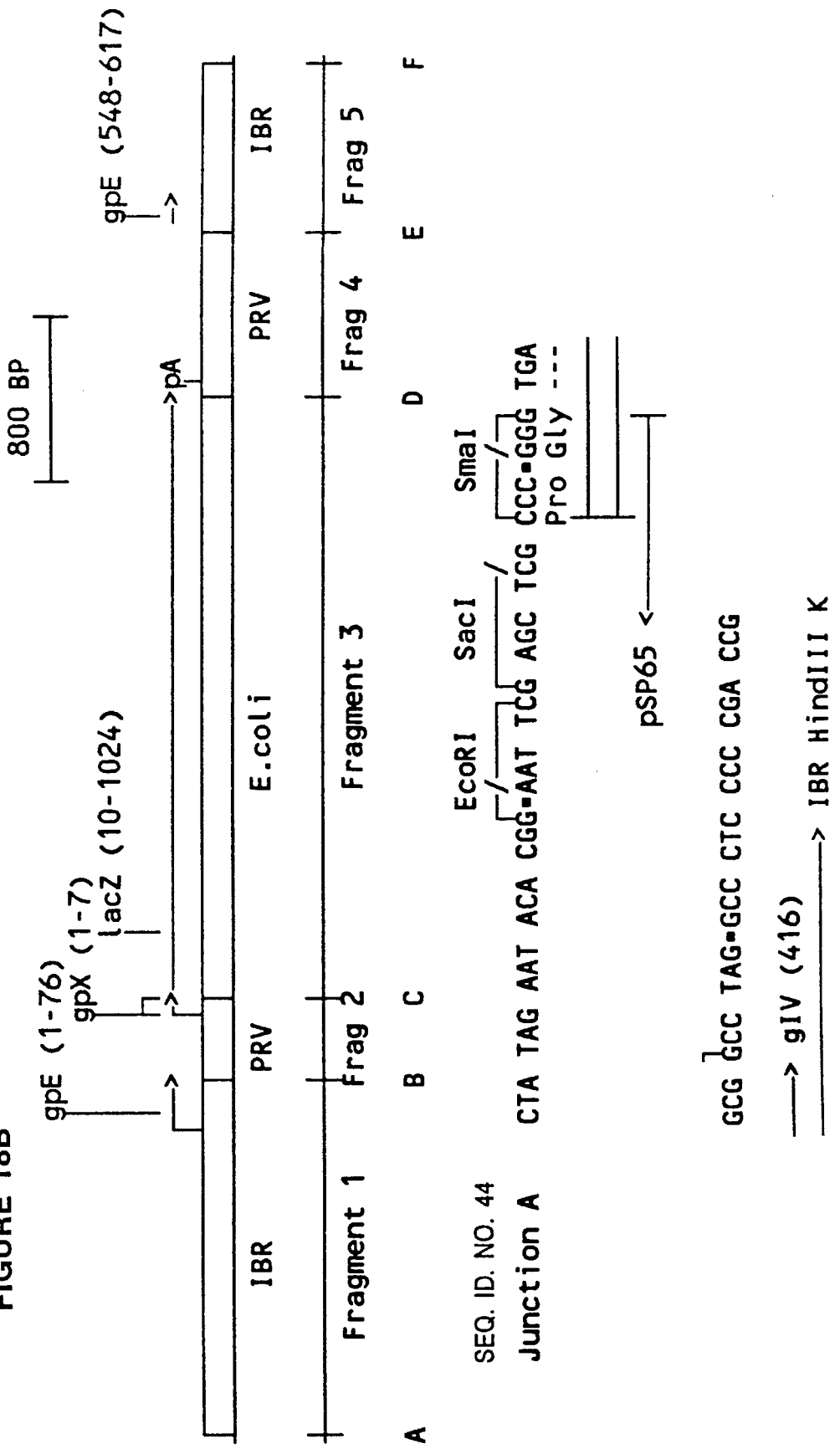

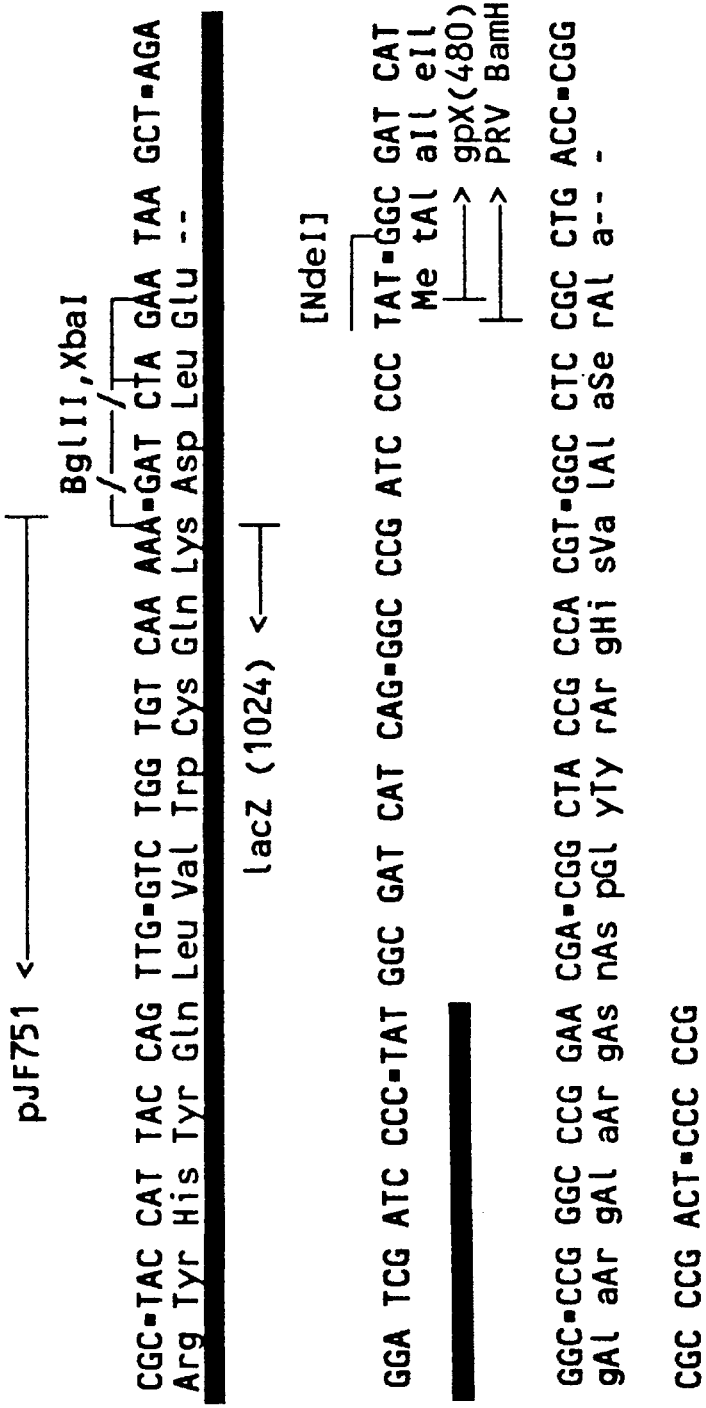

FIGURE 21A

| FIGURE 21A |
|---|
| FIGURE 21B |

SEQ. ID. NO. 49

```
AGGAACAAAGTTGTTCAACACAGCAGCAGCGAACAGACCCAAAGGCAGCAGGCGCAGAGGCGACACCGAACCCA
AATGGAATATTGAAACACACAACAGCACACAAAAACCAACAATGAAACCGAAACAACCAGAGGCAA
          METGluTyrTrpLys.............

ACACAGTAGCAAGGTTACAAATATCATAATGTACACCCTTCTGGACAATAACATCAACAATATTATTAGTC
ATTTTATAATGATATATTGACAAACTTAATTCAAGAGAATCATATAATAATTAATGTTGCAGGAAATAA
GAAAGAATTCGCGGCAATAGACACCAAGATTCAGAGGACCTCGGATGACATTGGAACCTCAATACAGTC
AGGAATAAATACAAGACTTCTCACAATTCAGAGTCATGTTCAAAACTATATCCCACTATCACTAACACAA
CAAATGTCAGATCTCAGAAATTTATCAATGATCTAACAAATAAAGAGAACATCAAGAAGTGCCAATAC
AGAGAATGACTCATGATAGAGGTATAGAACCCCTAAATCCAGACAAGTTCTGGAGGTGTACATCTGGTAA
CCCATCTCTAACAAGTAGTCGTTAGAATCCCATCGTTAGCAATCAATCCAGGGCCAGTTTATTAGCAACACCTCTAATCTTA
GTAAATGGCTGTATTAGAATCCCATCGTTAGCAATCAATCCAAATAGGATAATTACTATAAATTC
TCACCCAGGGCTGTCAAATATTAAATCCCAGAGTCACATATTAATATTGATGATAATAGGAAATCTTGC
GACCTAGTACCTGATTTAAATCCCAGAGTCACACATATTAATATTGATGATAATAGGAAATCTTGC
TCTCTGGCACTATTGAATACAGATGTTTATCAGTTATGCTCAACACCAAAAGTTGATGAGAGATCCGATT
ATGCATCAACAGTATTGAGGATATTGTACTTGACATTGTCACTAATAATGATTAATTATAACAACAAG
```

FIGURE 21B

```
GTTTACAAATAATAATATAACTTTTGATAAACCGTATGCAGCATTGTATCCATCAGTAGGACCAGGAATC
TATTATAAGGGTAAAGTTATCTTTCTCGGATATGGAGGTCTAGAGCATGAGAGAAAACGGAGACGTAATAT
GTAATACAACTGGTTGTCCTGGCAAAACACAGAGACTGTAATCAGGCTTCTTATAGCCCATGGTTCTC
AATAGGAGAATGGTAAACTCTATTATTGTTGTTGATAAAGGCATAGATGCAACTTTTAGCTTGAGGGTG
TGGACTATTCCAATGAGCCAAAATTATTGGGATCAGAAGAAGATTACTTTTATTAGGTGACAGAATAT
ACATATATACTAGATCCACACAAGTTGGCACAGTAAATTACAGTTAGGGTAATTGATATTCTGATTATAA
TAATATAAGAATAATAATTGGACTTGGCATAATAGGAGTTTACACTGACTGAAATGATGAATGTCCATGGGT
CATTCATGCCCAGACGGATGTATAACAGGAGTTTACACTGATGCATATCCGCTAAACCCATCGGGAGTG
TTGTATCATCAGTAATTCTTGACTCACAAAAGTCTAGAGAAAACATTCATTACCTACTCAACAGCTAC
AAATAGAATAAATGAATTAGCTATATATAACAGAACACTTCCAGCTGCATATACAACAACAATTGTATC
ACACATTATGATAAAGGTATTGTTTTCATATAGTAGAAATAAATCACAGAAGTTTGAATACGTTTCAAC
CTATGTTATTCAAAACAGAAGTTCCAAAAAACTGCAGCTAAANTGATCATCGCATATCGGATGCCAGATG

......ProLysAsnCysSer----

ACATTAAAGAGAGACCACCAGACAACACAGGAGATGATGCAAGATATAAAGGAATAAT
```

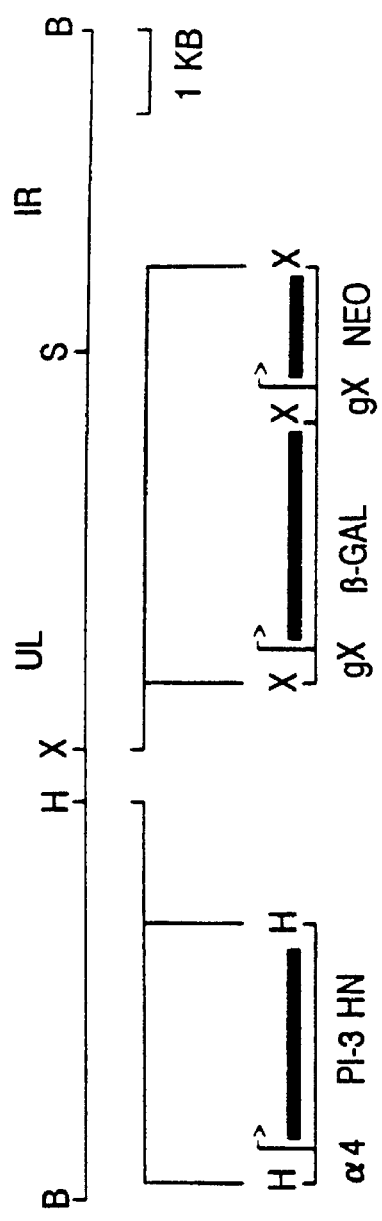
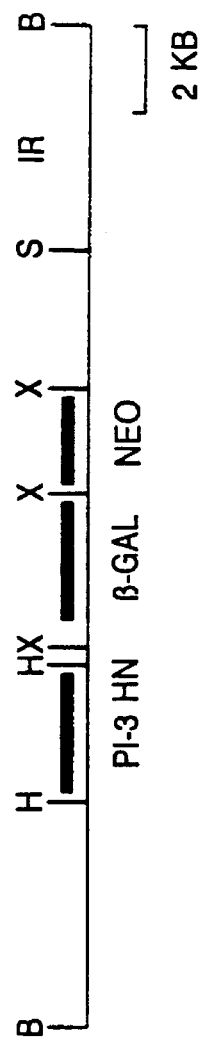
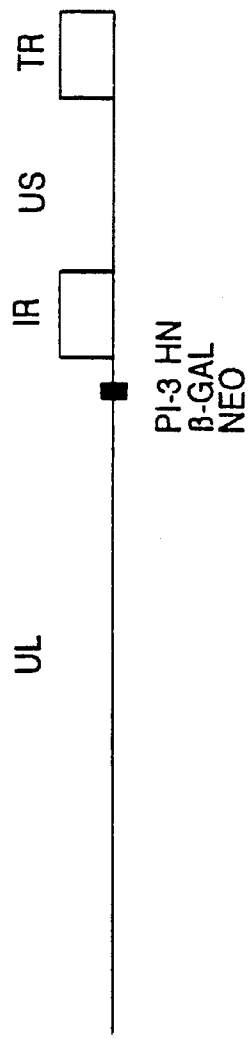
FIGURE 22A
FIGURE 22B
FIGURE 22C

RECOMBINANT INFECTIOUS BOVINE RHINOTRACHEITIS VIRUS

This application is a continuation of U.S. Ser. No. 08/247,475, filed May 23, 1994 which is a continuation of U.S. Ser. No. 07/732,584, filed Jul. 18, 1991, now abandoned; which is a continuation-in-part of U.S. Ser. No. 07/696,262, filed Apr. 30, 1991, now abandoned; which is a continuation of U.S. Ser. No. 06/933,107, filed Nov. 20, 1986, now abandoned, and a continuation-in-part of U.S. Ser. No. 07/649,380, filed Jan. 31, 1991, now abandoned which is a continuation of U.S. Ser. No. 07/078,519, filed Jul. 27, 1987, now abandoned, and a continuation-in-part of U.S. Ser. No. 07/225,032, filed Jul. 27, 1988, now U.S. Pat. No. 5,223,424, issued Jun. 29, 1993, and a continuation-in-part of U.S. Ser. No. 06/823,102, filed Jan. 27, 1986, now U.S. Pat. No. 5,068,192, issued Nov. 26, 1991, and a continuation-in-part of U.S. Ser. No. 07/192,866, filed May 11, 1988, now U.S. Pat. No. 5.047,237, issued Sep. 10, 1991, the contents of which are hereby incorported by reference.

Within this application several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

FIELD OF THE INVENTION

The present invention involves recombinant infectious bovine rhinotracheitis (IBR) viruses useful in vaccines to protect bovines from naturally-occurring infectious bovine rhinotracheitis virus and other bovine diseases.

BACKGROUND OF THE INVENTION

The ability to isolate viral DNA and clone this isolated DNA into bacterial plasmids has greatly expanded the approaches available to make viral vaccines. The methods used to make the present invention involve modifying cloned viral DNA sequences by insertions, deletions and single or multiple base changes. The modified DNA is then reinserted into the viral genome to render the virus non-pathogenic. The resulting live virus may then be used in a vaccine to elicit an immune response in a host animal and to protect the animal against a disease.

One group of animal viruses, the herpesviruses or Herpetoviridae, is an example of a class of viruses amenable to this approach. These viruses contain 100,000 to 200,000 base pairs of DNA as their genetic material. Importantly, several regions of the genome have been identified that are non-essential for the replication of virus in vitro in cell culture. Modifications in these regions of the DNA may lower the pathogenicity of the virus, i.e., attenuate the virus. For example, inactivation of the thymidine kinase gene renders human herpes simplex virus non-pathogenic (28), and pseudorabies virus of swine non-pathogenic (29).

Removal of part of the repeat region renders human herpes simplex virus non-pathogenic (30,31). A repeat region has been identified in Marek's disease virus that is associated with viral oncogenicity (32). A region in herpesvirus saimiri has similarly been correlated with oncogenicity (33). Removal of part of the repeat region renders pseudorabies virus non-pathogenic (U.S. Pat. No. 4,877,737, issued Oct. 31, 1989). A region in pseudorabies virus has been shown to be deleted in naturally-occurring vaccine strains (11,3) and it has been shown that these deletions are at least partly responsible for the lack of pathogenicity of these strains.

It is generally agreed that herpesviruses contain non-essential regions of DNA in various parts of the genome, and that modifications of these regions can attenuate the virus, leading to a non-pathogenic strain from which a vaccine may be derived. The degree of attenuation of the virus is important to the utility of the virus as a vaccine. Deletions which cause too much attenuation of the virus will result in a vaccine that fails to elicit an adequate immune response. Although several examples of attenuating deletions are known, the appropriate combination of deletions is not readily apparent.

Infectious bovine rhinotracheitis (IBR) virus, an alphaherpesvirus with a class D genome, is an important pathogen of cattle. It has been associated with respiratory, ocular, reproductive, central nervous system, enteric, neonatal, and dermal diseases (34). Cattle are the normal hosts of IBR virus, however it also infects goats, swine, water buffalo, wildebeest, mink, and ferrets. Experimental infections have been established in muledeer, goats, swine, ferrets, and rabbits (35).

Conventional modified live virus vaccines have been widely used to control diseases caused by IBR virus. However, these vaccine viruses may revert to virulence. More recently, killed virus IBR vaccines have been used, but their efficacy appears to be marginal.

IBR virus has been analyzed at the molecular level as reviewed in Ludwig (36). A restriction map of the genome is available in this reference, which will aid in the genetic engineering of IBR according to the methods provided by the present invention.

As reported in the current literature, IBR virus has been engineered to contain a thymidine kinase deletion (43,44) and a deletion in the gIII gene (45,46). However, no evidence has been presented for the deletions in the US2, repeat, gpG, or gpE regions. In the subject application, we demonstrate the usefulness of such deletions for both the attenuation of IBR virus and for the development of gene deleted marker vaccines.

As with other herpesviruses, IBR virus can become latent in healthy animals which makes them potential carriers of the virus. For this reason it is clearly advantageous to be able to distinguish animals vaccinated with non-virulent virus from animals infected with disease-causing wild type virus. The development of differential vaccines and companion diagnostic tests has proven valuable in the management of pseudorabies disease (47). A similar differential marker vaccine would be of great value in the management of IBR disease. The construction of differential diagnostics has focused on the deletion of glycoproteins. Theoretically, the glycoprotein chosen to be the diagnostic marker should have the following characteristics: (1) the glycoprotein and its gene should be non-essential for the production of infectious virus in tissue culture; (2) the glycoprotein should elicit a major serological response in the animal; and (3) the glycoprotein should not be one that makes a significant contribution to the protective immunity. Four major IBR virus glycoproteins (gI, gII, gIII, and gIV) have been described in the literature (48). Three of these genes, gI, gIII, and gIV, have been sequenced and shown to be homologous to the HSV glycoproteins gB, gC, and gD, respectively. Although it has been suggested that the gII protein is analogous to HSV gE, no sequence evidence has been presented to confirm that suggestion (48). The gB and gD homologues are essential genes and would not be appropriate as deletion marker genes. The gC gene of herpesviruses has been shown to make a significant contribution to protective immunity as a target of neutralizing antibody (49) and as a target of cell-mediated immunity (50). Therefore, the gC gene is not desirable as a deletion marker gene. As indicated above, Kit et al. (45) have described the deletion of the IBR virus gIII as a marker gene. It would be expected that such a deletion would compromise the efficacy of an IBR vaccine.

For pseudorabies virus (PRV) the criteria for a deletion marker gene are best met by the glycoprotein X (51). Wirth et al. (52) suggests the existence of a "gX homologue of HSV-1" in the IBR virus. It is not clear what is meant by this because although there is a PRV gX gene, there is no reported HSV-1 gX gene or gX homologous gene. In any case, no sequence evidence is presented to support this suggestion. We present clear evidence of homologues of PRV gX (HSV-2 gG) and PRV gI (HSV gE) in IBR virus and demonstrate their usefulness as diagnostic markers.

The present invention provides a method of producing a fetal-safe, live recombinant IBR virus which comprises treating viral DNA from naturally-occurring live IBR virus so as to delete from the virus DNA corresponding to the US2 region of the naturally-occurring IBR virus. The present invention also provides viruses in which (1) DNA corresponding to the US2 region of naturally-occurring IBR virus has been deleted, and (2) DNA encoding gpG and/or gpE has been altered or deleted. Such viruses are useful in vaccines which need diagnostic markers and are safe for use in pregnant animals.

The ability to engineer DNA viruses with large genomes, such as vaccinia virus and the herpesvirues, has led to the finding that these recombinant viruses can be used as vectors to deliver immunogens to animals (53). The herpesviruses are attractive candidates for development as vectors because their host range is primarily limited to a single target species (54), and they have the capacity for establishing a latent infection (55) that could provide for stable in vivo expression of a desired cloned polypeptide. Herpesviruses have been engineered to express a variety of foreign gene products, such as bovine growth hormone (56), human tissue plasminogen activator (57), and *E. coli* β-galactosidase (58,59). In addition, possible immunogenic polypeptides have been expressed by herpesviruses. Whealy et al. (60) expressed portions of the human immunodeficiency virus type 1 envelope glycoprotein in pseudorabies virus (PRV) as fusions to the PRV glycoprotein III. The hepatitis B virus surface antigen (61) and a hybrid human malaria antigen from Plasmodium falciparum have been expressed in herpes simplex virus type 1 (HSV-1) (62). The IBR viruses described above may be used as vectors for the insertion of genes encoding antigens from microorganisms causing important cattle diseases. Such recombinant viruses would be multivalent vaccines protecting against IBR as well as other diseases. Kit et al. (63) have described the expression of a Foot and Mouth disease antigen in IBR virus. In some of the prior applications from which the subject application claims priority (which precedes the Kit publication by at least three years), we described the use of IBR virus to express several foreign genes including the *E. coli* β-galactosidase (lacZ) gene, the TN5 neomycin resistance gene, and antigens from bovine rota virus, and parainfluenza-3 virus (see U.S. Ser. No. 06/933,107, filed Nov. 20, 1986 and U.S. Ser. No. 07/078,519, filed Jul. 27, 1987). These applications precede the Kit publication by at least three years. The viruses described in this application provide a combination of attenuation, differentiation and multivalency. These properties make such viruses useful as vaccines for the management of cattle diseases.

SUMMARY OF THE INVENTION

The present invention provides recombinant infectious bovine rhinotracheitis (IBR) viruses useful in vaccines to protect bovines from infectious bovine rhinotracheitis and other bovine diseases. The present invention further provides methods for distinguishing an animal vaccinated with the vaccine of the present invention from an animal infected with a naturally-occurring IBR virus. The present invention also provides isolated DNA encoding the gpE glycoprotein of IBR virus and isolated DNA encoding the gpG glycoprotein of IBR virus. The present invention also provides a method of producing a fetal-safe, live recombinant IBR virus which comprises treating viral DNA from a naturally-occurring live IBR virus so as to delete from the virus DNA corresponding to the US2 region of the naturally-occurring IBR virus.

BRIEF DESCRIPTION OF THE FIGURES

FIG. 3 SEQ ID NO: 1 DNA sequence of the IBR Unique Short 2 gene. The sequence of the first 1080 base pairs of the HindIII K fragment, reading from the HindIII K/HindIII O junction, are shown. The unique short 2 (US2) gene is transcribed toward the HindIII K/HindIII O junction as indicated in FIG 1. The sequence has been reversed and complemented in order to show the translation start and termination of the US2 gene.

(FIG. 4A) Matrix plot of the amino acid sequence of the IBR US2 protein (309) against the amino acid sequence of the HSV-1 US2 protein (291) (8). FIG. 4B Alignment of a conserved region between IBR US2 protein, HSV-1 US2 protein, PRV US2 protein (256 amino acids) (21), HSV-2 US2 protein (291) (9), and MDV US2 protein (270 amino acids) (1).

FIG. 8 SEQ ID NO: 16 DNA sequence of the IBR glycoprotein G gene. The sequence of approximately 1400 base pairs of the HindIII K fragment, starting approximately 2800 base pairs downstream of the HindIII K/HindIII O junction, are shown. The glycoprotein G (gpG) gene is transcribed away from the HindIII K/HindIII O junction as indicated in FIG. 1. The translational start and termination of the gpG gene are indicated.

(FIG. 9A) Matrix plot of the amino acid sequence of the IBR gpG protein (441) against the amino acid sequence of the PRV gpX protein (498) (12). (FIG. 9B) Alignment of the conserved region between IBR gpG protein, PRV gpX protein, and HSV-2 gpG protein (699) (9). Note that IUPAC-IUB Biochemical Nomenclature Commission conventions are used.

FIG. 15 SEQ ID NO: 36 DNA sequence of the IBR glycoprotein E gene. The sequence of 2038 base pairs of the IBR unique short region, starting approximately 1325 base pairs upstream of the HindIII K/HindIII F junction in the HindIII K fragment, are shown. The glycoprotein E (gpE) gene is transcribed toward the HindIII K/HindIII F junction as indicated in FIG. 1. The translational start and termination of the gpE gene are indicated. Note that IUPAC-IUB Biochemical Nomenclature Commission conventions are used.

FIGS. 16A & 16B SEQ ID NOS: 37–40 Homology between the IBR gpE (SEQ ID NO: 40) protein and the gpE protein of HSV-1, (SEQ ID NO: 37) the gpI protein of VZV (SEQ ID NO: 39), and the gI protein of PRV SEQ ID NO: 38. FIG. 16A Matrix plot of the amino acid sequence of the IBR gpE protein (617) against the amino acid sequence of the PRV gI protein (577) (64). (FIG. 16B) Alignment of the conserved region between IBR gpE protein, PRV gI protein, and VZV gpI protein (37).

The sequences (SEQ ID NOS: 44–48) located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: glycoprotein E (gpE), immediate early promoter (IE), infectious bovine rhinotracheitis virus (IBR), and pseudorabies virus (PRV).

Figure 19:
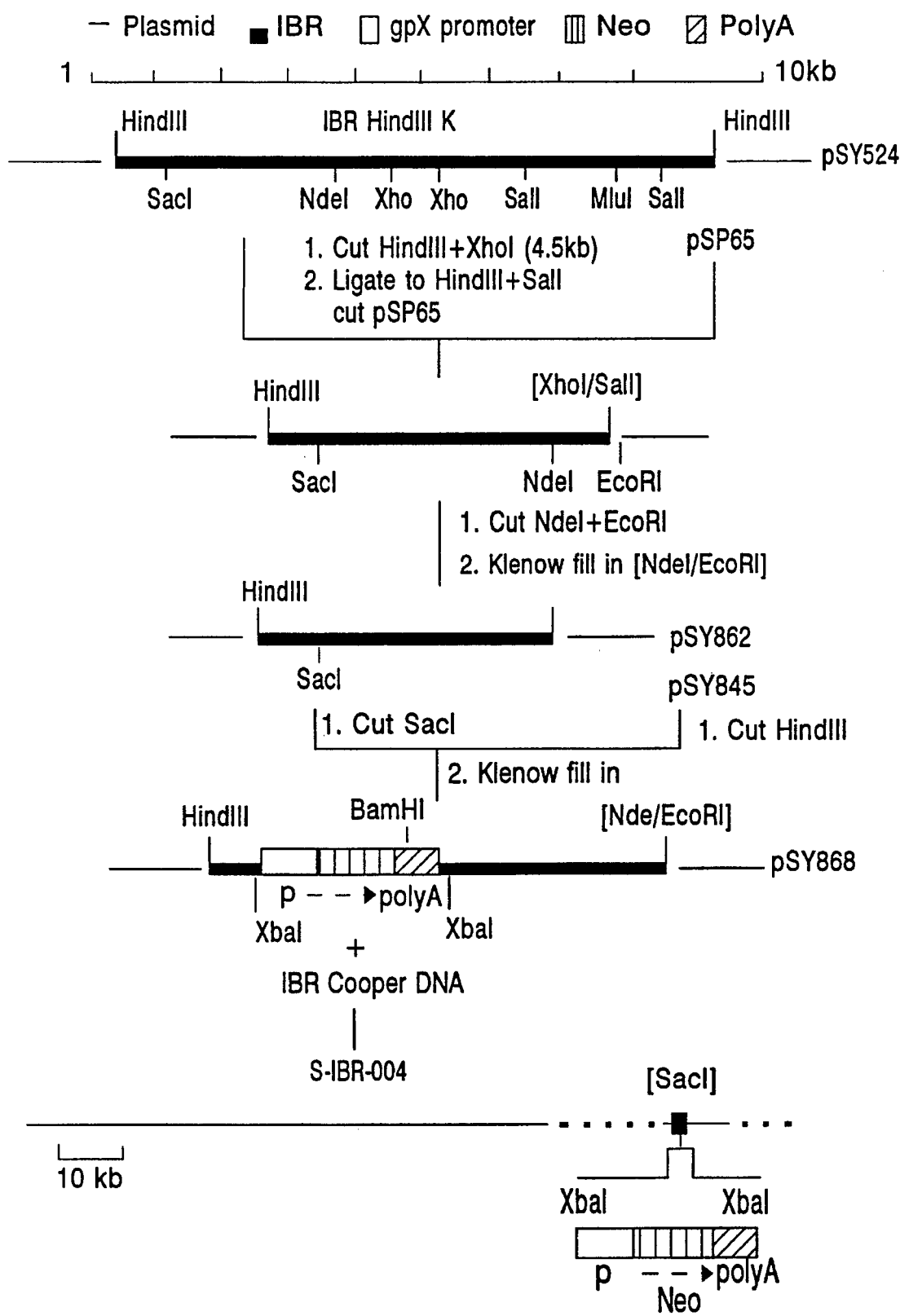

FIG. 19 Construction of Recombinant S-IBR-004 Virus. S-IBR-004 is an IBR recombinant virus carrying an inserted foreign gene (NEO) under the control of the PRV gpX promoter. A new XbaI site was created at the short unique region and the original SacI site was deleted.

Figure 20:
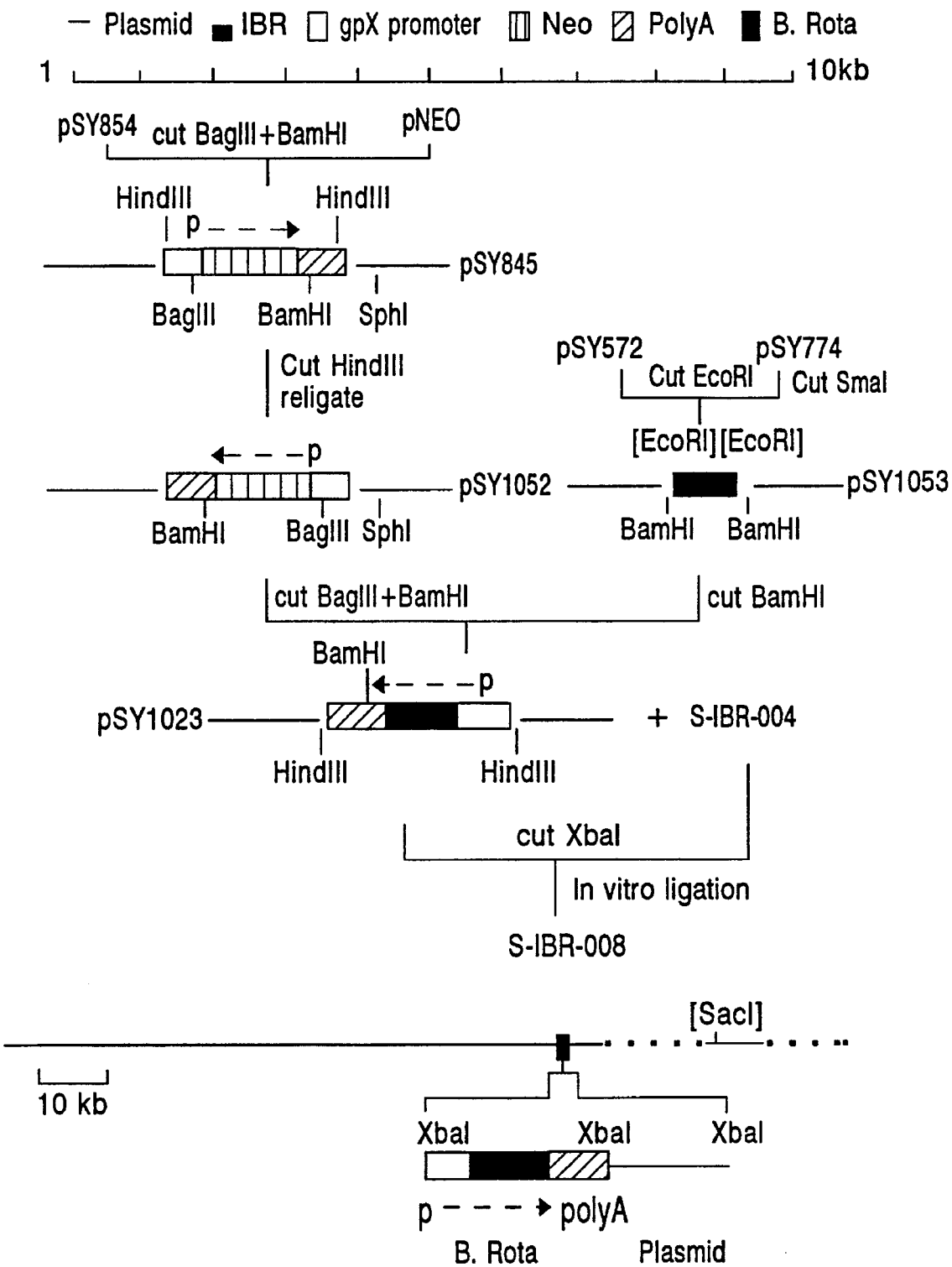

FIG. 20 Construction of Recombinant S-IBR-008 Virus. S-IBR-008 is a recombinant IBR virus that has a bovine rotavirus glycoprotein gene and the plasmid vector inserted at the XbaI site in the unique long region. A site specific deletion was created at the [SacI] site due to the loss of NEO gene in the short unique region.

FIG. 21 SEQ ID NO: 49 Sequence of the PI-3 (SF-4 Strain) HN Gene. Note that IUPAC-IUB Biochemical Nomenclature Commission conventions are used.

FIG. 22A–22C Details of S-IBR-018 Construction.

FIG. 22A First line shows the IBR (Cooper Strain) BamHI-C fragment map. Second line shows the construction of the alpha-4 promoter on the PI-3 HN gene and its insertion into the HindIII site in BamHI-C. Also shown are the beta-gal and neomycin (NEO) gene constructions under the control of the gX promoter that were put into the XbaI site and used as selectable markers to purify the recombinant virus.

FIG. 22B The BamHI-C fragment map of S-IBR-018 after insertion of the PI-3 HN, beta-gal, and neomycin genes.

FIG. 22C The S-IBR-018 genome showing the location of the three inserted foreign genes.

Legend:
B=BamHI; H=HindIII; X=XbaI; S=StuI; UL =unique long region; US=unique short region; IR=internal repeat region; TR=terminal repeat region.

Figure 23A:
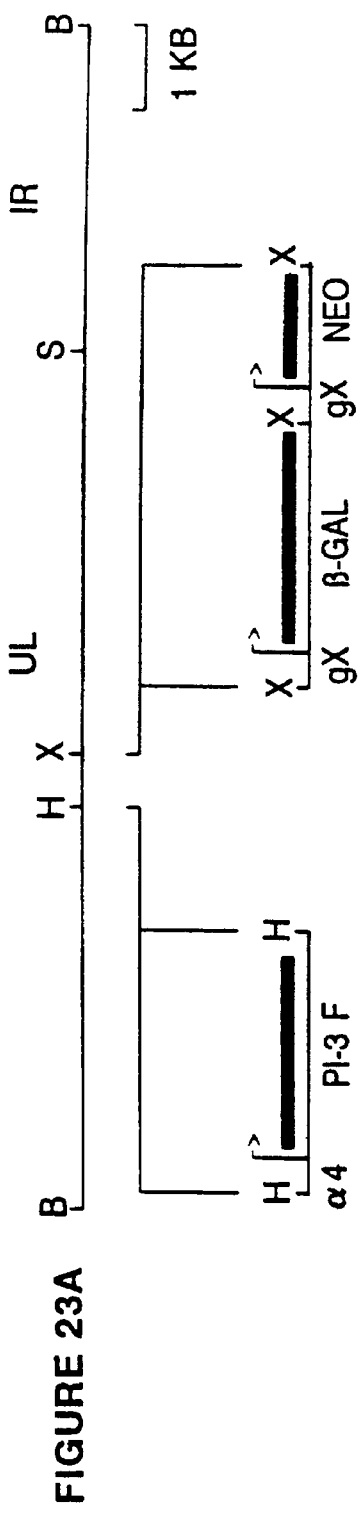
Figure 23B:
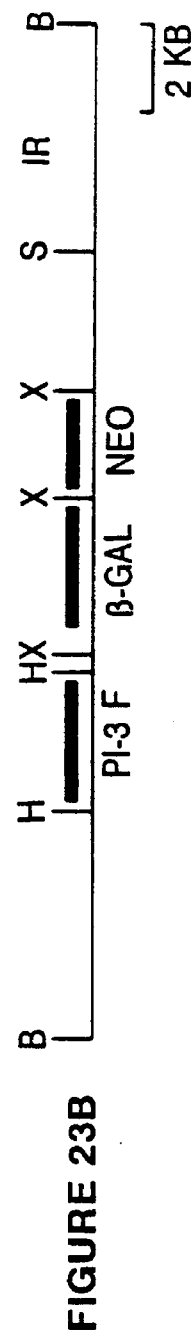
Figure 23C:
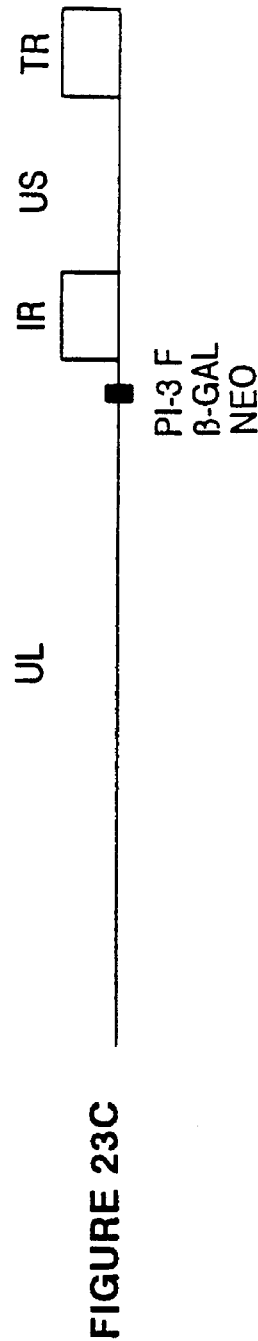

FIGS. 23A–23C Details of S-IBR-019 Construction.

FIG. 23A First line shows the IBR (Cooper Strain) BamHI-C fragment map. Second line shows the construction of the alpha-4 promoter on the PI-3 F gene and its insertion into the HindIII site in BamHI-C. Also shown are the beta-gal and neomycin (NEO) gene constructions under the control of the gX promoter that were put into the XbaI site and used as selectable markers to purify the recombinant virus.

FIG. 23B The BamHI-C fragment map of S-IBR-019 after insertion of the PI-3 F, beta gal, and neomycin genes.

FIG. 23C The S-IBR-019 genome showing the location of the three inserted foreign genes.

Legend:
B=BamHI; H=HindIII; X=XbaI; S=StuI; UL =unique long region; US=unique short region; IR=internal repeat region; TR=terminal repeat region.

DETAILED DESCRIPTION OF THE INVENTION

The present invention provides a recombinant IBR virus comprising viral DNA from a naturally-occurring IBR virus in which DNA encoding gpG glycoprotein has been altered or deleted so that upon replication the recombinant IBR virus produces no gpG glycoprotein. The DNA encoding gpG glycoprotein may be deleted or foreign DNA may be inserted into the DNA encoding gpG glycoprotein. The DNA encoding gpG glycoprotein may be deleted and foreign DNA may be inserted in place of the deleted DNA encoding gpG glycoprotein.

The present invention further provides a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein. The DNA encoding gpE glycoprotein may be deleted or foreign DNA may be inserted into the DNA encoding gpE glycoprotein. The DNA encoding gpE glycoprotein may be deleted and foreign DNA may be inserted in place of the deleted DNA encoding gpE glycoprotein.

The present invention further provides a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted.

The present invention also provides a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been altered or deleted. The DNA encoding the gpG glycoprotein may be deleted or foreign DNA may be inserted in place of the deleted DNA encoding gpG glycoprotein. Foreign DNA may be inserted in place of the deleted DNA corresponding to the US2 region of the naturally-occurring IBR virus.

The present invention also provides S-IBR-037, a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been deleted. S-IBR-037 has been deposited on Apr. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2320.

The present invention also provides a recombinant IBR virus comprising viral DNA from a naturally-occurring IBR virus in which (1) DNA corresponding to the US2 region of the naturally-occurring IBR virus has been deleted and a foreign DNA sequence which encodes *Escherichia coli* β-galactosidase has been inserted in place of the deleted DNA encoding gpG glycoprotein, and (2) DNA encoding gpG glycoprotein has been altered or deleted. The present invention also provides two examples of such viruses, S-IBR-035 and S-IBR-036.

The present invention further provides a recombinant IBR virus comprising viral DNA from a naturally-occurring IBR virus in which DNA encoding gpE glycoprotein has been altered or deleted so that upon replication the recombinant IBR virus produces no gpE glycoprotein. The DNA encoding gpE glycoprotein may be deleted or foreign DNA may be inserted in the DNA encoding gpE glycoprotein. The DNA encoding gpE glycoprotein may be deleted and foreign DNA may be inserted in place of the deleted DNA encoding gpE glycoprotein.

The present invention further provides a recombinant IBR virus comprising viral DNA from a naturally-occurring IBR virus in which DNA encoding gpE glycoprotein has been altered or deleted so that upon replication the recombinant IBR virus produces no gpE glycoprotein and DNA corresponding to the US2 region of the naturally-occurring IBR virus has been deleted.

The present invention further provides a recombinant IBR virus comprising viral DNA from a naturally-occurring IBR virus from which DNA corresponding to the US2 region of the naturally-occurring IBR virus has been deleted. Foreign DNA may be inserted into the DNA of the recombinant IBR virus. The foreign DNA may be inserted into the XbaI site in the long unique region. The foreign DNA may be a sequence which encodes bovine rotavirus glycoprotein 38; this sequence may be inserted into the XbaI site in the long unique region.

The present invention provides S-IBR-008, a recombinant IBR virus comprising viral DNA from a naturally-occurring IBR virus from which DNA corresponding to the US2 region of the naturally-occurring IBR virus has been deleted and in which a foreign DNA sequence which encodes bovine rotavirus glycoprotein 38 has been inserted into the XbaI site in the long unique region. S-IBR-008 has been deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2141.

The present invention further provides a recombinant IBR virus comprising viral DNA from a naturally-occurring IBR virus from which (1) DNA corresponding to the US2 region of the naturally-occurring IBR virus has been deleted and (2) at least a portion of both repeat sequences has been deleted. The present invention further provides an example of such a recombinant virus, designated S-IBR-027. S-IBR-027 has been deposited on Apr. 17, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2322.

The present invention further provides a recombinant IBR virus comprising viral DNA from a naturally-occurring IBR virus from which at least a portion of both repeat sequences has been deleted.

The present invention further provides a recombinant IBR virus comprising viral DNA from a naturally-occurring IBR virus from which (1) at least a portion of both repeat sequences has been deleted and (2) DNA encoding one or more EcoRV restriction sites has been deleted. The present invention further provides an example of such a recombinant virus, designated S-IBR-002. S-IBR-002 has been deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2140.

The present invention further provides a recombinant IBR virus comprising viral DNA from a naturally-occurring IBR virus from which (1) at least a portion of both repeat sequences has been deleted and (2) wherein foreign DNA has been inserted into the DNA of the recombinant IBR virus. The foreign DNA may be a sequence which encodes the Tn5 NEO gene.

The present invention further provides S-IBR-020, a recombinant IBR virus comprising viral DNA from a naturally-occurring IBR virus from which (1) at least a portion of both repeat sequences has been deleted and (2) wherein a foreign DNA sequence which encodes the Tn5 NEO gene has been inserted into the DNA of the recombinant IBR virus.

The present invention also provides a recombinant IBR virus comprising viral DNA from a naturally-occurring IBR virus from which (1) at least a portion of both repeat sequences has been deleted, (2) wherein a foreign DNA sequence which encodes the Tn5 NEO gene has been inserted into the DNA of the recombinant IBR virus, and (3) wherein at least a portion of the thymidine kinase gene has been deleted.

The present invention also provides a recombinant IBR virus comprising viral DNA from a naturally-occurring IBR virus from which (1) at least a portion of both repeat sequences has been deleted, (2) wherein a foreign DNA sequence which encodes the Tn5 NEO gene has been inserted into the DNA of the recombinant IBR virus and the Tn5 NEO gene is under the control of an inserted, upstream, HSV-1 alpha-4 promoter, and (3) wherein at least a portion of the thymidine kinase gene has been deleted. The subject invention provides an example of such a recombinant virus, designated S-IBR-028. S-IBR-028 has been deposited on May 14, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2326.

The present invention further provides a recombinant IBR virus comprising viral DNA from a naturally-occurring IBR virus in which a foreign DNA sequence which encodes the Tn5 NEO gene has been inserted into the viral DNA. The Tn5 NEO gene may be under the control of an inserted, upstream, pseudorabies virus glycoprotein X promoter. The subject invention further provides an example of a recombinant virus wherein the Tn5 NEO gene is under the control of an inserted, upstream, pseudorabies virus glycoprotein X promoter, designated S-IBR-004. S-IBR-004 has been deposited on May 23, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2134.

The subject invention further provides a recombinant IBR virus comprising viral DNA from a naturally-occurring IBR virus in which a foreign DNA sequence which encodes the *Escherichia coli* β-galactosidase and Tn5 NEO genes, and the parainfluenzae-3 virus hemaglutinin gene, HN, has been inserted into the viral DNA. The subject invention provides an example of such a recombinant virus, designated S-IBR-018.

The subject invention further provides a recombinant IBR virus comprising viral DNA from a naturally-occurring IBR virus in which a foreign DNA sequence which encodes the *Escherichia coli* β-galactosidase and Tn5 NEO genes, and the parainfluenzae-3 virus virus fusion gene, F, has been inserted into the viral DNA. The subject invention provides an example of such a recombinant virus, designated S-IBR-019.

The recombinant viruses of the subject invention were derived from the Cooper Strain. However, other IBR viruses, such as the LA strain or the 3156 strain, may also be used.

The subject invention also provides a vaccine which comprises a suitable carrier and an effective immunizing amount of any of the recombinant viruses of the present invention. The vaccine may contain either inactivated or live recombinant virus.

Suitable carriers for the recombinant virus are well known in the art and include proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilized, hydrolyzed proteins. Preferably, the inactivated vaccine uses tissue culture fluids directly after inactivation of the virus.

The subject invention also provides a vaccine which comprises a suitable carrier and an effective immunizing amount of a recombinant virus comprising viral DNA from a naturally-occurring IBR virus in which DNA encoding gpG glycoprotein has been altered or deleted so that upon replication the recombinant IBR virus produces no gpG glycoprotein.

The subject invention provides a vaccine which comprises a suitable carrier and an effective immunizing amount of a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein.

The subject invention also provides a vaccine which comprises a suitable carrier and an effective immunizing amount of a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted.

The subject invention further provides a vaccine which comprises a suitable carrier and an effective immunizing amount of a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been altered or deleted.

The subject invention also provides a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein.

The subject invention provides a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein and DNA corresponding to the US2 region of the naturally-occurring IBR virus has been deleted.

The subject invention also provides a vaccine which comprises a suitable carrier and an effective immunizing amount of a recombinant IBR virus comprising viral DNA from a naturally-occurring IBR virus from which DNA corresponding to the US2 region of the naturally-occurring IBR virus has been deleted.

The subject invention provides a vaccine which comprises a suitable carrier and an effective immunizing amount of a recombinant IBR virus comprising viral DNA from a naturally-occurring IBR virus from which at least a portion of both repeat sequences has been deleted.

The subject invention further provides a vaccine which comprises a suitable carrier and an effective immunizing amount of a recombinant IBR virus comprising viral DNA from a naturally-occurring IBR virus in which a foreign DNA sequence which encodes the Tn5 NEO gene has been inserted into the viral DNA.

The subject invention also provides a vaccine which comprises a suitable carrier and an effective immunizing amount of a recombinant IBR virus comprising viral DNA from a naturally-occurring IBR virus in which a foreign DNA sequence which encodes the *Escherichia coli* β-galactosidase and Tn5 NEO genes, and the parainfluenzae-3 virus hemaglutinin gene, HN, has been inserted into the viral DNA.

The subject invention also provides a vaccine which comprises a suitable carrier and an effective immunizing amount of a recombinant IBR virus comprising viral DNA from a naturally-occurring IBR virus in which a foreign DNA sequence which encodes the *Escherichia coli* β-galactosidase Tn5 NEO genes, and the parainfluenzae-3 virus fusion gene, F, has been inserted into the viral DNA.

All of the vaccines described above may contain either inactivated or live recombinant virus. The vaccines may be administered by any of the methods well known to those skilled in the art, for example, by intramuscular, subcutaneous, intraperitoneal, or intravenous injection. Alternatively, the vaccine may be administered intranasally or orally.

The present invention also provides a method of immunizing an animal against infectious bovine rhinotracheitis virus which comprises administering to the animal an effective immunizing dose of any of the vaccines of the present invention. The animal may be a bovine.

The subject invention also provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gpG glycoprotein of IBR virus and at least one other antigen normally expressed in an animal infected by a naturally-occurring IBR virus, identifying antigens which are present in the body fluid, and determining whether gpG glycoprotein is present in the body fluid. The presence of antigens which are normally expressed in an animal by a naturally-occurring IBR virus and the absence of gpG glycoprotein in the body fluid is indicative of an animal vaccinated with the vaccine and not infected with a naturally-occurring IBR virus. The presence of antigens and gpG glycoprotein in the body fluid may be determined by detecting in the body fluid antibodies specific for the antigens and gpG glycoprotein.

One of the vaccines that is useful in this method is a vaccine which comprises a suitable carrier and an effective immunizing amount of a recombinant virus comprising viral DNA from a naturally-occurring IBR virus in which DNA encoding gpG glycoprotein has been altered or deleted so that upon replication the recombinant IBR virus produces no gpG glycoprotein. Another vaccine that is useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein. Yet another vaccine that is useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted. Still another vaccine that is useful in this method is a vaccine which comprises a suitable carrier and an effective immunizing amount of a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been altered or deleted.

The present invention also provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gpE glycoprotein of IBR virus and at least one other antigen normally expressed in an animal infected by a naturally-occurring IBR virus, identifying antigens which are present in the body fluid and determining whether gpE glycoprotein is present in the body fluid the presence of antigens which are normally expressed in an animal by a naturally-occurring IBR virus and the absence of gpE glycoprotein in the body fluid is indicative of an animal vaccinated with the vaccine and not infected with a naturally-occurring IBR virus. The presence of antigens and gpE glycoprotein in the body fluid may be determined by detecting in the body fluid antibodies specific for the antigens and gpE glycoprotein.

One of the vaccines useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein. Another vaccine that is useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted. Yet another vaccine that is useful in this method is a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein. Still another vaccine that is useful in this method is a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein and DNA corresponding to the US2 region of the naturally-occurring IBR virus has been deleted.

The present invention also provides isolated DNA encoding the gpG glycoprotein of IBR virus. The subject invention also provides purified recombinant gpG glycoprotein encoded by the DNA encoding the gpG glycoprotein of IBR virus. The subject invention further provides a recombinant cloning vector which comprises the DNA encoding the gpG glycoprotein of IBR virus. The subject invention also provides a recombinant expression vector which comprises the DNA encoding the gpG glycoprotein of IBR virus. The subject invention provides a host cell which comprises the recombinant expression vector which comprises the DNA encoding the gpG glycoprotein of IBR virus.

The subject invention also provides a method of producing a polypeptide which comprises growing the host cell which comprises the recombinant expression vector which comprises the DNA encoding the gpG glycoprotein of IBR virus under conditions such that the recombinant expression vector expresses gpG glycoprotein and recovering the gpG glycoprotein so expressed.

The subject invention also provides an antibody directed to an epitope of the purified gpG glycoprotein of IBR virus encoded by the DNA encoding the gpG glycoprotein of IBR virus. The antibody may be a monoclonal antibody.

The subject invention also provides a method of detecting the presence or absence of gpG glycoprotein of IBR virus in a sample which comprises contacting the sample with an antibody directed to an epitope of the purified gpG glycoprotein of IBR virus encoded by the DNA encoding the gpG glycoprotein of IBR virus under conditions such that the antibody forms a complex with any gpG glycoprotein present in the sample and detecting the presence or absence of such complex. The sample may be bovine-derived.

The subject invention also provides isolated DNA encoding the gpE glycoprotein of IBR virus. The subject invention also provides purified recombinant gpE glycoprotein encoded by the DNA encoding the gpE glycoprotein of IBR virus. The subject invention further provides a recombinant cloning vector which comprises the DNA encoding the gpE glycoprotein of IBR virus. The subject invention provides a recombinant expression vector which comprises the DNA encoding the gpE glycoprotein of IBR virus. The subject invention also provides a host cell which comprises the recombinant expression vector which comprises the DNA encoding the gpE glycoprotein of IBR virus.

The subject invention also provides a method of producing a polypeptide which comprises growing the host cell which comprises the recombinant expression vector which comprises the DNA encoding the gpE glycoprotein of IBR virus under conditions such that the recombinant expression vector expresses gpE glycoprotein and recovering the gpE glycoprotein so expressed.

The subject invention also provides an antibody directed to an epitope of the purified gpE glycoprotein of IBR virus encoded by the DNA encoding the gpE glycoprotein of IBR virus. The antibody may be a monoclonal antibody.

The subject invention also provides a method of detecting the presence or absence of gpE glycoprotein of IBR virus in a sample which comprises contacting the sample with an antibody directed to an epitope of the purified gpE glycoprotein of IBR virus encoded by the DNA encoding the gpE glycoprotein of IBR virus under conditions such that the antibody forms a complex with any gpE glycoprotein present in the sample and detecting the presence or absence of such complex. The sample may be bovine-derived.

The subject invention also provides a method of producing a fetal-safe, live recombinant IBR virus which comprises treating viral DNA from a naturally-occurring live IBR virus so as to delete from the virus DNA corresponding to the US2 region of the naturally-occurring IBR virus.

The subject invention also provides a recombinant pseudorabies virus designated S-PRV-160. The subject invention also provides an antibody directed to an epitope of the recombinant pseudorabies virus designated S-PRV-160.

Materials and Methods

PREPARATION OF IBR VIRUS STOCK SAMPLES. IBR virus stock samples were prepared by infecting MDBK cells at a multiplicity of infection of 0.01 PFU/cell in Dulbecco's Modified Eagle Medium (DMEM) containing 2 mM glutamine, 100 units/ml penicillin, 100 units/ml streptomycin (these components were obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Cells were resuspended in ¹⁄₁₀ the original volume of medium, and an equal volume of skim milk (9% skim milk powder in $H_2O$ weight/volume) was added. The virus sample was frozen at −70° C. The titers were usually about $10^8$ PFU/ml.

PREPARATION OF HERPESVIRUS DNA. For herpesvirus DNA preparation, a confluent monolayer of cells (MDBK for IBR virus or Vero for PRV) in a 25 $cm^2$ flask or 60 mm petri dish was infected with 100 μl of virus sample. After overnight incubation, or when the cells were showing 100% cytopathic effect, the cells were scraped into the medium. The cells and medium were centrifuged at 3000 rpm for 5 minutes in a clinical centrifuge. The medium was decanted, and the cell pellet was gently resuspended in 0.5 ml of solution containing 0.5% Nonident P-40 (NP-40, purchased from Sigma Chemical Co., St. Louis, Mo.). The sample was incubated at room temperature for 10 minutes. Ten μl of a stock solution of RNase A (Sigma) was added (stock was 10 mg/ml, boiled for 10 minutes to inactivate DNAse). The sample was centrifuged to pellet nuclei. The DNA pellet was removed with a pasteur pipette or wooden stick and discarded. The supernatant fluid was decanted into a 1.5 ml Eppendorf tube containing 25 μl of 20% sodium dodecyl sulfate (Sigma) and 25 μl proteinase-K (10 mg/ml; Boehringer Mannheim). The sample was mixed and incubated at 37° C. for 30–60 minutes. An equal volume of water-saturated phenol was added and the sample was mixed briefly. The sample was centrifuged in an Eppendorf minifuge for 5 minutes at full speed. The upper aqueous phase was removed to a new Eppendorf tube, and two volumes of absolute ethanol were added and the tube put at −20° C. for 30 minutes to precipitate nucleic acid. The sample was centrifuged in an Eppendorf minifuge for 5 minutes. The supernatant was decanted and the pellet was washed with ⁻300 μl of 80% ethanol, followed by centrifugation in an Eppendorf minifuge for 5 minutes. The supernatant was decanted, and the pellet was air dried and rehydrated in ⁻16 μl $H_2O$. For the preparation of larger amounts of DNA, the procedure was scaled up to start with a 850 $cm^2$ roller bottle of MDBK cells. The DNA was stored in 0.01M tris pH 7.5, 1 mM EDTA at 4° C.

PREPARATION OF HERPESVIRUS CELL LYSATES. For cell lysate preparation, serum free medium was used. A confluent monolayer of cells (MDBK for IBR virus or Vero for PRV) in a 25 cm² flask or a 60 mm petri dish was infected with 100 μl of virus sample. After cytopathic effect was complete, the medium and cells were harvested and the cells were pelleted at 3000 rpm for 5 minutes in a clinical centrifuge. For media samples medium was concentrated approximately 10-fold by filtration with a centricon-10 microconcentrator (Amicon). For cell samples the cell pellet was resuspended in 250 μl of disruption buffer (2% sodium dodecyl sulfate, 2% β-mercaptoethanol). The samples were sonicated for 30 seconds on ice and stored at −20° C.

WESTERN BLOTTING PROCEDURE. Samples of lysates, controls and protein standards were run on a polyacrylamide gel according to the procedure of Laemmli (2). After gel electrophoresis the proteins were transferred according to Sambrook (14). The primary antibody was a mouse hyper-immune serum raised against chemically-synthesized gpG peptides (amino acids 232–252 and 267–287) linked to keyhole limpet hemocyanin. The secondary antibody was a goat anti-mouse alkaline phosphatase coupled antibody.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis (6). Except as noted, these were used with minor variation.

LIGATION. DNA was joined together by the action of the enzyme T4 DNA ligase (BRL). Ligation reactions contained various amounts of DNA (from 0.2 to 20 μg), 20 mM Tris pH 7.5, 10 mM $MgCl_2$, 10 mM dithiothreitol (DTT), 200 μM ATP and 20 units T4 DNA ligase in 10–20 μl final reaction volume. The ligation proceeded for 3–16 hours at 15° C.

DNA SEQUENCING. Sequencing was performed using the BRL "SEQUENASE", a modified bacteriophage T7 DNA plymerase (United States Biochemicals, Cleveland, Ohio) Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

SOUTHERN BLOTTING OF DNA. The general procedure for Southern blotting was taken from Maniatis (6). DNA was blotted to nitrocellulose filters and hybridized to appropriately labeled DNA probes. Probes for southern blots were prepared using either the Nonradioactive DNA Labeling and Detection Kit of Boehringer Mannheim or the nick translation kit of Bethesda Research Laboratories (BRL). In both cases the manufacturers' recommended procedures were followed.

DNA TRANSFECTION FOR GENERATING RECOMBINANT VIRUS. The method is based upon the calcium phosphate procedure of Graham and Van der Eb (4) with the following modifications. Virus and/or plasmid DNA were diluted to 298 μl in 0.01M Tris pH 7.5, 1 mM EDTA. Forty μl 2M $CaCl_2$ was added followed by an equal volume of 2× HEPES buffered saline (10g N-2-hydroxyethyl piperazine N'-2-ethanesulfonic acid (HEPES), 16g NaCl, 0.74 g KCl, 0.25 g $Na_2HPO_4·2H_2O$, 2 g dextrose per liter $H_2O$ and buffered with NaOH to pH 7.4). The mixture was then incubated on ice for 10 minutes, and then added dropwise to an 80% confluent monolayer of MDBK or rabbit skin (RS) cells growing in a 60 mm petri dish under 5 ml of medium (DME plus 2% fetal bovine serum). The cells were incubated 4 hours at 37° C. in a humidified incubator containing 5% $CO_2$. The cells were then washed with three 5 ml aliquots of 1XPBS (1.15 g $Na_2HPO_4$, 0.2 g $KH_2PO_4$, 0.8 g NaCl, 0.2 g KCl per liter $H_2O$), and fed with 5 ml of medium (DME plus 2% fetal bovine serum). The cells were incubated at 37° C. as above for 3–7 days until cytopathic effect from the virus was 50–100%. Virus was harvested as described above for the preparation of virus stocks. This stock was referred to as a transfection stock and was subsequently screened for recombinant virus by the BLUOGAL SCREEN FOR RECOMBINANT IBR VIRUS.

HOMOLOGOUS RECOMBINATION PROCEDURE FOR GENERATING RECOMBINANT HERPESVIRUS. This method relies upon the homologous recombination between herpesvirus DNA and plasmid homology vector DNA which occurs in tissue culture cells co-transfected with these elements. From 0.1–1.0 μg of plasmid DNA containing foreign DNA flanked by appropriate herpesvirus cloned sequences (the homology vector) were mixed with approximately 0.3 μg of intact herpesvirus DNA. The DNAs were diluted to 298 μl in 0.01M Tris pH 7.5, 1 mM EDTA and transfected into MDBK cells according to the DNA TRANSFECTION FOR GENERATING RECOMBINANT VIRUS (see above).

DIRECT LIGATION PROCEDURE FOR GENERATING RECOMBINANT HERPESVIRUS. Rather than using homology vectors and relying upon homologous recombination to generate recombinant virus, we have also developed the technique of direct ligation to engineer herpesviruses. In this instance, a cloned foreign gene did not require flanking herpesvirus DNA sequences but only required that it have restriction sites available to cut out the foreign gene fragment from the plasmid vector. A compatible restriction enzyme was used to cut herpesvirus DNA. A requirement of the technique was that the restriction enzyme used to cut the herpesvirus DNA must cut at a limited number of sites. We have used XbaI, which cuts IBR virus DNA in one place. We have also used EcoRV which cuts IBR virus DNA in two places. For PRV we have used XbaI and HindIII, both of which cut in two places. Restriction sites previously introduced into herpesviruses by other methods may also be used. The herpesvirus DNA was mixed with a 30-fold molar excess of plasmid DNA (typically 5 μg of virus DNA to 10 μg of plasmid DNA), and the mixture was cut with the appropriate restriction enzyme. The DNA mixture was phenol extracted and ethanol precipitated to remove restriction enzymes, and ligated together according to the ligation procedure detailed above. The ligated DNA mixture was then resuspended in 298 μl 0.01M Tris pH 7.5, 1 mM EDTA and transfected into cells (MDBK or RS for IBR virus and Vero for PRV) according to the DNA TRANSFECTION FOR GENERATING RECOMBINANT VIRUS (see above). The direct ligation procedure may also be used to delete DNA from herpesviruses. Non-essential DNA which is flanked by appropriate restriction enzyme sites may be deleted by digesting the virus DNA with such enzymes and religation. The frequency of engineered viruses generated by the direct ligation procedure is high enough that screening can be accomplished by restriction enzyme analysis of randomly picked plaques from the transfection stock.

BLUOGAL SCREEN FOR RECOMBINANT HERPESVIRUS. When the E. coli β-galactosidase (lacZ) marker gene was incorporated into a recombinant virus the plaques containing recombinants were visualized by a simple assay. The chemical Bluogal™ (Bethesda Research Labs) was incorporated (200 µg/ml) into the agarose overlay during the plaque assay, and plaques that expressed active β-galactosidase turned blue. The blue plaques were then picked onto fresh cells (MDBK for IBR virus and Vero for PRV) and purified by further blue plaque isolations. In recombinant virus strategies in which the E. coli β-galactosidase marker gene is removed, the assay involves plaque purifying white plaques from a background of parental blue plaques. In both cases viruses were typically purified with three rounds of plaque purification.

ANTIBODY SCREEN FOR RECOMBINANT HERPESVIRUS. A third method for screening the recombinant virus stock was to look directly for the expression of the foreign gene with antibodies. Herpesvirus plaques were spotted and picked by inserting a toothpick through the agarose above the plaque and scraping the plaque area on the dish. Viruses were then rinsed from the toothpick by inserting the toothpick into a well of a 96-well micro-titer dish (Falcon Plastics) containing a confluent monolayer of tissue culture cells that had been washed 3 times in DME medium without serum. It was important for the virus to grow without serum at this stage to allow the immunological procedure to work. After cytopathic effect was complete, the plates were put at −70° C. to freeze and lyse the cells. The medium was thawed, and the freeze/thaw procedure was repeated a second time. Then 50–100 microliters of medium were removed from each well and filtered under vacuum through a nitrocellulose membrane (S&S BA85) using a DotBlot~ apparatus (BRL). The filter blots were soaked in a blocking solution of 0.01M Tris pH 7.5, 0.1M NaCl, 3% bovine serum albumin at room temperature for two hours with shaking. The filter blots were then placed in a sealable bag (Sears Seal-A-Meal™ or equivalent), and 10 mls of the blocking solution that contained 10 microliters of antibody specific for the foreign protein were added. After overnight incubation at room temperature with shaking, the blot was washed 3 times with 100 mls 0.01M Tris, pH 7.5, 0.1M NaCl, 0.05% Tween 20 detergent (Sigma). The blot was put in another sealable bag and 10 mls blocking solution containing $10^6$ counts per minute of $^{125}$I-protein A (New England Nuclear) were added. After allowing the protein A to bind to the antibody for 2 hours at room temperature with shaking, the blot was washed as above, dried, and overlayed with an X-ray film and an intensifying screen (Dupont) and autoradiographed for 1–3 days at −70° C. The film was developed by standard procedures. Virus from the positive wells which contained the recombinant virus was further purified.

SELECTION OF G418 RESISTANT IBR VIRUS. The antibiotic G418 (GIBCO) has a wide range of inhibitory activity on protein synthesis. However, recombinant viruses expressing the aminoglycosidase 3'-phosphotransferase, encoded by the NEO gene of the transposable element Tn5, are resistant to G418. The transfection stocks of recombinant viruses were grown on MDBK cells in the presence of 500 µg/ml G418 in complete DME medium plus 1% fetal bovine serum. After one or two days at 37° C., plaques from the dishes inoculated with the highest dilution of virus were picked for virus stocks. The selection was repeated a second or third time. The virus stocks generated from the G418 selection were tested for NEO gene insertion by the SOUTHERN BLOTTING OF DNA hybridization procedure described above.

CONSTRUCTION OF DELETION VIRUSES. The strategy used to construct deletion viruses involved the use of both homologous recombination and direct ligation techniques. Initially a virus was constructed via homologous recombination, in which the gene to be deleted was replaced with the E. coli β-galactosidase marker gene. A second virus was then constructed in which the marker gene was deleted either by homologous recombination or via direct ligation. The advantage of this strategy is that both viruses may be purified by the BLUOGAL SCREEN FOR RECOMBINANT HERPESVIRUS. The first virus is purified by picking blue plaques from a white plaque background, the second virus is purified by picking white plaques from a blue plaque background. Several homology vectors were constructed for the purpose of deleting the gpG and gpE gene coding regions. A detailed description of these homology vectors follows.

Figure 7A:
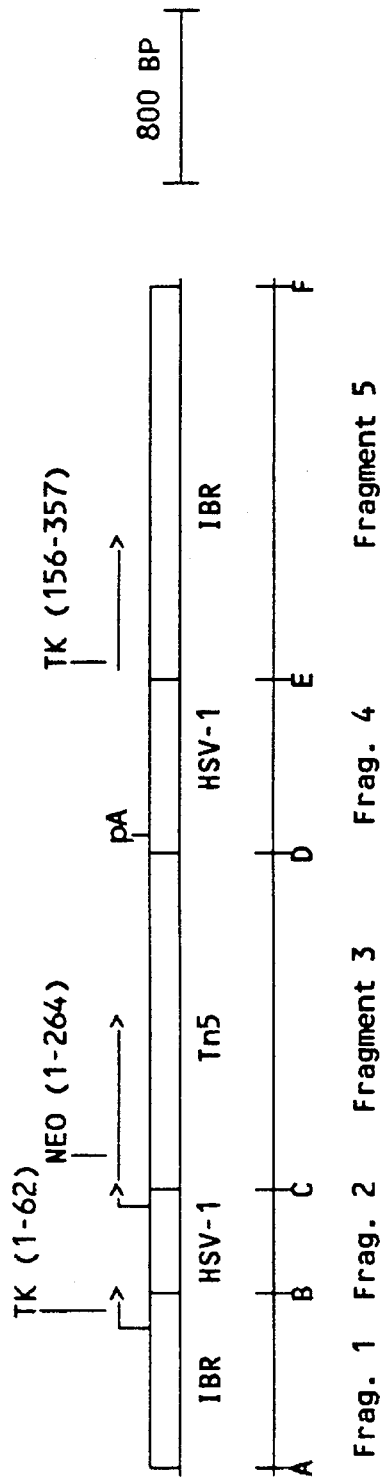
FIG. 7 SEQ ID NO: 10–15 Detailed description of the DNA insertion in Homology Vector 129-71.5. Diagram showing the orientation of DNA fragments assembled in plasmid 129-71.5. The origin of each fragment is indicated in the table. The sequences (SEQ ID NOS: 10–15) located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: polyadenylation signal (pA), infectious bovine rhinotracheitis virus (IBR), Herpes simplex virus type 1 (HSV-1), thymidine kinase (TK), neomycin resistance (NEO), bacterial transposon Tn5 (Tn5).
Figure 7B:
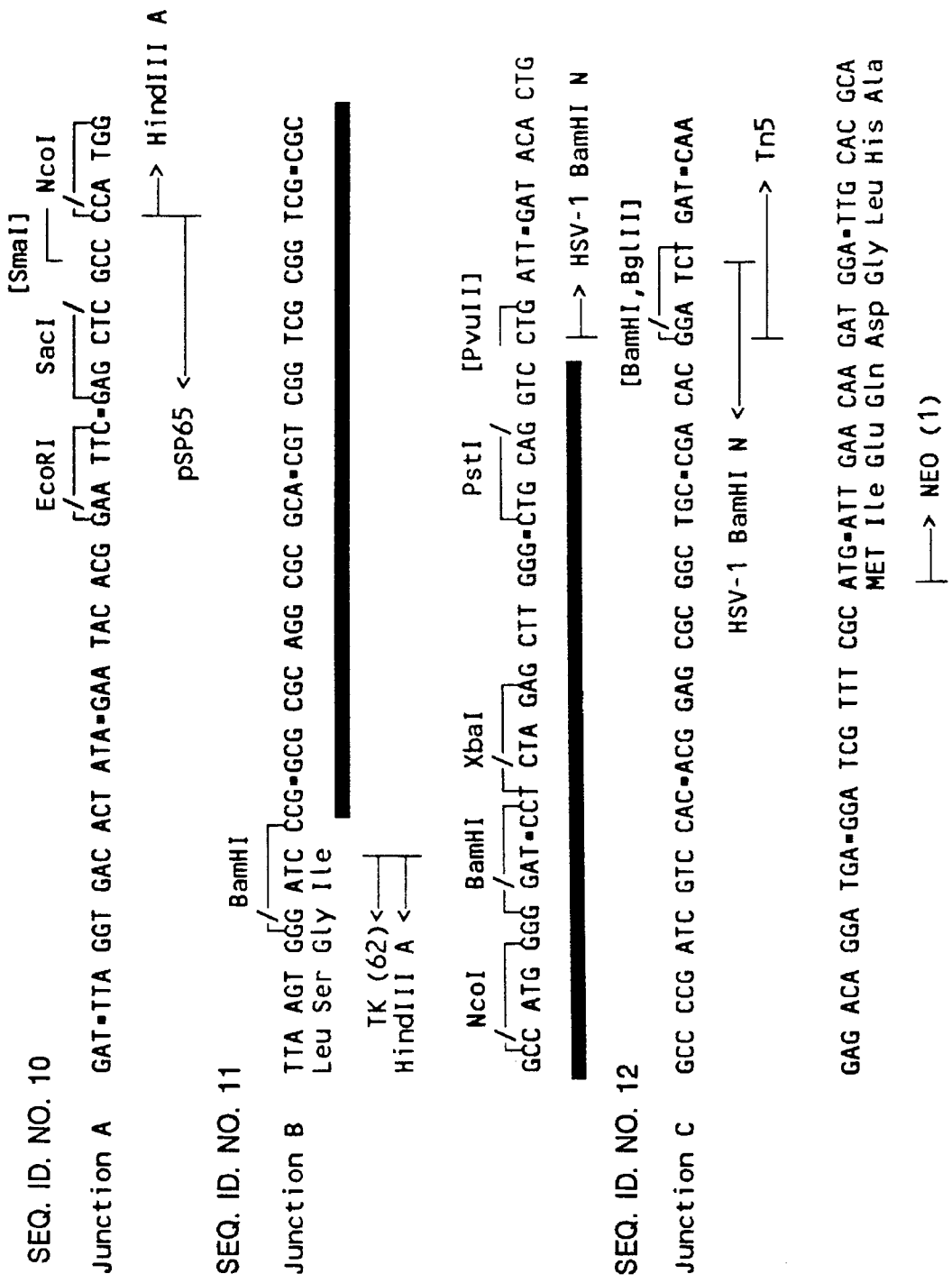

HOMOLOGY VECTOR 129-71.5. The plasmid 129-71.5 was constructed for the purpose of deleting a portion of the TK gene coding region from the IBR virus. It incorporates a selectable marker, the bacterial transposon neomycin resistance gene, flanked by IBR virus DNA. Upstream of the marker gene is an approximately 860 base pair fragment of IBR virus DNA which ends with sequences encoding amino acids 1–62 of the TK primary translation product. Downstream of the marker gene is an approximately 1741 base pair fragment of IBR virus DNA which begins with sequences encoding amino acids 156–367 of the TK primary translation product. When this plasmid is used according to the HOMOLOGOUS RECOMBINATION PROCEDURE FOR GENERATING RECOMBINANT HERPESVIRUS, it will replace the DNA coding for amino acids 63–155 of the TK primary translation product with DNA coding for the marker gene. Note that the marker gene will be under the control of the herpes simplex type 1 alpha-4 immediate early gene promoter (5). A detailed description of the plasmid is given in FIG. 7. It was constructed from the indicated DNA sources utilizing standard recombinant DNA techniques (6). It may be constructed by joining restriction fragments from the following sources with the synthetic DNA sequences indicated in FIG. 7. The plasmid vector is derived from an approximately 2975 base pair SmaI to HindIII restriction fragment of pSP65 (Promega). Fragment 1 is an approximately 860 base pair NcoI to BamHI restriction fragment of the IBR virus HindIII restriction fragment A (7). This fragment is located on an approximately 5500 base pair ClaI to NruI fragment contained in the IBR virus HindIII A fragment. Fragment 2 is an approximately 490 base pair PvuII to BamHI restriction sub-fragment of the HSV-1 BamHI restriction fragment N (5). Note that the HSV-1 oriS region has been removed from this fragment by deletion of the sequences between the SmaI sites located 1483 and 128 base pairs away from the PvuII end (10) Fragment 3 is an approximately 1541 base pair BglII to BamHI restriction fragment of plasmid pNEO (P. L. Biochemicals, Inc.). Fragment 4 is an approximately 784 base pair SmaI to SmaI restriction sub-fragment of the HSV-1 BamHI restriction fragment Q (10). Note that this fragment is oriented such that the polyadenylation sequence (AATAAA) is located closest to junction D. Fragment 5 is an approximately 1741 base pair BglII to StuI restriction sub-fragment from the IBR HindIII restriction fragment A (7).

Figure 11A:
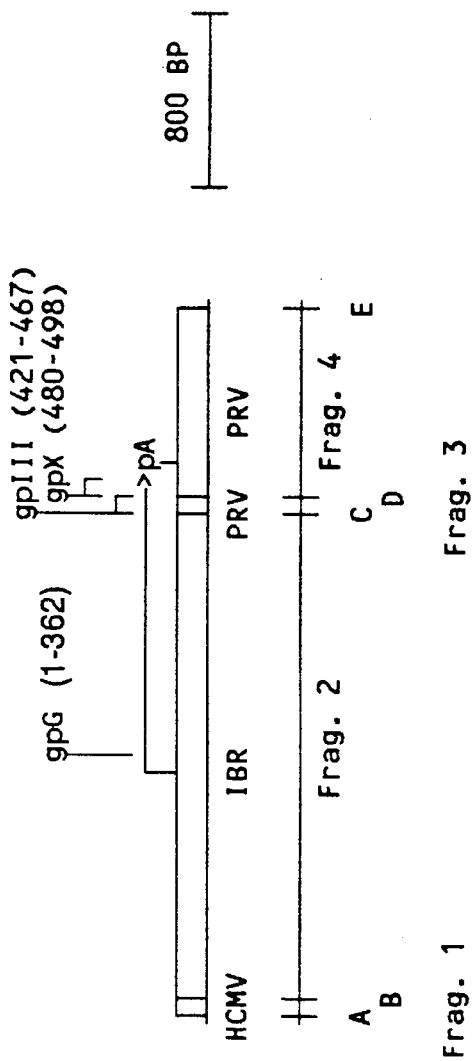
FIG. 11 SEQ ID NOS: 20–25 Detailed description of the DNA insertion in Plasmid 459-12.6. Diagram showing the orientation of DNA fragments assembled in plasmid 459-12.6. The origin of each fragment is indicated in the table. The sequences (SEQ ID NOS: 20–25) located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: unique glycoprotein G (gpG), glycoprotein III (gpIII), glycoprotein X (gpX), polyadenylation signal (pA), infectious bovine rhinotracheitis virus (IBR), pseudorabies virus (PRV), and human cytomegalovirus (HCMV).

PLASMID 459-12.6. The plasmid 459-12.6 was generated for the purpose of constructing a recombinant cloning vector which expresses the IBR virus glycoprotein G. This was accomplished by inserting the IBR virus gpG gene into S-PRV-013 (U.S. Ser. No. 06/823,102, filed Jan. 27, 1986). Plasmid 459-12.6 contains a chimeric gene under the control of the IBR virus gpG promoter. The chimeric gene expresses a fusion protein consisting of the first 362 amino acids of IBR virus gpG fused to amino acids 421–467 of the PRV gpIII (13) followed by amino acids 480–498 of the PRV gpX (12). The chimeric gene is flanked by HindIII restriction sites. When this plasmid is used with S-PRV-013 and the restriction enzyme HindIII according to the DIRECT LIGATION PROCEDURE FOR GENERATING RECOMBINANT HERPESVIRUS the resulting recombinant will express the IBR virus gpG. A detailed description of the plasmid is given in FIG. 11. It was constructed from the indicated DNA sources utilizing standard recombinant DNA techniques (6). It may be constructed by joining restriction fragments from the following sources with the synthetic DNA sequences indicated in FIG. 11. The plasmid vector is derived from an approximately 2999 base pair XbaI to XbaI restriction fragment of a hybrid cloning vector derived from pSP64 and pSP65 (Promega). The hybrid cloning vector was constructed by joining the approximately 1369 base pair PvuI to SmaI fragment from pSP64 with the approximately 1652 base pair PvuI to SmaI fragment from pSP65. Fragment 1 is an approximately 182 base pair PstI to EcoRV restriction sub-fragment of the HCMV XbaI restriction fragment B (16). Fragment 2 is an approximately 2121 base pair MluI to XhoI restriction sub-fragment of the IBR virus HindIII restriction fragment K (7). Fragment 3 is an approximately 121 base pair XhoI to BamHI restriction sub-fragment of the PRV BamHI restriction fragment #2 (3). Fragment 4 is an approximately 760 base pair NdeI to SalI restriction subfragment of the PRV BamHI restriction fragment #7 (3).

Figure 12C:
FIG. 12 SEQ ID NO: 26–32 Detailed description of the DNA insertion in Homology Vector 439-01.31. Diagram showing the orientation of DNA fragments assembled in plasmid 439-01.31. The origin of each fragment is indicated in the table. The sequences (SEQ ID NOS: 26,27, 29–32 located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: unique short 2 (US2), glycoprotein G (gpG), glycoprotein IV (gpIV), polyadenylation signal (pA), infectious bovine rhinotracheitis virus (IBR), pseudorabies virus (PRV), and human cytomegalovirus (HCMV).
Figure 12D:
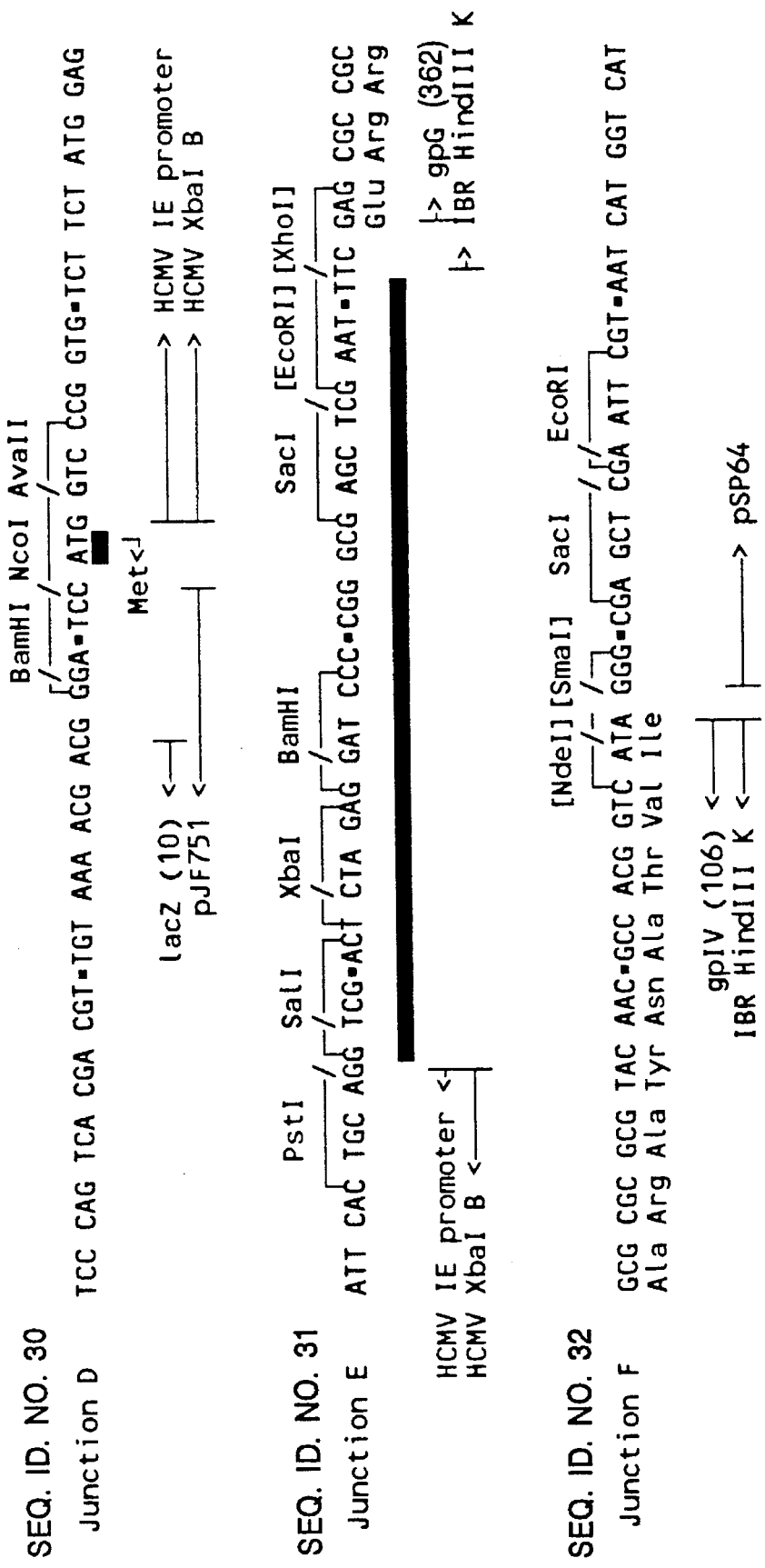

HOMOLOGY VECTOR 439-01.31. The plasmid 439-01.31 was constructed for the purpose of deleting a portion of the gpG gene coding region from the IBR virus. It incorporates an *E. coli* β-galactosidase marker gene flanked by IBR virus DNA. Downstream of the marker gene is an approximately 3593 base pair fragment of IBR virus DNA which ends with sequences encoding the first 262 amino acids of the gpG primary translation product. Upstream of the marker gene is an approximately 785 base pair fragment of IBR virus DNA which begins with sequences encoding the last 80 amino acids of the gpG primary translation product. When this plasmid is used according to the HOMOLOGOUS RECOMBINATION PROCEDURE FOR GENERATING RECOMBINANT HERPESVIRUS it will replace the DNA coding for amino acids 263–361 of the gpG primary translation product with DNA coding for the marker gene. Note that the β-galactosidase (lacZ) marker gene will be under the control of the human cytomegalovirus immediate early gene promoter. A detailed description of the plasmid is given in FIG. 12. It was constructed from the indicated DNA sources utilizing standard recombinant DNA techniques (6). It may be constructed by joining restriction fragments from the following sources with the synthetic DNA sequences indicated in FIG. 12. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 753 base pair SalI to NdeI restriction fragment of the PRV BamHI restriction fragment #7 (3). Note that this fragment was resected with Exonuclease III/S1 nuclease digestion such that approximately 57 base pairs were removed from the NdeI end. Fragment 3 is an approximately 3347 base pair BalI to BamHI restriction fragment of plasmid pJF751 (38). Fragment 4 is an approximately 1191 base pair AvaI to PstI restriction fragment from the HCMV XbaI restriction fragment E (16). Fragment 5 is an approximately 785 base pair XhoI to NdeI restriction fragment from the IBR HindIII restriction fragment K (7). Note that the lacZ marker gene is flanked by XbaI sites located at Junction B and Junction E in this plasmid permitting the marker gene to be cut out with XbaI.

Figure 13A:
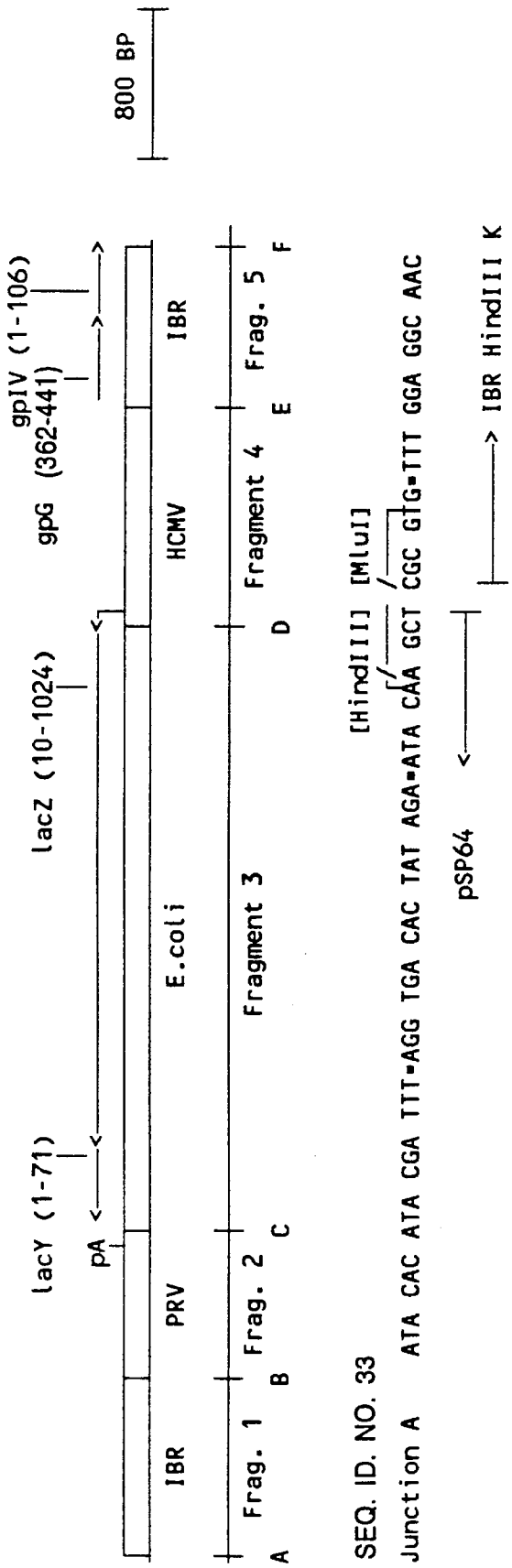
FIG. 13 SEQ ID NOS: 29–32, 33 & 34 Detailed description of the DNA insertion in Homology Vector 439-21.69. Diagram showing the orientation of DNA fragments assembled in plasmid 439-21.69. The origin of each fragment is indicated in the table. The sequences SEQ ID. NOS. 29–33 & 34 located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: unique short 2 (US2), glycoprotein G (gpG), glycoprotein IV (gpIV), polyadenylation signal (pA), infectious bovine rhinotracheitis virus (IBR), pseudorabies virus (PRV), and human cytomegalovirus (HCMV).
Figure 13B:
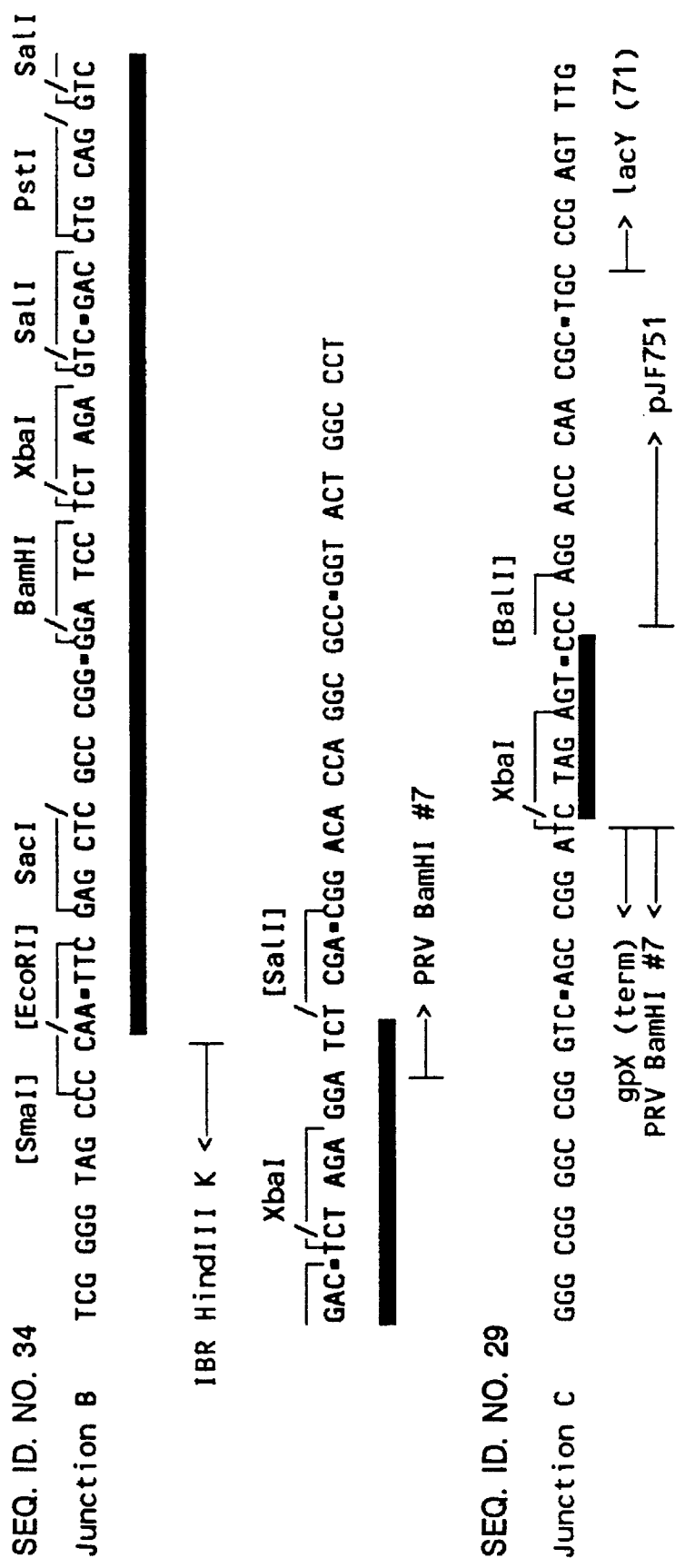

HOMOLOGY VECTOR 439-21.69. The plasmid 439-21.69 was constructed for the purpose of deleting a portion of the gpG gene coding region from the IBR virus. It incorporates an *E. coli* β-galactosidase (lacZ) marker gene flanked by IBR virus DNA. Downstream of the marker gene is an approximately 888 base pair fragment of IBR virus DNA which begins approximately 1042 base pairs upstream of the initiation codon of the gpG gene and ends approximately 154 base pairs upstream of the initiation codon of the gpG gene. Upstream of the marker gene is an approximately 785 base pair fragment of IBR virus DNA which begins with sequences encoding the last 80 amino acids of the gpG primary translation product. When this plasmid is used according to the HOMOLOGOUS RECOMBINATION PROCEDURE FOR GENERATING RECOMBINANT HERPESVIRUS it will replace the DNA coding for amino acids 1-361 of the gpG primary translation product with DNA coding for the marker gene. Note that the β-galactosidase (lacZ) marker gene will be under the control of the human cytomegalovirus immediate early gene promoter. A detailed description of the plasmid is given in FIG. 13. It was constructed from the indicated DNA sources utilizing standard recombinant DNA techniques (6). It may be constructed by joining restriction fragments from the following sources with the synthetic DNA sequences indicated in FIG. 13. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 753 base pair SalI to NdeI restriction fragment of the PRV BamHI restriction fragment #7 (3). Note that this fragment was resected with Exonuclease III/S1 nuclease digestion such that approximately 57 base pairs were removed from the NdeI end. Fragment 3 is an approximately 3347 base pair BalI to BamHI restriction fragment of plasmid pJF751 (38). Fragment 4 is an approximately 1191 base pair AvaI to PstI restriction fragment from the HCMV XbaI restriction fragment E (16). Fragment 5 is an approximately 785 base pair XhoI to NdeI restriction fragment from the IBR HindIII restriction fragment K (7). Note that the lacZ marker gene is flanked by XbaI sites located at Junction B and Junction E in this plasmid permiting the marker gene to be cut out with XbaI.

HOMOLOGY VECTOR 439-70.4. The plasmid 439-70.4 was constructed for the purpose of deleting the *E. coli* β-galactosidase (lacZ) marker gene from S-IBR-035 virus. It incorporates two regions of IBR virus DNA which flanks the marker gene in S-IBR-035. The first region is an approximately 888 base pair fragment of IBR virus DNA which begins approximately 1042 base pairs upstream of the initiation codon of the gpG gene and ends approximately 154 base pairs upstream of the initiation codon of the gpG gene. The second region is an approximately 785 base pair fragment of IBR virus DNA which begins with sequences encoding the last 80 amino acids of the gpG primary translation product. When this plasmid is used in conjunction with S-IBR-035 DNA according to the HOMOLOGOUS RECOMBINATION PROCEDURE FOR GENERATING RECOMBINANT HERPESVIRUS it will delete the DNA coding for the *E. coli* β-galactosidase (lacZ) marker gene. A detailed description of the plasmid is given in FIG.

Figure 14A:
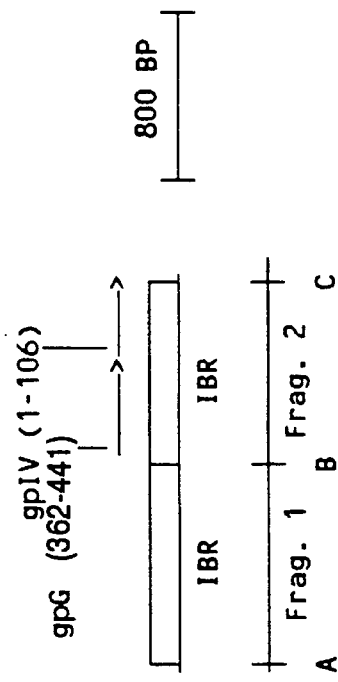
FIG. 14 Detailed description of the DNA insertion in Homology Vector 439-70.4. Diagram showing the orientation of DNA fragments assembled in plasmid 439-70.4. The origin of each fragment is indicated in the table. The sequences (SEQ ID NOS: 32, 33 and 35) located at each of the junctions between fragments is also shown. The restriction sites used to generated each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: glycoprotein G (gpG), glycoprotein IV (gpIV) infectious bovine rhinotracheitis virus (IBR).

14. It was constructed from the indicated DNA sources utilizing standard recombinant DNA techniques (6). It may be constructed by joining restriction fragments from the following sources with the synthetic DNA sequences indicated in FIG. 14. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 785 base pair XhoI to NdeI restriction fragment from the IBR HindIII restriction fragment K (7).

Figure 17A:
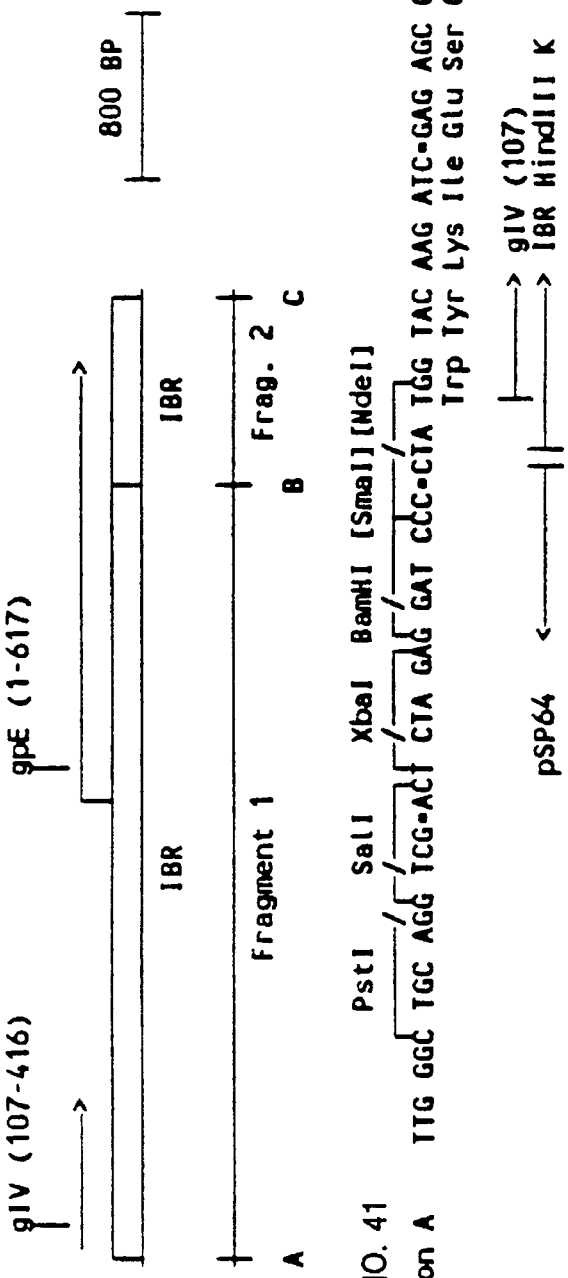
FIG. 17 SEQ ID NOS: 41–43 Detailed description of a plasmid containing the gpE gene. Diagram showing the orientation of DNA fragments to be assembled in the gpE containing plasmid. The origin of each fragment is indicated in the table. The sequences SEQ ID NOS: 41–43 located at each of the junctions between fragments are also shown. The restriction sites used to generate each fragment are described for each junction. The location of several gene coding regions and regulatory elements is also given. The following two conventions are used: numbers in parentheses, (), refer to amino acids, and restriction sites in brackets, [], indicate the remnants of sites which were destroyed during construction. The following abbreviations are used: unique glycoprotein E (gpE), glycoprotein IV (gIV), and infectious bovine rhinotracheitis virus (IBR).

IBR VIRUS gpE PLASMID. A plasmid may be generated for the purpose of constructing a recombinant cloning vector which expresses the IBR virus glycoprotein E. This plasmid may be used to insert the IBR virus gpE gene into S-PRV-002 (U.S. Pat. No. 4,877,737). The plasmid will contain the gpE gene flanked by XbaI restriction sites. When this plasmid is used with S-PRV-002 and the restriction enzyme XbaI according to the DIRECT LIGATION PROCEDURE FOR GENERATING RECOMBINANT HERPESVIRUS the resulting recombinant will express the IBR virus gpE. A detailed description of the plasmid is given in FIG. 17. It may be constructed, utilizing standard recombinant DNA techniques (6), by joining restriction fragments from the following sources. The plasmid vector is derived from an approximately 2999 base pair XbaI to XbaI restriction fragment of a hybrid cloning vector derived from pSP64 and pSP65 (Promega). The hybrid cloning vector was constructed by joining an approximately 1369 base pair PvuI to SmaI fragment from pSP64 with the approximately 1652 base pair PvuI to SmaI fragment from pSP65. Fragment 1 is an approximately 3647 base pair NdeI to HindIII restriction sub-fragment of the IBR virus HindIII restriction fragment K (7). Fragment 2 is an approximately 832 base pair HindIII to SacI restriction sub-fragment of an IBR virus 2400 base pair SmaI restriction fragment. This SmaI fragment has been cloned into the SmaI site of the plasmid pSP64 (Promega). This plasmid is designated PSY1645. PSY1645 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68650. Note that the lacZ marker gene is flanked by XbaI sites located at Junction B and Junction E in this plasmid permitting the marker gene to be cut out with XbaI.

Figure 18C:
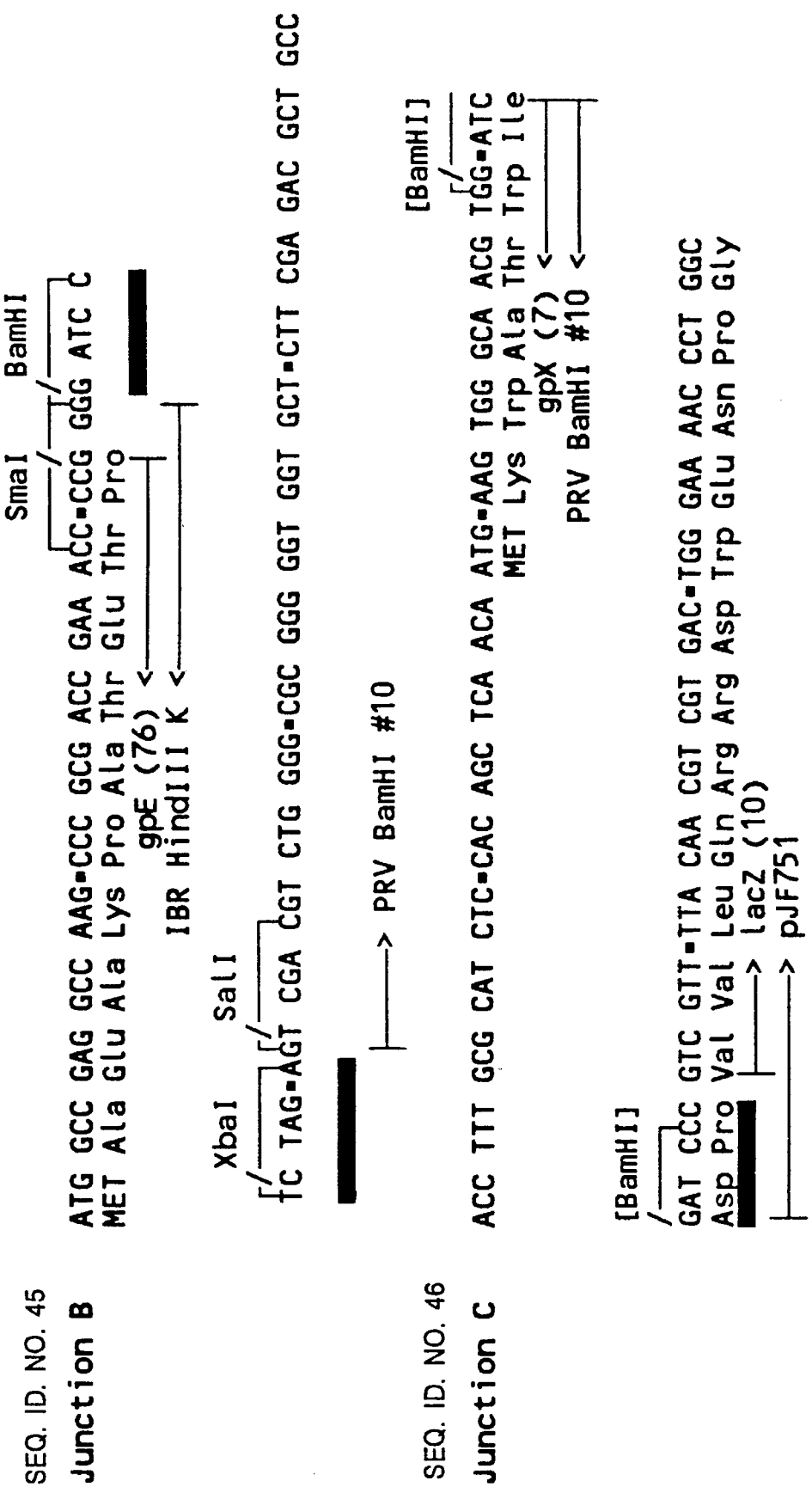
FIG. 18 SEQ ID NOS: 44–48 Detailed description of the DNA insertion in the homology vector 536-03.5. Diagram showing the orientation of DNA fragments to be assembled in the homology vector. The origin of each fragment is indicated in the table.
Figure 18E:

HOMOLOGY VECTOR 536-03.5. The plasmid 536-03.5 was constructed for the purpose of deleting a portion of the gpE gene coding region from the IBR virus. It incorporates an *E. coli* β-galactosidase (lacZ) marker gene flanked by IBR virus DNA. Upstream of the marker gene is an approximately 1704 base pair fragment of IBR virus DNA which ends with sequences encoding amino acids 1–76 of the gpE primary translation product. Downstream of the marker gene is an approximately 742 base pair fragment of IBR virus DNA which begins with sequences encoding amino acids 548–617 of the gpE primary translation product. When this plasmid is used according to the HOMOLOGOUS RECOMBINATION PROCEDURE FOR GENERATING RECOMBINANT HERPESVIRUS, it will replace the DNA coding for amino acids 77–547 of the gpE primary translation product with DNA coding for the marker gene. Note that the β-galactosidase (lacZ) marker gene will be under the control of the PRV gpX. A detailed description of the plasmid is given in FIG. 18. It may be constructed utilizing standard recombinant DNA techniques (6), by joining restriction fragments from the following sources with the synthetic DNA sequences indicated in FIG. 18. The plasmid vector is derived from an approximately 2975 base pair SmaI to HindIII restriction fragment of pSP65 (Promega). Fragment 1 is an approximately 1704 base pair SmaI to SmaI restriction sub-fragment of the IBR HindIII restriction fragment K (7). Fragment 2 is an approximately 413 base pair SalI to BamHI restriction sub-fragment of the PRV BamHI restriction fragment 10 (3). Fragment 3 is an approximately 3010 base pair BamHI to PvuII restriction fragment of plasmid pJF751 (38). Fragment 4 is an approximately 754 base pair NdeI to SalI restriction sub-fragment of the PRV BamHI restriction fragment #7 (3). Fragment 5 is an approximately 742 base pair NheI to BglI sub-fragment of an IBR virus 2400 base pair SmaI fragment. This SmaI fragment has been cloned into the SmaI site of the plasmid pSP64 (Promega). This plasmid is designated PSY1645. PSY1645 has been deposited with the American Type Culture Collection. Note that the lacZ marker gene is flanked by XbaI sites located at Junction B and Junction E in this plasmid permitting the marker gene to be cut out with XbaI.

VACCINATION STUDIES IN CALVES WITH INACTIVATED IBR VIRUS.

Calves, seronegative to IBR virus, were housed in facilities secure from IBR virus exposure. Groups of four calves were vaccinated intramuscularly with vaccines containing $10^{7.3}$ or $10^{8.0}$ plaque forming units of inactivated IBR virus formulated with an oil adjuvant. A second vaccination was given 21 days later; four calves were maintained as unvaccinated controls. At 21 days after the second vaccination, animals were challenged intranasally with virulent wild-type IBR virus. After vaccination and challenge, animals were observed and the injection site was palpated weekly. Blood samples were taken on days 0, 7, 21, 28, and 42 post vaccination. After challenge, animals were observed daily for clinical signs of IBR. Blood samples were taken on days 7 and 13 post challenge. Nasal swabs were collected on days 3, 6, 9, and 12 post challenge.

PURIFICATION OF IBR VIRUS gpG. gpG was purified from the tissue culture medium of infected MDBK cells. Confluent MDBK cells in serum-free medium were infected at a multiplicity of infection equal to 5, with wild-type, Cooper strain of IBR virus. The cells and media were harvested at approximately twenty-two hours after infection, when the cells showed considerable cytopathic effect and the fluids were centrifuged at 5000 rpm for 15 minutes.

The supernatant fluid was concentrated approximately 10-fold by ultrafiltration through an Amiconym-30 membrane, and dialyzed against 10 mM NaPO$_4$ pH 7.2. The dialysate was treated for 20 minutes at 0° C. with 70% perchloric acid to a final concentration of 0.2M perchloric acid, then centrifuged at 12,000 rpm for 20 minutes. The supernatant fluid was then dialyzed against 20 mM Tris pH 9.5.

The acid-soluble proteins were separated by column chromatography on a DEAE-Sephacel anion exchange column using a liner gradient elution: 0 to 100% A to B where A=20 mM Tris pH 9.5 and B=20 mM Tris pH 9.5/800 mM NaCl. The gpG eluted at approximately 35–40% B. Peak fractions were assayed by Western blot using anti gpG peptide sera. Reactive fractions were combined and dialyzed against 5 mM Tris pH 7.0. The sample was then concentrated 10-fold by lyophilization and stored at −20° C.

ELISA ASSAY. A standard enzyme-linked immunosorbent assay (ELISA) protocol was used to determine the immune status of cattle following vaccination and challenge.

A purified gpG antigen solution (100 µl at 1 ng/µl in PBS) was allowed to absorb to the wells of microtiter dishes for 18 hours at 4° C. The coated wells were rinsed one time with PBS. Wells were blocked by adding 250 μl of PBS containing 1% BSA (Sigma) and incubating 1 hour at 37° C. The blocked wells were rinsed one time with PBS containing 0.02% Tween 20. 50 μl of test serum (previously diluted 1:2 in PBS containing 1% BSA) were added to the wells and incubated 1 hour at 37° C. The antiserum was removed and the wells were washed 3 times with PBS containing 0.02% Tween 20. 50 μl of a solution containing anti-bovine IgG coupled to horseradish peroxidase (diluted 1:500 in PBS containing 1% BSA, Kirkegaard and Perry Laboratories, Inc.) was added to visualize the wells containing antibody against the specific antigen. The solution was incubated 1 hour at 37° C., then removed and the wells were washed 3 times with PBS containing 0.02% Tween 20. 100 μl of substrate solution (ATBS, Kirkegaard and Perry Laboratories, Inc.) were added to each well and color was allowed to develop for 15 minutes. The reaction was terminated by addition of 0.1M oxalic acid. The color was read at absorbance 410 nm on an automatic plate reader.

PROCEDURE FOR GENERATING MONOCLONAL ANTIBODIES. To produce monoclonal antibodies, 8 to 10 week old BALB/c female mice were vaccinated intraperitoneally seven times at two to four week intervals with $10^7$ PFU of S-PRV-160. Three weeks after the last vaccination, mice were injected intraperitoneally with 40 μg of purified gpG. Spleens were removed from the mice three days after the last antigen dose.

Splenocytes were fused with mouse NS1/Ag4 plasmacytoma cells by the procedure modified from Oi and Herzenberg (39). Splenocytes and plasmacytoma cells were pelleted together by centrifugation at 300×g for 10 minutes. One ml of a 50% solution of polyethylene glycol (m. w. 1300–1600) was added to the cell pellet with stirring over one minute. Dulbecco's modified Eagles's medium (5 ml) was added to the cells over three minutes. Cells were pelleted by centrifugation at 300×g for 10 minutes and resuspended in medium with 10% fetal bovine serum and containing 100 μM hypoxanthine, 0.4 μM aminopterin and 16 μM thymidine (HAT). Cells (100 μl) were added to the wells of eight to ten 96-well tissue culture plates containing 100 μl of normal spleen feeder layer cells and incubated at 37° C. Cells were fed with fresh HAT medium every three to four days.

Hybridoma culture supernatants were tested by the ELISA ASSAY in 96-well microtiter plates coated with 100 ng of purified gpG. Supernatants from reactive hybridomas were further analyzed by black-plaque assay and by Western Blot. Selected hybridomas were cloned twice by limiting dilution. Ascitic fluid was produced by intraperitoneal injection of $5\times10^6$ hybridoma cells into pristane-treated BALB/c mice.

METHOD FOR cDNA CLONING BOVINE ROTAVIRUS gp38 GENE. The Calf Nebraska strain of bovine rotavirus (USDA) was propagated on MA-104 cells (Rhesus monkey kidney cells from MABioproducts). Confluent monolayers were infected at a multiplicity of infection of greater than 10 in DMEM containing 5 micrograms/ml trypsin. Cells were incubated with virus for 48 hours or until a cytopathic effect was obtained. Media and cell debris were collected and centrifuged at 10,000×g for 20 minutes at 4° C. The supernatant containing the rotavirus was then centrifuged at 10,000×g in a preparative Beckman Ti45 rotor at 4° C. Virus pellets were resuspended in SM medium (50 mM Tris-HCl pH 7.5, 100 mM KCl, 10 mM $MgCl_2$) and homogenized lightly in a Dounce-type homogenizer. The resuspended virus was centrifuged at 10,000×g for 10 minutes then loaded onto 25–50% CsCl gradients in SM buffer. Gradients were centrifuged at 100,000×g for 4 hours at 20° C. The two blue-white bands representing intact virions and cores of rotavirus were collected, diluted, and the CsCl gradient procedure was repeated a second time. Virus obtained from the second gradient was dialyzed overnight against SM buffer at 4° C.

Dialyzed bovine rotavirus was twice extracted with an equal volume of SDS/phenol, then twice more with chloroform: isoamylalcohol (24:1). The double stranded RNA was precipitated with ethanol in the presence of 0.2 M sodium acetate, centrifuged and resuspended in water. The yield was typically 100 micrograms from 1,000 $cm^2$ of infected cells.

160 micrograms of double-stranded bovine rotavirus RNA obtained from the above procedure was mixed with one microgram each of two synthetic oligonucleotide primers in a volume of 160 microliter (sequences of primers were: 5'-GGGAATTCTGCAGGTCACATCATACAATTCTAATCTAAG-3' (SEQ ID NO: 50) and 5'-GGGAATTCTGCAGGCTTTAAAAGAGAGAATTTCCGTTTGGCTA-3') (SEQ ID NO: 51) derived from the published sequence of bovine rotavirus (40). The RNA-primer mixture was boiled for 3 minutes in a water bath then chilled on ice. Additions of 25 microliters of 1M Tris-HCl pH 8.3, 35 microliters of 1M KCl, 10 microliters of 0.25M $MgCl_2$, 7 microliters of 0.7M 2-mercaptoethanol, 7 microliters of 20 mM dNTP's, and 6 microliters of reverse transcriptase (100 units) were made sequentially. The reaction was incubated at 42° C. for 1.5 hours then 10 microliters of 0.5M EDTA pH 8.0 was added and the solution was extracted once with chloroform:phenol (1:1). The aqueous layer was removed and to it 250 microliters of 4M ammonium acetate and 1.0 ml of 95% ethanol was added, the mixture was frozen in dry ice and centrifuged in the cold. The resulting pellet was resuspended in 100 microliters of 10 mM Tris-HCl pH 7.5 and the ammonium acetate precipitation procedure was repeated. The pellet was resuspended in 100 microliters of 0.3M KOH and incubated at room temperature overnight, then at 37° C. for 2 hours. The solution was brought to neutral pH by addition of 10 microliters of 3.0M HCl and 25 microliters of 1.0M Tris-HCl pH 7.5. The resulting single-stranded cDNA was then precipitated two times by the above-described ammonium acetate-ethanol procedure. The pellet obtained was resuspended in 50 microliters of 10 mM Tris-HCl pH 7.5, 100 mM NaCl, 1 mM EDTA, boiled in a water bath for 2 minutes, then incubated at 59° C. for 16 hours. The solution was lyophilized to a volume of 15 microliters and the resulting double-stranded cDNA was run on a 1.0% agarose gel (Sigma agarose Type II). The ethidium bromide-stained DNA migrating at 1,000–1,100 base pair length was excised from the gel and electroeluted in a CBS electroeluter device. The solution was lyophilized, and the cDNA was resuspended in 25 microliters of water. To this solution was added 2 microliters of 1.0M Tris-HCl pH 7.5, 2 microliters of 1M KCl, 1 microliter of 0.25M $MgCl_2$, microliter of 20 mM dNTP's and 5 units of *E. coli* DNA polymerase I. The reaction was incubated at room temperature for 15 minutes, then chloroform/phenol extracted and ammonium acetate-ethanol precipitated as described above. The resulting cDNA was tailed with dCTP using terminal deoxynucleotide transferase (BRL buffer and enzyme used). The reaction was stopped with 2 microliters of 0.5M EDTA, chloroform/phenol extracted and precipitated with sodium acetate in the presence of 10 micrograms of carrier tRNA. The resuspended cDNA was mixed with 200 ng of dGMP-tailed Pst I cut pBR322 (BRL catalog #5355SA) in 200 microliters of 10 mM Tris-HCl pH 7.5, 100 mM NaCl, 1 mM EDTA, heated to 65° C. for 5 minutes, then 57° C. for 2 hours. The annealed cDNA-vector pBR322 was transformed onto *E. coli* DH-1 cells prepared for high efficiency transformation. Colonies that showed sensitivity to ampicillin and tetracycline resistance were grown and DNA was prepared and cut with Pst I to determine the size of the cDNA insert. Several clones having Pst I inserts of 1,050–1,100 base pairs were analyzed and found to have identical restriction enzyme digest patterns. For one of these clones, the 1,100 base pair Pst I insert was subcloned into a M13 phage sequencing vector. Part of the DNA sequence of this clone was determined and was found to be identical to the published sequence (40).

cDNA CLONING. cDNA cloning refers to the methods used to convert RNA molecules into DNA molecules following state of the art procedures. Applicants' methods are described in Gubler and Hoffman (23). Bethesda Research Laboratories (Gaithersburg, Md.) have designed a cDNA Cloning Kit that is very similar to the procedures used by applicants and contains the best set of reagents and protocols to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4M guanidine thiocyanate, 0.1% antifoam A, 25 mMsodium citrate pH 7.0, 0.5% N-lauroyl sarcosine, 0.1M beta-mercaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7M CsCl, 25 mM sodium citrate pH 7.0) in a Beckman SW41 centrifuge tube. The samples were centrifuged for 18 hours at 20° C. at 36,000 rpm in a Beckman SW41 rotor. The tubes were put on ice and the supernatants from the tubes were carefully removed by aspiration to leave the RNA pellet undisturbed. The pellet was resuspended in 400 microliters glass distilled water, and 2.6 mls of guanidine solution (7.5M guanidine-HCl, 25 mM sodium citrate pH 7.0, 5 mM dithiothreitol) were added. Then 0.37 volumes of 1M acetic acid were added, followed by 0.75 volumes of cold ethanol and the sample was put at −20° C. for 18 hours to precipitate RNA. The precipitate was collected by centrifugation in a Sorvall centrifuge for 10 min at 4° C. at 10,000 rpm in an SS34 rotor. The pellet was dissolved in 1.0 ml distilled water, recentrifuged at 13,000 rpm, and the supernatant saved. RNA was reextracted from the pellet 2 more times as above with 0.5 ml distilled water, and the supernatants were pooled. A 0.1 volume of 2M potassium acetate solution was added to the sample followed by 2 volumes of cold ethanol and the sample was put at −20° C. for 18 hours. The precipitated RNA was collected by centrifugation in the SS34 rotor at 4° C. for 10 minutes at 10,000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three milligrams of total RNA was boiled and chilled and applied to a 100 mg oligo-dT cellulose column in binding buffer (0.1M Tris pH 7.5, 0.5M LiCl, 5 mM EDTA pH 8.0, 0.1% lithium dodecyl sulfate). The retained poly-A$^+$RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mMsodium acetate and 2 volumes cold ethanol at −20° C. for 18 hours. The RNA was resuspended in 50 microliters distilled water.

Ten micrograms poly-A$^+$RNA was denatured in 20 mM methyl mercury hydroxide for 6 minutes at 22° C. Beta-mercaptoethanol was added to 75 mM and the sample was incubated for 5 min at 22° C. The reaction mixture for first strand cDNA synthesis in 0.25 ml contained 1 microgram oligo-dT primer (P-L Biochemicals) or 1 microgram synthetic primer, 28 units placental ribonuclease inhibitor (Bethesda Research Labs #5518SA), 100 mM Tris pH 8.3, 140 mM KCl, 10 mM MgCl$_2$, 0.8 mM dATP, dCTP, dGTP, and dTTP (Pharmacia), 100 microcuries $^{32}$p-labelled dCTP (New England Nuclear #NEG-013H), and 180 units AMV reverse transcriptase (Molecular Genetics Resources #MG 101). The reaction was incubated at 42° C. for 90 minutes, and then was terminated with 20 mM EDTA pH 8.0. The sample was extracted with an equal volume of phenol/chloroform (1:1) and precipitated with 2M ammonium acetate and 2 volumes of cold ethanol −20° C. for 3 hours. After precipitation and centrifugation, the pellet was dissolved in 100 microliters distilled water. The sample was loaded onto a 15 ml G-100 Sephadex column (Pharmacia) in buffer (100 mM Tris pH 7.5, 1 mM EDTA pH 8.90, 100 mM NaCl). The leading edge of the eluted DNA fractions were pooled, and DNA was concentrated by lyophilization until the volume was about 100 microliters, then the DNA was precipitated with ammonium acetate plus ethanol as above.

The entire first strand sample was used for second strand reaction which followed the Gubler and Hoffman (23) method except that 50 micrograms/ml dNTP's, 5.4 units DNA polymerase I (Boerhinger Mannheim #642–711), and 100 units/ml *E. coli* DNA ligase (New England Biolabs #205) in a total volume of 50 microliters were used. After second strand synthesis, the cDNA was phenol/chloroform extracted and precipitated. The DNA was resuspended in 10 microliters distilled water, treated with 1 microgram RNase A for 10 minutes at 22° C., and electrophoresed through a 1% agarose gel (Sigma Type II agarose) in 40 mM Tris-acetate buffer pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 microliters water.

Oligo-dC tails were added to the DNA to facilitate cloning. The reaction contained the DNA, 100 mM potassium cacodylate pH 7.2, 0.2 mM dithiothreitol, 2 mM CaCl$_2$, 80 micromoles dCTP, and 25 units terminal deoxynucleotidyl transferase (Molecular Genetic Resources #S1001) in 50 microliters. After 30 minutes at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 microliters of 0.01M Tris pH 7.5, 0.1M NaCl, 1 mM EDTA pH 8.0 at 65° C. for 2 minutes and then 57° C. for 2 hours. Fresh competent *E. coli* DH-1 cells were prepared and transformed as described by Hanahan (41) using half the annealed cDNA sample in twenty 200 microliter aliquots of cells. Transformed cells were plated on L-broth agar plates plus 10 micrograms/ml tetracycline. Colonies were screened for the presence of inserts into the ampicillin gene using Ampscreen (Bethesda Research Labs #5537 UA), and the positive colonies were picked for analysis.

POLYMERASE TILL-IN REACTION. DNA was resuspended in buffer containing 50 mM Tris pH 7.4, 50 mM KCl, 5 mM MgCl$_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

EXAMPLE

Example 1

S-IBR-002

Figure 2:
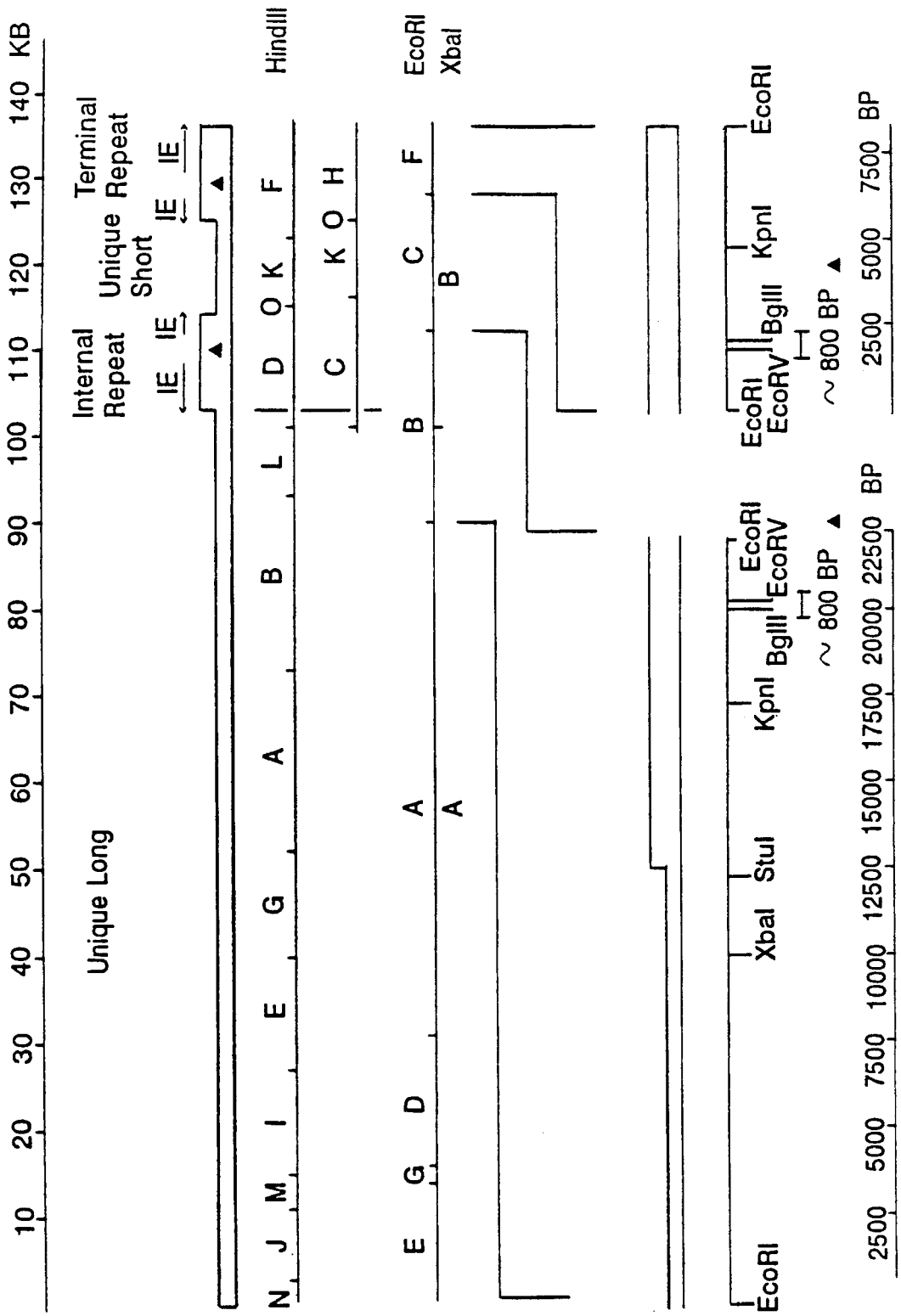
FIG. 2 Details of S-IBR-002. Diagram of S-IBR-002 genomic DNA showing the unique long, internal repeat, unique short, and Terminal repeat regions. Restriction maps for the enzymes HindIII, EcoRI, and XbaI are indicated (7). Fragments are lettered in order of decreasing size. The EcoRI B and F fragments are expanded for inclusion of more detail. The ~800 BP repeat deletions are indicated by deltas. Note that due to the inversion of the short region, which includes the unique short, internal, and terminal repeats, four half molar HindIII fragments are present (HindIII D, C, F, and H).

S-IBR-002 is an IBR virus that has a deletion of approximately 800 bp in the repeat region of the genome. This deletion removes the only two EcoRV restriction sites on the virus genome and an adjacent BglII site (FIG. 2).

To construct this virus, the DIRECT LIGATION PROCEDURE FOR GENERATING RECOMBINANT HERPESVIRUS was performed. Purified IBR virus DNA (Cooper strain) digested with EcoRV restriction enzyme was mixed with DraI-restriction enzyme-digested plasmid DNA containing the E.coli β-galactodidase (lacZ) gene under the control of the HSV-1 TK promoter. After ligation the mixture was used to transfect animal cells and the transfection stock was screened for recombinant IBR virus by the SOUTHERN BLOTTING OF DNA procedure. The final result of the purification was the recombinant IBR virus designated S-IBR-002. It was shown by Southern hybridization that this virus does not carry any foreign genes. Restriction enzyme analysis also showed that the insertion sites (EcoRV) in both repeats were deleted. FIG. 2 shows the restriction map of the EcoRI B fragment which contains the EcoRV restriction sites and the map of S-IBR-002 which lacks the EcoRV sites. S-IBR-002 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2140.

A study was conducted to determine the safety and serological response of young calves following intramuscular administration of S-IBR-002. These results are presented in Table 1. Three calves were inoculated intramuscularly with 10$^7$ PFU of S-IBR-002. Clinical signs of IBR and febrile response were absent in these calves, as well as in the contact control calf. All three calves developed significant neutralizing antibody to IBR virus but the contact control remained seronegative. These results suggest that S-IBR-002 is useful as a vaccine against IBR disease.

TABLE 1

Serologic and Clinical Response of
Young Calves Following Vaccination with S-IBR-002

| Virus Construct | Calf # | Clinical and Febrile response | Virus Isolation[a] | Antibody Titer Days Post Inoculation | | | | |
|---|---|---|---|---|---|---|---|---|
| | | | | 0 | 7 | 14 | 21 | 28 |
| S-IBR-002 | 28 | NONE | (−) | <2 | <4 | 6 | 5 | 3 |
| | 30 | NONE | (−) | <2 | <4 | 6 | <2 | 6 |
| | 94 | NONE | (−) | <2 | <4 | 6 | 3 | 8 |
| Control | 32 | NONE | (−) | <4 | <4 | <4 | <2 | <4 |

[a]From nasal swabs and peripheral blood leukocytes.

Example 2

Unique Short 2 gene

The unique short region of IBR virus contains a gene homologous to the US2 gene of several other herpesviruses. In the studies described below we show that deletion of the IBR unique short 2 gene (US2) may render the virus safe for use in pregnant cows, as determined by direct fetal inoculation.

Figure 1:
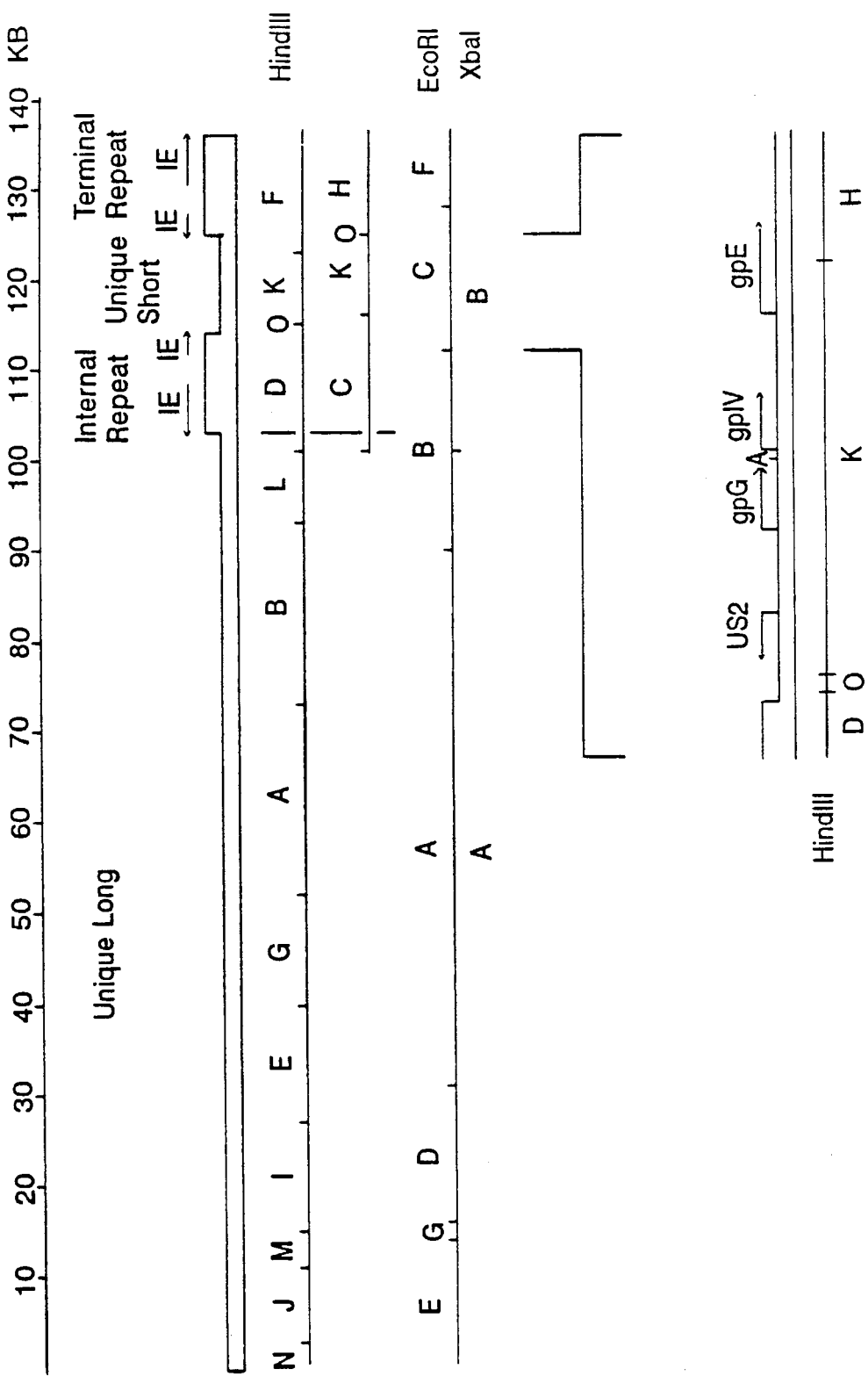
FIG. 1 Details of the IBR Cooper Strain. Diagram of IBR genomic DNA showing the unique long, internal repeat, unique short, and Terminal repeat regions. Restriction maps for the enzymes HindIII, EcoRI, and XbaI are indicated (7). Fragments are lettered in order of decreasing size. The unique short region is also expanded for inclusion of more detail. The location of several genes is also indicated, they are unique short 2 (US2), immediate early genes (IE) (20), glycoprotein G (gpG), glycoprotein IV (gpIV) (17), glycoprotein E (gpE). Note that due to the inversion of the short region, which includes the unique short, internal, and terminal repeats, four half molar HindIII fragments are present (HindIII D, C, F, and H).
Figures 4A, 4B:
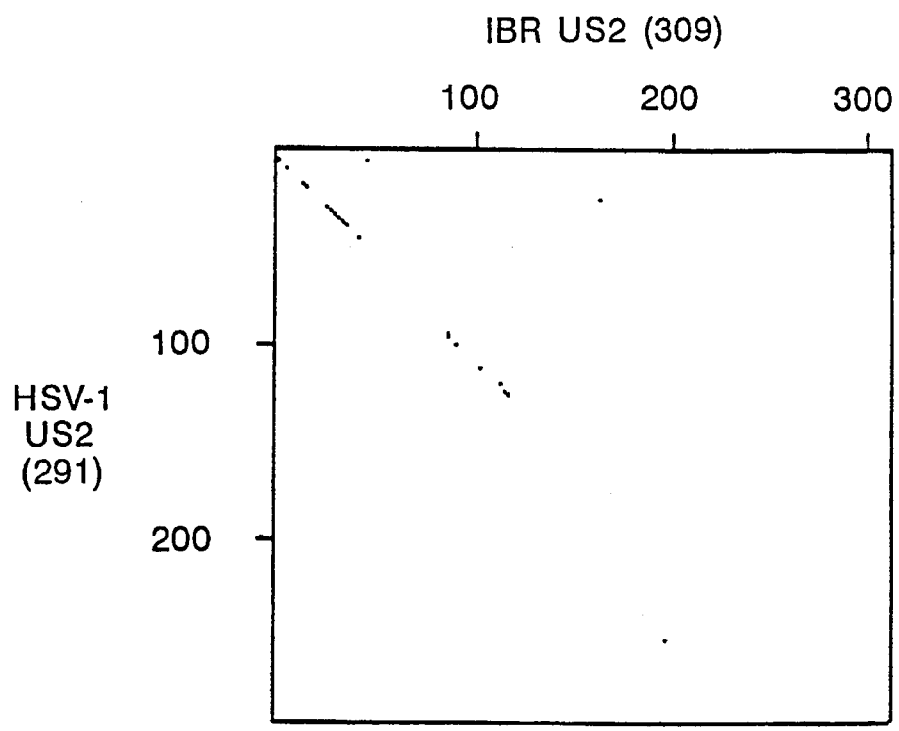
FIGS. 4A and 4B SEQ ID NOS: 2–6 Homology between the IBR US2 (SEQ ID NO: 2 protein and the US2 proteins of HSV-1 (SEQ ID NO: 3), PRV (SEQ ID NO: 4), HSV-2 (SEQ ID NO: 5), and MDV (SEQ ID NO: 6).

Observing that the Nasalgen IBR vaccine strain will not cause abortion when used in IBR-susceptible pregnant cows at various stages of gestation (18,65), we attempted to determine the genomic lesion responsible for this property. We characterized the genome of this virus by restriction mapping and DNA sequence analysis. It was determined that a major portion of the IBR virus US2 gene was deleted from the Nasalgen virus. Restriction mapping of the Nasalgen virus indicated that the HindIII K fragment contained an approximately 800 base pair deletion. The deletion was localized to the end of the HindIII K fragment located next to the HindIII O fragment (see FIG. 1). Therefore, the HindIII K fragment from the Cooper strain was subcloned and this region was sequenced. The first 1080 base pairs of the fragment were found to contain an open reading frame (ORF) coding for 309 amino acids (see FIG. 3). The ORF is 68% G+C and encodes a protein with a predicted molecular weight of 46,094. Comparison of the sequence of the predicted protein with sequences of gene products of HSV-1, PRV, HSV-2, and MDV in the unique short region indicated that this ORF is homologous to the herpesvirus US2 gene (see FIG. 4). Although the function of the herpesvirus US2 gene is not known, the gene has been shown to be nonessential for growth of HSV in cell culture (4,19). The US2 gene has also been shown to be deleted in the PRV vaccine strains Norden and Bartha (11).

Figure 5A:
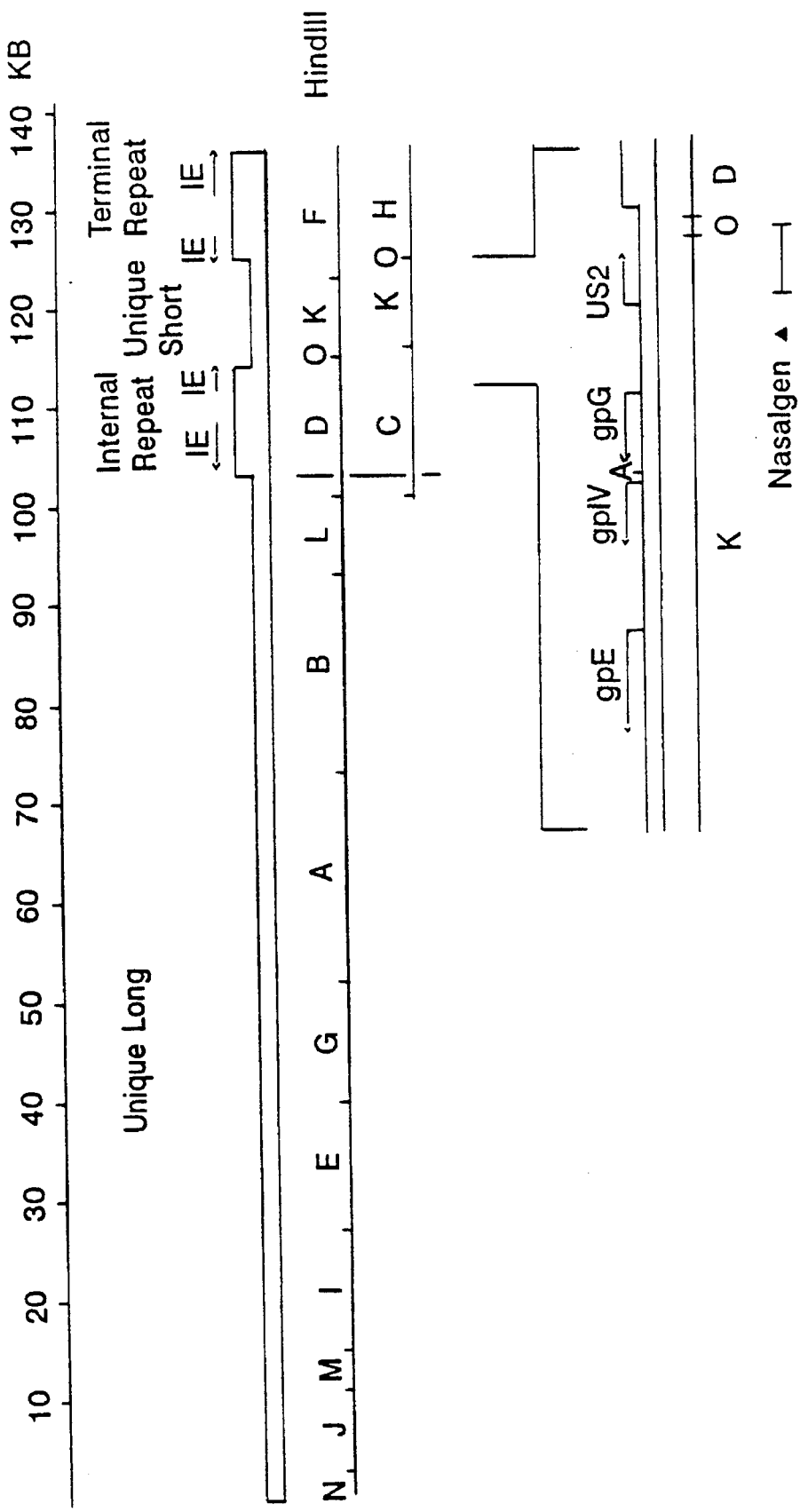
FIG. 5 SEQ ID NOS: 7–9 Details of the Nasalgen deletion. Diagram of IBR genomic DNA showing the unique long, internal repeat, unique short, and terminal repeat regions. A restriction map for the enzyme HindIII is indicated. Fragments are lettered in order of decreasing size. The unique short region is expanded for inclusion of more detail. The location of the deletion in the Nasalgen HindIII K fragment is shown. Three regions of DNA sequence are also shown. The first line (SEQ ID NO: 7) shows the first 60 base pairs upstream of the HindIII O/HindIII D junction in the IBR Cooper strain. The second line (SEQ ID NO: 8) shows the first 60 base pairs upstream of the HindIII K/HindIII D junction in the Nasalgen strain. The third line (SEQ ID NO: 9) shows 60 base pairs flanking the DNA encoding amino acid 59 of the IBR US2 gene in the IBR Cooper strain.

The HindIII K fragment from the Nasalgen virus was subcloned and the deletion region was sequenced. When the sequence obtained from the Nasalgen strain was compared to the sequence obtained from the Cooper strain (see FIG. 5), it was possible to determine that amino acids 59 to 309 of the US2 gene had been deleted. It was also determined that most of the HindIII O fragment had also been deleted.

Cattle studies have shown that the Nasalgen virus will not cause abortion when used in IBR-susceptible pregnant cows at various stages of gestation (18). Since the only major difference between the wild-type IBR strain and the Nasalgen strain resides in the deletion of the US2 gene, this gene may be involved in the fetal virulence observed for the wild type virus.

Example 3

S-IBR-027

Figure 6:
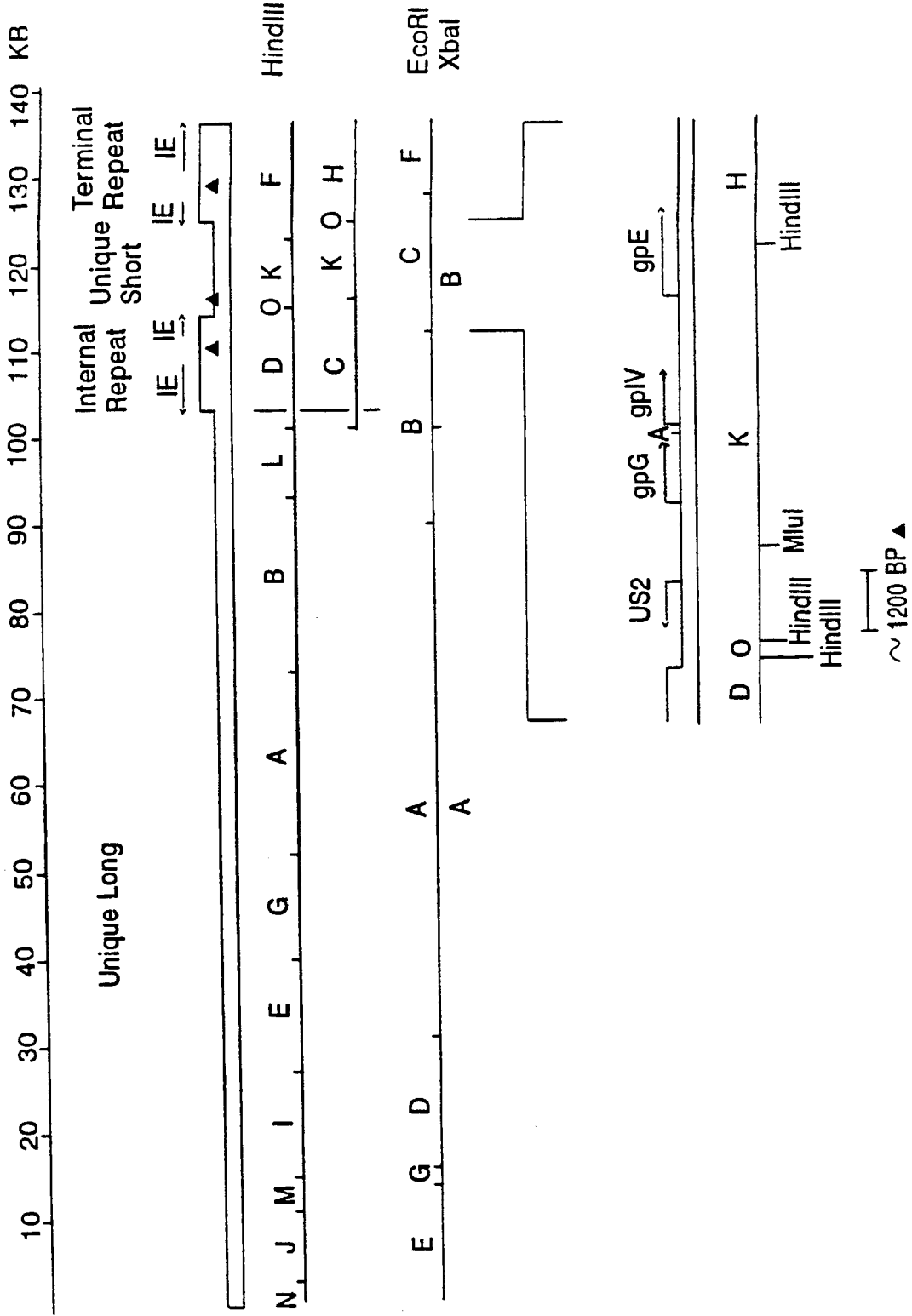
FIG. 6 Details of S-IBR-027. Diagram of S-IBR-027 genomic DNA showing the unique long, internal repeat, unique short, and terminal repeat regions. Restriction maps for the enzymes HindIII, EcoRI, and XbaI are indicated (7). Fragments are lettered in order of decreasing size. The unique short region is also expanded for inclusion of more detail. The location of several genes is also indicated, they are unique short 2 (US2), immediate early genes (IE) (20), glycoprotein G (gpG), glycoprotein IV (gpIV) (17), glycoprotein E (gpE). The unique short region and repeat region deletions are indicated by deltas. The location of the approximately 1200 BP deletion of the US2 gene is shown in the expanded region. Note that due to the inversion of the short region, which includes the unique short, internal, and terminal repeats, four half molar HindIII fragments are present (HindIII D, C, F, and H).

S-IBR-027 is an IBR virus that has a deletion of approximately 800 bp in the repeat regions and approximately 1200 bp in the short unique region of the genome. The deletion in the short unique region removes the US2 gene (FIG. 6). The repeat deletion was derived from the parental virus S-IBR-002 and is described in Example 2.

To construct this virus, the HOMOLOGOUS RECOMBINATION PROCEDURE FOR GENERATING RECOMBINANT HERPESVIRUS was performed. A homology vector containing the bacterial transposon Tn5 NEO (aminoglycosidase 3'-phosphotransferase) gene under the control of the HSV α4 promoter flanked by sequences from the IBR virus TK gene was constructed. The IBR virus homology regions were derived from the TK gene. The upstream homology included the first amino acid of the TK gene (15) and extended approximately 800 base pairs upstream of the TK coding region. The downstream homology included amino acids 156 to 357 and extended downstream of the TK coding region approximately 60 base pairs. S-IBR-002 DNA was mixed with the homology vector and transfected into rabbit skin cells as indicated in the methods. The transfection stock was selected according to the SELECTION OF G418 RESISTANT IBR VIRUS. Individual clones were picked after one round of selection and analyzed by the SOUTHERN BLOTTING OF DNA procedure. When a probe derived from the NEO gene was used in this analysis, one clone was found which did not hybridize to the NEO probe but had a HindIII restriction digestion pattern clearly distinct from the parental S-IBR-002. Further analysis indicated that the NEO had not been inserted into the TK region, however an approximately 1200 base pair deletion had occurred in the HindIII K fragment.

In order to characterize the HindIII K deletion, that fragment was subcloned and subjected to restriction mapping. Utilizing a series of oligonucleotide probes derived from the wild type sequence it was determined that approximately 1200 base pairs were deleted from the end of the HindIII K fragment adjacent to the HindIII K/HindIII O junction (see FIG. 6). This deletion removes the entire coding region of the US2 gene. S-IBR-027 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2322.

Direct fetal inoculation is the most sensitive test for determining the safety of live, IBR vaccines as regards their use in pregnant cows or in calves nursing pregnant cows. Three virus constructs were tested for fetal safety by inoculating directly into the bovine fetus, following laparotomy to expose the uterus. Abortion occurring within seven days after inoculation was considered to be surgically-induced. If fetuses aborted after this time, tissue samples were removed and cultured for the presence of the IBR construct. Caesarean sections were performed on cows with fetuses surviving for greater than 30 days post-inoculation. Fetal tissue was removed for virus culturing and blood samples were taken for evaluation of serum antibody to IBR virus.

The S-IBR-027 construct described above was tested, as well as two other constructs, S-IBR-020 and S-IBR-028. The S-IBR-020 construct was derived from the Cooper strain of IBR virus by making deletions in the repeat regions of the DNA and by inserting the Tn5 NEO gene.

The S-IBR-028 construct was derived from the Cooper strain of IBR virus by making deletions in the repeat region of the DNA and in the TK gene. The Tn5 NEO gene was also inserted into the TK deletion.

The following results were obtained from studies with the three virus constructs. In the studies with S-IBR-020, two fetuses were inoculated, one at approximately 130–140 days gestation and the other at approximately 170–180 days gestation. The younger fetus aborted twenty days after inoculation, but virus could not be recovered from tissue samples of this fetus (Table 2). The other fetus was live and appeared normal when it was surgically removed 60 days post-inoculation. In studies with S-IBR-027, four fetuses, ranging in age from 125 days to >250 days, were inoculated (Table 2). All fetuses survived and appeared normal. In studies with S-IBR-028, three fetuses, ranging in age from 140 days to >250 days, were inoculated. The youngest and eldest fetuses survived and appeared normal, however the fetus inoculated at 160–170 days gestation aborted nine days after inoculation.

Direct fetal inoculation is the most sensitive test for measuring the safety of live, IBR viruses used in pregnant cows. To date, the gene(s) involved in fetal virulence has not been reported. We have engineered IBR viruses with deletions in three different regions of IBR virus DNA and then determined the effect of the gene deletion. All three virus constructs tested have a deletion in the repeat region of the DNA and two constructs do not have TK activity. One fetus inoculated with each of the TK- constructs has aborted. In contrast, the construct with deletions in the repeat regions and the US2 gene (S-IBR-027) has been inoculated into four fetuses with no adverse reactions.

TABLE 2

Safety of IBR Viruses for Bovine Fetuses

| Construct | Fetal Age[a] | Results |
|---|---|---|
| S-IBR-020 | 130–140 Days | Fetus aborted Day 20 post-inoculation; no virus isolated |
|  | 170–180 Days | Normal, live fetus 60 days post-inoculation |
| S-IBR-027 | 125–135 Days | Normal, live fetus 60 days post-inoculation |
|  | 150–160 Days | Normal, live calf born 56 days post-inoculation |
|  | 220–240 Days | Normal, live calf born 30 days post-inoculation |
|  | >250 Days | Normal, live calf born 30 days post-inoculation |
| S-IBR-028 | 140–150 Days | Normal, live fetus 60 days post-inoculation |
|  | 160–170 Days | Fetus aborted Day 9 post-inoculation; no virus isolated |
|  | >250 Days | Normal, live calf born 12 days post-inoculation |

[a]Approximate age at time of virus inoculation

We have shown that S-IBR-027 is safe for fetal inoculation in contrast to S-IBR-020 and S-IBR-028 which are not. Although all three viruses were engineered by similar approaches, the distinguishing difference of S-IBR-027 is the deletion of the US2 gene. We have also shown that the Nasalgen virus, which was generated by independent methods and is safe for use in IBR-susceptible pregnant cows, has been deleted in the US2 gene.

Although the S-IBR-027 and Nasalgen have the similar property of fetal safety, S-IBR-027 offers additional advantages. The major portion of the US2 gene (251 out of 309 amino acids) has been deleted in the Nasalgen virus. This deletion would clearly inactivate the gene, however the remaining portion of the gene may make it more likely to revert to virulence via recombination with other viruses. The complete coding region of the US2 has been deleted from S-IBR-027 making it less likely that this gene could be restored and revert the virus to virulence. The S-IBR-027 construct also carries an important deletion in the repeat region, which is not present in the Nasalgen virus. A deletion in the analogous region of the pseudorabies virus (PRV) has been shown to be valuable in attenuating PRV for swine (see U.S. Pat. No. 4,877,737). This deletion has also been shown to attenuate IBR for cattle as seen in the testing of S-IBR-002 (see Example 1).

Example 4

S-IBR-028

S-IBR-028 is an IBR virus that has a deletion of approximately 800 bp in the repeat regions and approximately 250 bp in the TK region of the genome. The deletion in the TK region inactivates the TK gene. The repeat deletion was derived from the parental virus S-IBR-002 and is described in Example 2.

To construct this virus, the HOMOLOGOUS RECOMBINATION PROCEDURE FOR GENERATING RECOMBINANT HERPESVIRUS was performed. A homology vector containing the bacterial transposon Tn5 NEO (aminoglycosidase 3'-phosphotransferase) gene under the control of the HSV-1 α4 gene promoter flanked by sequences from the IBR virus TK gene was constructed. The IBR virus homology regions were derived from the TK gene. The upstream homology included amino acids 1 to 62 of the TK gene (15) and extended approximately 674 base pairs upstream of the TK coding reigon. The downstream homology included amino acids 156 to 357 and extended downstream of the TK coding region approximately 1138 base pairs. S-IBR-002 DNA was mixed with the homology vector 129-71.5 and transfected into rabbit skin cells as indicated in the methods. The transfection stock was selected according to the SELECTION OF G418 RESISTANT IBR VIRUS.

Individual clones were picked after two rounds of selection and analyzed by the SOUTHERN BLOTTING OF DNA procedure. Several clones were assayed for TK activity by a $^{14}$C-thymidine incorporation assay (29). One clone which was negative for TK activity was chosen and characterized by digestion with HindIII and XbaI. The restriction endonuclease analysis confirmed that the NEO gene had been inserted into the TK gene. This clone, designated S-IBR-028, has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2326.

Example 5

Glycoprotein G gene

Deletion of the PRV gpX gene has been shown to be valuable both as an attenuating lesion and as a negative serological marker (see U.S. Ser. No. 07/192,866, filed May 11, 1988). In the studies described below we show that the unique short region of IBR virus contains a gene homologous to the gpX gene of PRV.

Figures 9A, 9B:
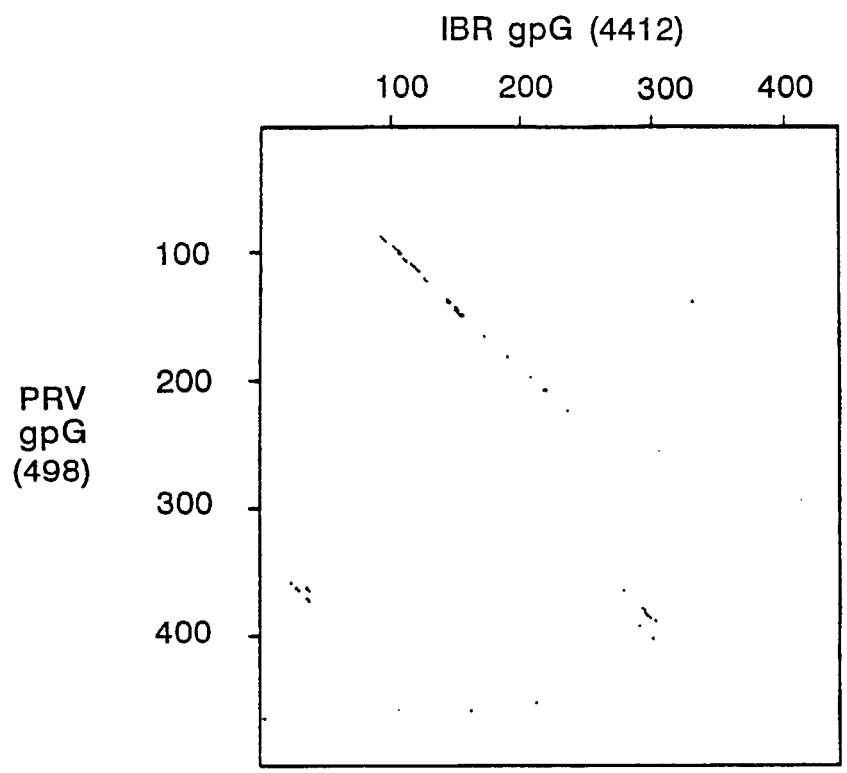
FIGS. 9A & 9B SEQ ID NOS: 17–19 Homology between the IBR gpG (SEQ ID NO: 17) protein, the gpX protein of PRV (SEQ ID NO: 18) and the gpG protein of HSV-2 (SEQ ID NO: 19).

The sequence of an approximately 1400 base pair region of the IBR HindIII K fragment (see FIG. 8), located approximately 2800 base pairs downstream of the HindIII K/HindIII O junction was determined. This region was found to contain an ORF coding for 441 amino acids translated in the direction away from the HindIII K/HindIII O junction (see FIG. 1). The ORF is 69% G+C and encodes a protein with a predicted molecular weight of 58,683. Comparison of the sequence of the predicted protein with sequences of gene products of HSV-2 and PRV in the unique short region indicated that this ORF is homologous to the herpesvirus gpG gene (see FIG. 9). The complete gpG gene resides on an approximately 2800 base pair MluI to NdeI sub-fragment of the IBR virus HindIII K fragment. This sub-fragment has been cloned as a blunt ended fragment into the plasmid pSP64. This plasmid is designated PSY1643. PSY1643 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68652. This plasmid may be used to confirm the sequence of the gpG gene. The sequence of the gpG gene may also be confirmed by comparing the appropriate DNA sequence of the wild type virus S-IBR-000 (Cooper Strain) with the sequence of the gpG deleted virus S-IBR-037 (ATCC Accession No. 2320).

Figure 10:
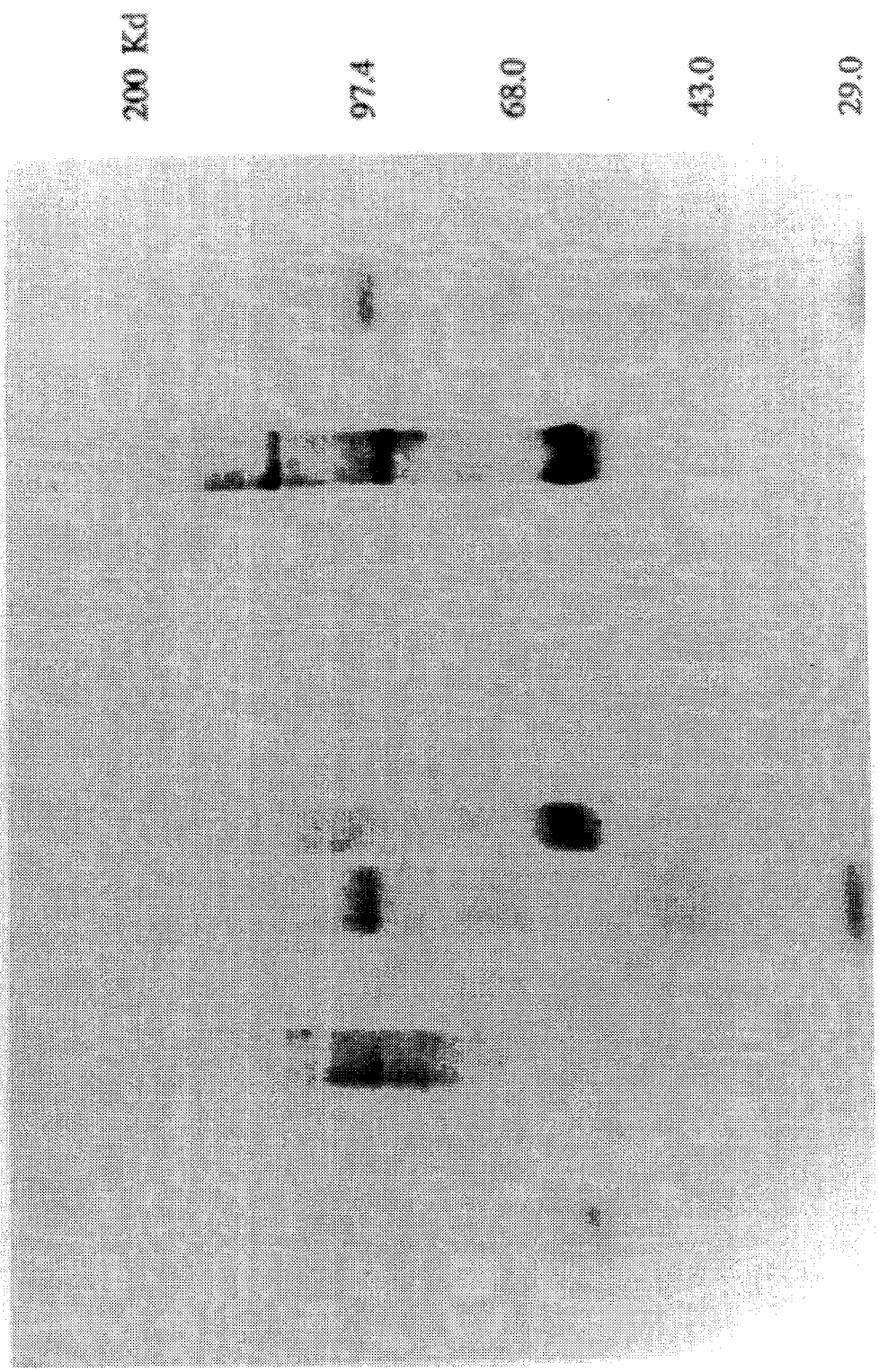
FIG. 10 Western blot of proteins released into the medium of IBR and PRV infected cells, showing the absence of gpG in S-PRV-013, S-IBR-035, S-IBR-036, S-IBR-037, and S-IBR-038 but its presence in S-PRV-160 and wild type S-IBR-000. Lanes (A) 0.5 µg purified gpG, (B) blank lane, (C) S-PRV-160, (D) S-PRV-013, (E) pre-stained molecular weight markers, (F) 0.5 µg purified gpG, (G) S-IBR-038, (H) S-IBR-037, (I) S-IBR-036, (J) S-IBR-035, (K) S-IBR-000, (L) uninfected MDBK cells, (M) pre-stained molecular weight markers. Media samples were prepared as described in the PREPARATION OF HERPESVIRUS CELL LYSATES. The concentrated media from the infection of one 6 cm dish of infected cells was loaded in each sample lane except for samples S-PRV-013 AND S-PRV-160 for which the media from two 6 cm dishes were loaded.

To confirm the expression of the IBR virus gpG gene product, cells were infected with IBR virus and samples of media from infected cultures were subjected to SDS-polyacrylamide gel electrophoresis. The gel was blotted and analyzed using the WESTERN BLOTTING PROCEDURE. The anti-serum used was a mouse hyper-immune serum raised against chemically-synthesized gpG peptides (amino acids 242–254 and 269–289) linked to keyhole limpet hemocyanin. As shown in FIG. 10, gpG is prominent in the media of cells infected with wild type virus (S-IBR-000), but is not detected in media of mock infected cells.

Example 6

S-PRV-160

S-PRV-160 is a pseudorabies virus that has a deletion in the TK gene in the long unique region, a deletion in the repeat region, and an approximately 1414 base pair deletion in the gpX coding region. The gene for E.coli β-galactosidase (lacZ gene) was inserted in the place of the gpX gene and is under the control of the gpX promoter. A chimeric gene coding for an IBR virus gpG, PRV gpIII and PRV gpX fusion protein was inserted at the HindIII sites located in each repeat.

S-PRV-160 was constructed utilizing plasmid 459-12.6, pseudorabies virus S-PRV-013 (see U.S. Ser. No. 823,102, filed Jan. 27, 1986 and U.S. Ser. No. 07/192,866, filed May 11, 1988) and the restriction enzyme HindIII in the DIRECT LIGATION PROCEDURE FOR GENERATING RECOMBINANT HERPESVIRUS. Several clones were screened by digestion with HindIII for the presence of the HindIII band containing the chimeric gene insert from plasmid 459-12.6. One clone exhibiting the correct HindIII insert band was chosen and designated S-PRV-160.

S-PRV-160 was constructed so that it would express precisely the gpG specific amino acids that were deleted in S-IBR-037. This allows the gpG fusion protein expressed in S-PRV-160 to be used as an antigen to identify antibodies directed against the wild type virus as opposed to antibodies directed against S-IBR-037. Note that gpX, the PRV homologue of IBR virus gpG, has been deleted from S-PRV-160 to prevent any confusion resulting from cross reactivity that might exist between the two proteins. To confirm that S-PRV-160 does express IBR virus gpG, a Western blot analysis was performed. As can be seen in FIG. 10, gpG specific antibody does react with an appropriately sized media protein from S-PRV-160.

S-PRV-160 may also be utilized as an antigen for the production of gpG specific monoclonal antibodies. Such antibodies are useful in the development of diagnostic tests specific for the gpG protein. Monoclonal antibodies were generated in mice utilizing S-PRV-160 according to the PROCEDURE FOR GENERATING MONOCLONAL ANTIBODIES. One of these antibodies, clone 3-1G7, was shown to react specifically with purified gpG in the gpG ELISA assay.

Example 7

S-IBR-035

S-IBR-035 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 294 base pairs and begins in the HindIII K fragment approximately 3900 base pairs downstream of the HindIII K/HindIII O junction and extends back toward that junction. This deletion removes amino acids 263 to 361 of the gpG gene. The gene for E.coli β-galactosidase (lacZ gene) was inserted into the deletion in the gpG gene and is under the control of the HCMV immediate early promoter.

S-IBR-035 was derived from S-IBR-000 (Cooper strain). This was accomplished utilizing the homology vector 439-01.31 (see Materials and Methods) and virus S-IBR-000 in the HOMOLOGOUS RECOMBINATION PROCEDURE FOR GENERATING RECOMBINANT HERPESVIRUS. The transfection stock was screened by the BLUOGAL SCREEN FOR RECOMBINANT HERPESVIRUS. The final result of blue plaque purification was the recombinant virus designated S-IBR-035. This virus was characterized by restriction mapping and the SOUTHERN BLOTTING DNA procedure. This analysis confirmed the insertion of the β-galactosidase (lacZ) marker gene and the deletion of approximately 294 base pairs of the gpG gene. It was also confirmed that an approximately 2500 base pair deletion had occurred in the region of the US2 gene.

Example 8

S-IBR-036

S-IBR-036 is an IBR virus that has two deletions in the short unique region of the genome. The first deletion is approximately 2500 base pairs and is similar to the deletion in S-IBR-035 (see Example 7) which removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gpG gene. The gene for E.coli β-galactosidase (lacZ gene) was inserted into the deletion in the gpG gene and is under the control of the HCMV immediate early promoter.

S-IBR-036 was derived from S-IBR-000 (Cooper strain). This was accomplished utilizing the homology vector 439-21.69 (see Materials and Methods) and virus S-IBR-000 in the HOMOLOGOUS RECOMBINATION PROCEDURE FOR GENERATING RECOMBINANT HERPESVIRUS. The transfection stock was screened by the BLUOGAL SCREEN FOR RECOMBINANT HERPESVIRUS. The final result of blue plaque purification was the recombinant virus designated S-IBR-036. This virus was characterized by restriction mapping and the SOUTHERN BLOTTING DNA procedure. This analysis confirmed the insertion of the β-galactosidase (lacZ) marker gene and the deletion of approximately 1230 base pairs of the gpG gene. It was also confirmed that an approximately 2500 base pair deletion had occurred in the region of the US2 gene (see above).

Example 9

S-IBR-037

S-IBR-037 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gpG gene.

S-IBR-037 was derived from S-IBR-035. This was accomplished utilizing the homology vector 439-70.4 (see Materials and Methods) and virus S-IBR-035 in the HOMOLOGOUS RECOMBINATION PROCEDURE FOR GENERATING RECOMBINANT HERPESVIRUS. The transfection stock was screened by the BLUOGAL SCREEN FOR RECOMBINANT HERPESVIRUS. The result of white plaque purification was the recombinant virus designated S-IBR-037. This virus was characterized by restriction mapping and the SOUTHERN BLOTTING DNA procedure. This analysis confirmed the deletion of the β-galactosidase (lacZ) marker gene and the deletion of approximately 1230 base pairs of the gpG gene. It was also confirmed that an approximately 2500 base pair deletion had occurred in the region of the US2 gene (see above). S-IBR-037 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2320.

To test the efficacy of S-IBR-037 as an inactivated IBR virus vaccine in protecting susceptible calves against virulent IBR virus challenge, a study was performed according to the VACCINATION STUDIES IN CALVES WITH INACTIVATED IBR VIRUS. The following results were observed.

Virus neutralization antibody titers were elicited in animals after the first vaccination (see Table 3). Antibody titers were not significantly different between animals that received a vaccine dose of $10^{7.3}$ virus and animals vaccinated with $10^{8.0}$ virus. After the second vaccination, mean antibody titers increased to 1:19 and 1:32, respectively, for the $10^{7.3}$ and $10^{8.0}$ vaccine groups. Control animals remained seronegative to IBR virus throughout the vaccination period. Antibody titers in both vaccinate groups showed an increase typical of an anamnestic response after challenge with virulent IBR virus. By 13 days post challenge, mean antibody titers were 1:152 and 1:215 for the $10^{7.3}$ and $10^{8.0}$ vaccinate groups respectively. In contrast, mean antibody titers in challenged control animals were 1:4 at 7 days and 1:8 at 13 days post challenge.

Nasal swabs were collected from challenged animals to determine whether vaccination decreased the time of virus shedding (Table 4). The most dramatic difference between vaccinates and control animals was observed at 12 days post challenge. At this time, seventy-five percent of controls animals continue to shed, whereas, only twenty-five percent of both vaccinate groups shed virus. Virus was not isolated from control or vaccinated groups at 15 days post challenge.

TABLE 3

Generation of virus neutralizing antibody in animals vaccinated with inactivated S-IBR-037 vaccine.

| | Antibody titer[a] on days: | | | | | |
|---|---|---|---|---|---|---|
| | Post Vaccination | | | | Post Challenge | |
| Animal No. | 7 | 21 | 28 | 42 | 7 | 13 |
| Controls | | | | | | |
| 9 | ≤2 | ≤2 | ≤2 | ≤2 | 4 | 4 |

TABLE 3-continued

Generation of virus neutralizing antibody in animals vaccinated with inactivated S-IBR-037 vaccine.

| | Antibody titer[a] on days: | | | | | |
|---|---|---|---|---|---|---|
| | Post Vaccination | | | | Post Challenge | |
| Animal No. | 7 | 21 | 28 | 42 | 7 | 13 |
| 22 | ≦2 | ≦2 | ≦2 | ≦2 | 4 | 8 |
| 32 | ≦2 | ≦2 | ≦2 | ≦2 | 4 | 16 |
| 64 | ≦2 | ≦2 | ≦2 | ≦2 | 4 | 8 |
| GMT | ≦2 | ≦2 | ≦2 | ≦2 | 4 | 8 |
| Vaccinates dose $10^{7.3}$ | | | | | | |
| 1 | ≦2 | 8 | 32 | 64 | 64 | 128 |
| 20 | ≦2 | 8 | 32 | 64 | 64 | 256 |
| 25 | ≦2 | 8 | 16 | 8 | 64 | 512 |
| 36 | ≦2 | 4 | 16 | 4 | 16 | ≧32 |
| GMT | ≦2 | 6.7 | 22.6* | 19.0* | 45.34* | 152.2* |
| Vaccinates dose $10^{8.0}$ | | | | | | |
| 7 | ≦2 | 4 | 32 | 8 | 64 | 256 |
| 30 | ≦2 | ≧8 | 64 | 128 | 128 | ≧128 |
| 33 | ≦2 | 16 | 32 | 128 | 128 | 256 |
| 69 | ≦2 | 4 | 16 | 8 | 128 | 256 |
| GMT | ≦2 | 6.7 | 32* | 32* | 107.6* | 215.3* |

*Statistically greater than controls (p ≦ 0.05)
[a]Expressed as reciprocal of dilution.

TABLE 4

Isolation of IBR virus from vaccinated and unvaccinated control animals after challenge with virulent IBR virus.

| | IBR virus isolated (+/−) from animals on days post challenge | | | | |
|---|---|---|---|---|---|
| Animal No. | 3 | 6 | 9 | 12 | 15 |
| Controls | | | | | |
| 9 | − | + | + | + | − |
| 22 | − | + | + | − | − |
| 32 | − | + | + | + | − |
| 64 | − | + | + | + | − |
| Vaccinates dose $10^{7.3}$ | | | | | |
| 1 | − | + | + | − | − |
| 20 | − | + | + | − | − |
| 25 | − | + | + | − | − |
| 36 | − | + | + | + | − |
| Vaccinates dose $10^{8.0}$ | | | | | |
| 7 | − | + | + | − | − |
| 30 | − | − | − | − | − |
| 33 | − | + | + | + | − |
| 69 | − | + | + | − | − |

TABLE 5

Vaccinated animals demonstrate reduced clinical signs of IBR.

| | Clinical scores post challenge | | | | |
|---|---|---|---|---|---|
| Animal No. | Attitude[a] | Nasal Ulcers[b] | Serous Discharge[c] | Mucopurulent Discharge[d] | Temperature[e] |
| Controls | | | | | |
| 9 | 5 | 3 | 11 | 5 | 3 |
| 22 | 2 | 2 | 12 | 3 | 1 |
| 32 | 5 | 3 | 11 | 0 | 4 |
| 64 | 6 | 3 | 11 | 1 | 1 |
| GMS | 4.5 | 2.8 | 11.3 | 2.3 | 2.3 |
| Vaccinates dose $10^{7.3}$ | | | | | |
| 1 | 0 | 2 | 1 | 0 | 0 |
| 20 | 0 | 1 | 3 | 0 | 0 |
| 25 | 0 | 2 | 6 | 2 | 0 |
| 36[f] | 6 | 2 | 1 | 13 | 0 |
| GMS | 1.5 | 1.8 | 2.8* | 2.3 | 0 |
| Vaccinates dose $10^{8.0}$ | | | | | |
| 7 | 1 | 2 | 1 | 0 | 0 |
| 30 | 1 | 2 | 2 | 2 | 0 |
| 33 | 1 | 2 | 0 | 0 | 0 |
| 69 | 1 | 2 | 0 | 0 | 0 |
| GMS | 1 | 2 | 0.8* | 0.5 | 0 |

[a]Days with depressed attitude.
[b]Number of ulcers.
[c]Days with serous discharge.
[d]Days with mucopurulent discharge.
[e]Days with ≧2° F. above baseline temperature.
[f]Animal exhibited mucopurulent discharge on the day of challenge and for 13 days post challenge.
*Statistically different from controls (p ≦ 0.05)

Animals were observed daily for 13 days post challenge for clinical signs of IBR infection. Clinical disease was evaluated with respect to attitude, the number of ulcers, extent of serous and mucopurulent discharge and the number of days with elevated temperature. The results presented in Table 5 show that vaccinated animals exhibited less severe disease than did unvaccinated control animals. Control animals showed clinical depression ("Attitude" in Table 5) for 4.5 days compared with 1 to 1.5 days for vaccinated animals. The amount and extent of serous discharge was substantially reduced in both vaccinate groups compared with controls. The extent of mucopurulent discharge was also reduced in vaccinated animals, although to a lesser degree. However, vaccinate animal #36 did have mucopurulent discharge on the day of challenge and is not consistent with the results for other vaccinates. None of the vaccinates exhibited temperatures of ≧2° F. above baseline. In contrast, all control animals exhibited elevated temperatures of ≧2° F. over baseline and 2 of 4 control animals had temperatures of 104° F. and above.

Vaccination of calves with inactivated S-IBR-037 vaccine protected the animals against virulent wild-type IBR virus challenge. Virus neutralization titers were statistically greater in vaccinated than in control animals. An anamnestic response in antibody titer was observed 7 days post challenge, indicating the development of humoral memory response. Except for 7 days post challenge, neutralization titers between the $10^{7.3}$ and $10^{8.0}$ vaccinate groups were not statistically different. Fewer vaccinated animals shed virulent challenge virus than control animals. These results suggest that virulent IBR virus is cleared more rapidly in vaccinated than in unvaccinated animals. Clinical symptoms of IBR virus infection were also reduced in vaccinated animals. After challenge, both vaccinate groups exhibited fewer days of depressed attitude, reduced serous discharge, and no elevated temperature compared with controls.

In order to show that gpG antibody is produced in vaccinated calves following exposure to wild-type virus, serum samples taken pre- and post-exposure to wild-type virus were subjected to the ELISA assay. Samples taken at the day of challenge and at 13 days post-challenge were analyzed. As seen in Table 6, the post-challenge absorbance readings for gpG increase for each animal (ratio of >1.0), indicating that within 13 days of infection a detectable immune response to gpG is present.

TABLE 6

Detection of antibody to gpG in serum of animals vaccinated with S-IBR-037 and challenged with wild type.

| Animal No. | Ratio of pre- vs. post challenge[a] |
|---|---|
| Controls | |
| 9 | 1.22 |
| 22 | 1.96 |
| 32 | 1.87 |
| 64 | 2.19 |
| Vaccinates dose $10^{7.3}$ | |
| 1 | 1.39 |
| 20 | 1.40 |
| 25 | 1.84 |
| 36 | 1.18 |
| Vaccinates dose $10^{8.0}$ | |
| 7 | 1.19 |
| 30 | 1.29 |
| 33 | 1.52 |
| 69 | 2.66 |

[a]Animals were challenged with $10^{7.6}$ PFU of wild type IBR virus. Pre-challenge serum from day of challenge, post-challenge serum from 13 days post challenge. Data reflects the average of the ratio of absorbance readings for three independent ELISA determinations.

Example 10

S-IBR-038

S-IBR-038 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 294 base pairs and begins in the HindIII K fragment approximately 3900 base pairs downstream of the HindIII K/HindIII O junction and extends back toward that junction. This deletion removes amino acids 263 to 361 of the gpG gene.

S-IBR-038 resulted from the removal of the marker gene from S-IBR-035 (see above). This was accomplished by digestion of S-IBR-035 with XbaI as described in the DIRECT LIGATION PROCEDURE FOR GENERATING RECOMBINANT HERPESVIRUS. The structure of S-IBR-035 was confirmed by restriction enzyme analysis with HindIII, BamHI and XbaI.

Example 11

Glycoprotein E gene

Deletion of the PRV gI gene has been shown to be valuable both as an attenuating lesion and a negative serological marker (3,42). In the studies described below we show that the unique short region of IBR virus contains a gene homologous to the gI gene of PRV.

Figure 16A:
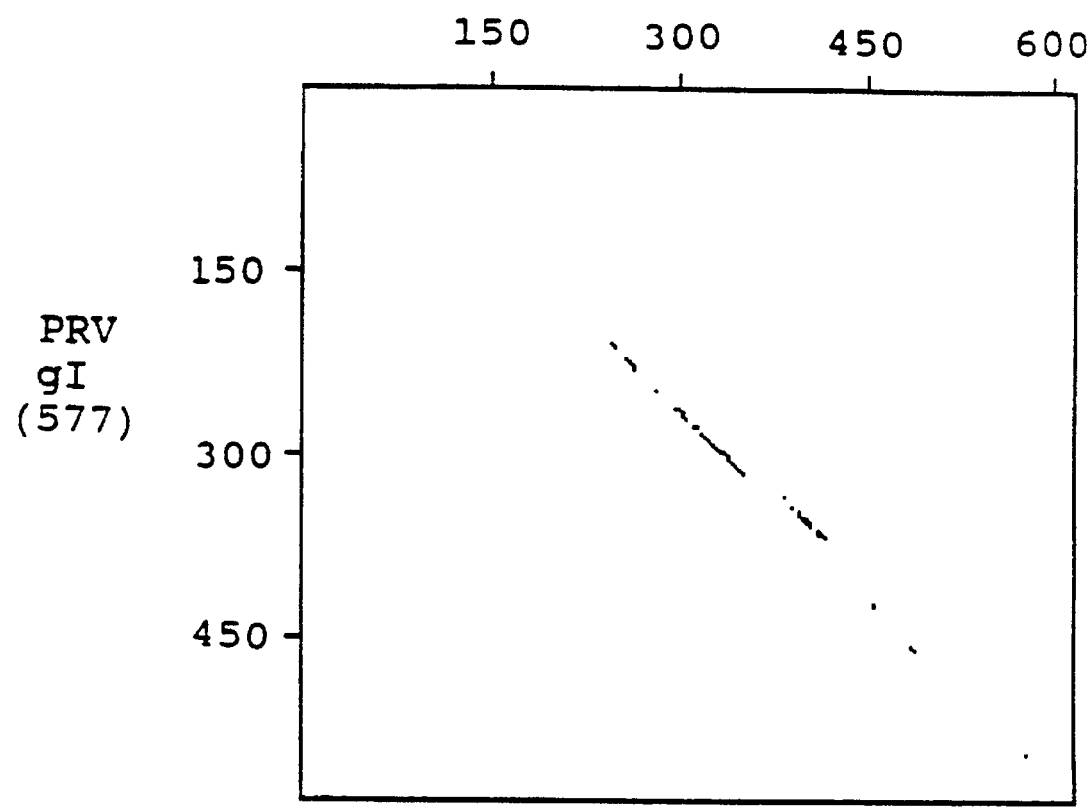

The sequence of 2038 base pairs of the IBR unique short region, starting approximately 1325 base pairs upstream of the HindIII K/HindIII F junction in the HindIII K fragment was determined. This region was found to contain an ORF coding for 617 amino acids translated in the direction away from the HindIII K/HindIII O junction (see FIG. 1). The ORF is 70.5% G+C and encodes a protein with a predicted molecular weight of approximately 88,980. Comparison of the sequence of the predicted protein with sequences of gene products of HSV-1, VZV, and PRV in the unique short region indicated that this ORF is homologous to the herpesvirus gpE gene (see FIG. 16).

The DNA encoding the gpE gene has been cloned in two plasmids, PSY1644 and PSY1645. The amino-terminal half of the gene (encoding amino acids 1–276) was cloned as an approximately 2300 base pair fragment resulting from a partial SmaI digest of wild type S-IBR-000 (Cooper Strain) DNA. This fragment was inserted into the plasmid pSP64 to yield PSY1644. This plasmid, designated PSY1644, has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68651. The carboxyl-terminal half of the gene (encoding amino acids 277–617) was cloned as an approximately 2400 base pair SmaI fragment. This fragment was inserted into the plasmid pSP64 to yield PSY1645. This plasmid, designated PSY1645, has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68650. These plasmids may be used to confirm the sequence of the gpE gene.

Example 12

Pseudorabies virus expressing IBR virus gpE

A pseudorabies virus analogous to S-PRV-160 may be constructed for the purpose of expressing the IBR virus gpE. This may be accomplished by inserting the gene coding for IBR virus gpE into S-PRV-002 (U.S. Pat. No. 4,877,737).

Such an expression vector may be constructed utilizing the IBR virus gpE plasmid described in the methods section, pseudorabies virus S-PRV-002 and the restriction enzyme XbaI in the DIRECT LIGATION PROCEDURE FOR GENERATING RECOMBINANT HERPESVIRUS. Viruses resulting from this procedure may be screened by digestion with XbaI for the presence of the XbaI band containing the IBR virus gpE gene. The gpE protein expressed from this vector may be used as an antigen to identify antibodies directed against the wild type virus as opposed to antibodies directed against gpE deleted viruses. This virus may also be utilized as an antigen for the production of gpE specific monoclonal antibodies. Such antibodies are useful in the development of diagnostic tests specific for the gpE protein. Monoclonal antibodies may be generated in mice utilizing this virus according to the PROCEDURE FOR GENERATING MONOCLONAL ANTIBODIES.

Example 13

Glycoprotein E deleted IBR viruses

The HOMOLOGY VECTOR 536-03.5 was used to generate various gpE-deleted IBR viruses. Utilizing the general strategy described in CONSTRUCTION OF DELETION VIRUSES, a gpE deletion of approximately 1410 base pairs (amino acids 77–547) was introduced into two different IBR virus backbones, S-IBR-000 (Cooper Strain) and S-IBR-037. The virus resulting from the S-IBR-000 parent contains the gpE deletion alone. The virus resulting from the S-IBR-037 parent contains the gpE deletion in conjunction with the US2 and gpG deletions. The lacZ marker gene may be removed from these viruses utilizing the procedures outlined in the methods section.

These gpE-deleted viruses are of great value as IBR vaccines. Their combination of different deletions will provide the varying degrees of attenuation which are required for a superior vaccine. These viruses will also provide a negative serological marker which may be used to distinguish vaccinated from infected animals. The virus containing both gpG and gpE deletions should be of even greater value by having two negative markers. The availability of two negative markers permits one marker to be used as a confirmatory test, greatly increasing the reliability of such a diagnostic determination.

Example 14

S-IBR-004

S-IBR-004 is an IBR recombinant virus carrying an inserted foreign gene, Tn5 NEO (aminoglycoside 3'-phosphotransferase) gene, under the control of the pseudorabies virus (PRV) glycoprotein X promoter.

To construct this virus, the HindIII K DNA fragment from wild type IBR virus was cloned into the plasmid pSP64 at the HindIII site. This plasmid was designated pSY524. A map of the HindIII K fragment is shown in FIG. 19. The DNA from the XhoI site to the HindIII site and containing the NdeI site from pSY524 was cloned into plasmid pSP65 and called pSY846. The NdeI to EcoRI fragment was removed from pSY846 by digestion with NdeI and EcoRI restriction enzymes, followed by POLYMERASE FILL-IN REACTION and LIGATION. The resulting plasmid was called pSY862. The plasmid pNEO (P.L. Biochemicals, Inc.) contains the aminoglycoside 3'-phosphotransferase (NEO) gene and confers resistance to ampicillin and neomycin on *E. coli* hosts. The coding region of this gene (BglII-BamHI fragment) was isolated and cloned between the PRV gpX promoter and the HSV-TK poly A sequence in a plasmid called pSY845.

The NEO gene construct in pSY845 was excised with HindIII, made blunt ended by the POLYMERASE FILL-IN REACTION, and cloned into the SacI site of plasmid pSY862. The final product was called pSY868.

Wild type IBR DNA was mixed with pSY868 DNA and the mixture was transfected into rabbit skin cells to generate recombinant IBR. The recombinant IBR virus carrying a functional NEO gene was then isolated and purified according to the SELECTION OF G418 RESISTANT IBR VIRUS method.

S-IBR-004 recombinant IBR was shown to express the NEO gene by the fact that cells infected with this virus were resistant to the toxicity of G418. A detailed map of the plasmid construction is shown in FIG. 19. The structure of S-IBR-004 is also shown in FIG. 19. S-IBR-004 has been deposited pursuant to the Budapest Treaty on the International Deposit of Microorganisms for the Purposes of Patent Procedure with the Patent Culture Depository of theAmerican Type Culture Collection, 12301 Parklawn Drive, Rockville, Md. 20852 U.S.A. under ATCC Accession No. VR 2134.

Example 15

S-IBR-008

S-IBR-008 is an IBR virus that has a deletion in the short unique region, and an insertion of the bovine rotavirus glycoprotein 38 (gp38) gene in the XbaI site in the long unique region.

The bovine rotavirus gp38 gene was cloned utilizing the METHOD FOR cDNA CLONING BOVINE ROTAVIRUS gp38 GENE. The bovine rotavirus gp38 gene was then engineered to contain herpesvirus regulatory signals as shown in FIG. 20. This was accomplished by cloning the gp38 gene BamHI fragment contained in pSY1053 between the BamHI and BglII sites in pSY1052. The resulting plasmid, pSY1023, contained the PRV gpX promoter in front of the gp38 gene, and the HSV-1 TK polyadenylation signal behind the gp38 gene. The entire construct was flanked by XbaI sites to allow for the insertion of the XbaI fragment into IBR virus by direct ligation.

S-IBR-004 was the starting virus for the generation of S-IBR-008. S-IBR-004 DNA and pSY1023 DNA were mixed together, cut with XbaI, and transfected into rabbit skin cells according to the DIRECT LIGATION PROCEDURE FOR GENERATING RECOMBINANT HERPESVIRUS. The transfection stock was screened for recombinant virus by the ANTIBODY SCREEN FOR RECOMBINANT HERPESVIRUS procedure using antibodies prepared against the rotavirus gp38 protein.

One of the viruses purified by this screen was S-IBR-008, which has the following characteristics. It contains the rotavirus gp38 gene plus the plasmid DNA inserted into the XbaI site in the long unique region of the virus genome, but no longer contains the NEO gene of parent S-IBR-004 in the unique short region. In fact, a small deletion was created in the unique short region at the location of the NEO gene, as evidenced by the absence of an XbaI site at this location in S-IBR-008.

S-IBR-008 was shown to be expressing the rotavirus gp38 gene by analysis of RNA transcription in infected cells, and by the ANTIBODY SCREEN FOR RECOMBINANT HERPESVIRUS procedure using antibodies specific for the gp38 gene. S-IBR-008 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2141. The structure of S-IBR-008 is shown in FIG. 20.

Example 16

S-IBR-018

S-IBR-018 is an IBR virus that has three foreign genes inserted: the *E.coli* beta-galactosidase gene and the neomycin resistance gene in the XbaI site in the unique long region, and the parainfluenza-3 (PI-3) virus hemaglutinin gene (HN) in the HindIII site in the unique long region immediately adjacent to the XbaI site.

For cloning the PI-3 HN gene, the SF-4 strain of PI-3 was grown in MADIN-DARBY bovine kidney (MDBK) cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the human PI-3 HN gene has been published (25,26) and this information was used to locate the gene in applicants' bovine PI-3 clones. The entire open reading frame of the bovine PI-3 HN gene was sequenced by applicants and is given in FIG. 21.

The HSV alpha-4 promoter was used to express the PI-3 HN gene and the HSV TK poly-A signal was used to terminate transcription. The engineering of this construct was done as shown in FIG. 22 A and B. The construct contained (5' to 3') the HSV ICP4 promoter, the ICP4 TATA box, the ICP4 cap site, a fusion within the ICP4 5' untranslated region to the PI-3 HN gene at the HhaI site, the HN gene. start codon, the HN structural gene, the HN stop codon, a fusion within the HN 3' untranslated region to the HSV TK untranslated 3' region, and the HSV TK poly-A signal sequence.

This plasmid also contained the beta-galactosidase (lacZ) gene under the control of the PRV gpX promoter with the gpX poly-A termination signal, as well as the neomycin resistance gene under the control of the gpX promoter with the TK poly-A termination signal. These latter two genes were cloned in tandem at the XbaI site in BamHI C fragment (FIG. 22 A and B). This BamHI C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT IBR VIRUS procedure, followed by the BLUOGAL SCREEN FOR RECOMBINANT HERPESVIRUS procedure, and subsequently analyzed for the insertion of the PI-3 HN gene by the SOUTHERN BLOTTING OF DNA procedure. The virus that resulted from this screening was designated S-IBR-018.

The structure of S-IBR-018 is shown in FIG. 22 C.

Example 17

S-IBR-019

S-IBR-019 is an IBR virus that has three foreign genes inserted: the *E. coli* beta-galactosidase (lacZ) gene and the neomycin resistance gene in the XbaI site in the unique long region, and the parainfluenza-3 (PI-3) virus fusion gene (F) in the HindIII site in the long unique region adjacent to the XbaI site.

For cloning the PI-3 F gene, the SF-4 strain of PI-3 was grown in MDBK cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the Sendai virus F gene has been published (27) and this comparative sequence information was used to locate the homologous gene in applicants' bovine PI-3 clones.

The HSV alpha-4 promoter was used to express the PI-3 F gene and the HSV TK poly-A signal was used to terminate transcription. The construct contained (5' to 3') the HSV alpha-4 promoter, the alpha-4 TATA box, the alpha-4 cap site, a fusion in the alpha-4 5' untranslated region to the PI-3 F gene, the F start codon, the F structural gene, the F stop codon, a fusion in the F 3' untranslated region to the HSV TK 3' untranslated region, and the TK poly-A signal sequence.

This plasmid also contained the beta-galactosidase (lacZ) gene under the control of the PRV gpX promoter with the gpX poly-A termination signal, as well as the neomycin resistance gene under the control of the gpX promoter with the TK poly-A termination signal. These latter two genes were cloned in tandem at the XbaI site in BamHI-C fragment (FIG. 23 A and B). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT HERPESVIRUS procedure, followed by the BLUOGAL SCREEN FOR RECOMBINANT HERPESVIRUS procedure, and subsequently analyzed for the insertion of the PI-3 F gene by SOUTHERN BLOTTING OF DNA procedure. The virus that resulted from this screening was designated S-IBR-019.

The structure of S-IBR-019 is shown in FIG. 23 C.

REFERENCES

1. J.L. Cantello et al., Journal of Virology 65, 1584–1588 (1991).
2. U.K. Laemmli, Nature 227, 680–685 (1970).
3. B. Lomniczi et al., Journal of Virology 49, 970–979 (1984).
4. R. Longnecker and B. Roizman, Science 236, 573–576 (1987).
5. S. Mackem and B. Roizman, Proc. Natl. Acad. Sci. USA 79, 4917–4921 (1982).
6. T. Maniatis et al., *Molecular Cloning: A Laboratory Manual*, Cold Spring Harbor Press (1982).
7. J.E. Mayfield et al., Journal of Virology 47, 259–264 (1983).
8. D.J. McGeoch et al., Journal of Molecular Biology 181, 1–13 (1985).
9. D.J. McGeoch et al., Journal of General Virology 68, 19–38 (1987).
10. D.J. McGeoch et al., Journal of General Virology 69, 1531–1574 (1988).
11. E.A. Petrovskis et al., Journal of Virology 60, 116–169 (1986).
12. T.J. Rea et al., Journal of Virology 54, 21–29 (1985).
13. A.K. Robbins et al., Journal of Virology 58,339–347 (1986).
14. J. Sambrook et al., *Molecular Cloning: A Laboratory Manual*, Second Edition, Cold Spring Harbor Press, (1989).
15. G.A. Smith et al., Journal of General Virology 71, 2417–2424 (1990).
16. D.R. Thomsen et al., Gene 16, 207–217, (1981)
17. S.K. Tikoo et al., Journal of Virology 64, 5132–5142 (1990).
18. C.E. Aronson, ed., *Veterinary Pharmaceuticals and Biologicals*, Veterinary Medicine Publ. Co., Lenexa, KS, pp. 138–139 (1982–1983).
19. P.C. Weber et al., Science 236, 576–579 (1987).
20. U.S. Wirth et al., Journal of Virology 65, 195–205 (1991).
21. M. Zijil et al., Journal of Virology 71, 1747–1755 (1990).
22. L. Villarreal and P. Berg, Science 196, 183–185 (1977).
23. U. Gubler and B.J. Hoffman, Gene 25, 263–269 (1983).
24. F.L. Graham and A. Van der Eb, Virology 52, 556–567 (1973).
25. N. Elango et al., Journal of Virology 57, 481–489 (1986).
26. M.K. Spriggs and P.L. Collins, Journal of Virology 59, 646–654 (1986).
27. B.M. Blumberg et al., Journal of General Virology 66, 317–331 (1985).
28. R. W. Price and A. Kahn, Infection and Immunity 34, 571–580 (1981).

29. P. B. Tenser et al., J. of General Virology 64, 1369–1373 (1983).
30. B. Roizman et al., Cold Spring Harbor Conference on New Approaches to Viral Vaccines (September 1983).
31. R. L. Thompson et al., Virology 131, 180–192 (1983).
32. K. Fukuchi et al., Proc. Natl. Acad. Sci. U.S.A. 82, 751–754, 1985.
33. J. M. Koomey et al., J. of Virology 50, 662–665, 1984.
34. S.B. Mohanty and S.K. Dutta, *Veterinary Virology*, Lea and Febiger, Philadelphia (1981).
35. R. Crandell in *Current Veterinary Therapy*, pages 543–546, W.B. Saunders, Philadelphia (1981).
36. H. Ludwig in *The Herpesviruses*, Vol. 2, B. Roizman, ed., Plenum Press (1983).
37. A.J. Davison, EMBO Journal 2, 2203–2209 (1983).
38. F.A. Ferrari et al., J. of Bacteriology 161, 556–562, 1985.
39. V.T. Oi and L.A. Herzenberg, *Selected Methods in Cellular Immunology*, Freeman Publ. Co., San Francisco (1980). pp. 351–372.
40. S. Ihara et al., Virology 122, 268–278 (1982).
41. D. Hanahan, Molecular Biology 166, 557–580 (1983).
42. M.W. Mellencamp et al., J. of Clinical Microbiology 27, 2208–2213 (1989).
43. Kit et al., U.S. Pat. No. 4,824,667, issued Apr. 25, 1989.
44. Kit et al., U.S. Pat. No. 4,703,011, issued Oct. 27, 1987.
45. Kit et al., The Veterinary Record 127, 363–364 (1990).
46. European Patent Publication EP 0 326 127 A2, published Aug. 2, 1989.
47. Federal Register, Vol. 55, No. 90, pp. 19245–19253 (May 9, 1990).
48. Fitzpatrick et al., J. of Virol. 62, 4239–4288 (1988).
49. T. Ben-Porat et al., Virol. 154, 325–334 (1986).
50. F. Zuckerman et al., in *Vaccination and Control of Adjeszky's Disease*, Ed. J. van Oirschot, Kluwer, London (1989). pp. 107–117.
51. L.E. Post et al., J. Reprod. Fert. Suppl. 41, 97–104 (1990).
52. Wirth et al., J. of Virol. 63, 4882–4889 (1989).
53. B. Moss, Science 252, 1662–1667 (1991).
54. R.W. Honess, J. of General Virology 65, 2077–2107 (1984).
55. Cook & Stevens, J. of General Virology 31, 75–80 (1976).
56. Desrosiers et al., Molecular and Cellular Biology 5, 2796–2803 (1985).
57. Thomsen et al., Gene 57, 261–265 (1987).
58. Weir and Narayanan, Nucleic Acids Research 16, 10267–10282 (1988).
59. Spaete and Mocarski, Proceedings of the National Academy of Sciences U.S.A. 84, 7213–7217 (1987).
60. Whealy et al., Journal of Virology 62, 4185–4194 (1988).
61. Shih et al., Procedings of the National Academy of Sciences U.S.A. 81, 5867–5870 (1984).
62. Edwards et al., in *Technological Advances in Vaccine Development*, pp.223–234, Alan Riss Inc. (1988).
63. Proceeding of the 94th Annual Meeting of the United States Animal Health Association, pp. 66–75 (1990).
64. E.A. Petrovskis et al., Journal of Virology 60, 185–193 (1986).
65. Todd et al., U.S. Pat. No. 4,132,775, issued Jan. 2, 1979.

What is claimed is:

1. A vaccine for infectious bovine rhinotracheitis disease which comprises a) an effective immunizing amount of a live recombinant infectious bovine rhinotracheitis virus comprising an infectious bovine rhinotracheitis viral genome from which DNA encoding US2 gene has been deleted and b) a suitable carrier.

2. The vaccine of claim 1 wherein the live recombinant infectious bovine rhinotracheitis virus further comprises a deletion in at least a portion of a repeat region of the infectious bovine rhinotracheitis viral genome.

3. The vaccine of claim 2, wherein the live recombinant infectious bovine rhinotracheitis virus further comprises a 800 base pair deletion in each repeat region and removes the only EcoRV restriction site in each repeat region and a BglII site adjacent to the EcoRV site.

4. A vaccine for infectious bovine rhinotracheitis disease which comprises an effective immunizing amount of a live recombinant infectious bovine rhinotracheitis designated S-IBR-027 (ATCC Accession No. VR 2322) and a suitable carrier.

5. The vaccine of claim 1, wherein the live recombinant infectious bovine rhinotracheitis virus further comprises a deletion in the glycoprotein G (gG) gene of the infectious bovine rhinotracheitis viral genome.

6. A vaccine for infectious bovine rhinotracheitis disease which comprises an effective immunizing amount of a live recombinant infectious bovine rhinotracheitis designated S-IBR-037 (ATCC Accession No. VR 2320) and a suitable carrier.

7. A vaccine for infectious bovine rhinotracheitis disease which comprises an effective immunizing amount of a live recombinant infectious bovine rhinotracheitis virus designated S-IBR-038 and a suitable carrier.

8. The vaccine of claim 1, wherein the live recombinant infectious bovine rhinotracheitis virus further comprises a deletion in the glycoprotein E (gE) gene of the infectious bovine rhinotracheitis viral genome.

9. The vaccine of claim 1, wherein the live recombinant infectious bovine rhinotracheitis virus further comprises an insertion of a foreign DNA sequence within the infectious bovine rhinotracheitis viral genome.

10. The vaccine of claim 9, wherein the live recombinant infectious bovine rhinotracheitis virus further comprises an insertion of the foreign DNA sequence within the US2 gene of the infectious bovine rhinotracheitis viral genome.

11. The vaccine of claim 9, wherein the live recombinant infectious bovine rhinotracheitis virus further comprises an insertion of the foreign DNA sequence within the glycoprotein G (gG) gene of the infectious bovine rhinotracheitis viral genome.

12. The vaccine of claim 9, wherein the live recombinant infectious bovine rhinotracheitis virus further comprises an insertion of the foreign DNA sequence within the glycoprotein E (gE) gene of the infectious bovine rhinotracheitis viral genome.

13. The vaccine of claim 9, wherein the live recombinant infectious bovine rhinotracheitis virus further comprises an insertion of the foreign DNA sequence into the XbaI site in the unique long region of the infectious bovine rhinotracheitis viral genome.

14. The vaccine of claim 9, wherein the foreign DNA sequence encodes a polypeptide.

15. The vaccine of claim 14, wherein the foreign DNA encodes *E.coli* beta-galactosidase.

16. A vaccine for infectious bovine rhinotracheitis disease which comprises an effective immunizing amount of the live recombinant infectious bovine rhinotracheitis virus designated S-IBR-035 and a suitable carrier.

17. A vaccine for infectious bovine rhinotracheitis disease which comprises an effective immunizing amount of the live recombinant infectious bovine rhinotracheitis virus designated S-IBR-036 and a suitable carrier.

18. The vaccine of claim 14, wherein the live recombinant infectious bovine rhinotracheitis virus further comprises a polypeptide which is antigenic in a host infected with the live recombinant virus.

19. The vaccine of claim 1, wherein the suitable carrier is a physiologically balanced culture medium containing stabilizing agents.

20. The vaccine of claim 1, wherein the effective immunizing amount is from about $10^6$ to about $10^9$ PFU/dose.

21. The vaccine of claim 20, wherein the effective immunizing amount is from about $10^7$ to about $10^8$ PFU/dose.

22. A method of immunizing a bovine against a disease caused by an infectious bovine rhinotracheitis virus which comprises administering to the bovine an effective immunizing dose of the vaccine of claim 1.

23. A method of immunizing a bovine against a disease caused by an infectious bovine rhinotracheitis virus which comprises administering to the bovine an effective immunizing dose of the vaccine of claim 4.

24. A method of immunizing a bovine against a disease caused by an infectious bovine rhinotracheitis virus which comprises administering to the bovine an effective immunizing dose of the vaccine of claim 6.

25. A method of immunizing a bovine against a disease caused by an infectious bovine rhinotracheitis virus which comprises administering to the bovine art effective immmunizing dose of the vaccine of claim 7.

26. A method of immunizing a bovine against a disease caused by an infectious bovine rhinotracheitis virus which comprises administering to the bovine an effective immunizing dose of the vaccine of claim 16.

27. The method of claim 22, wherein the vaccine is administered by intramuscular, subcutaneous, intraperitoneal intranasally, orally or intravenous injection.

* * * * *

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 1079 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine Herpesvirus-1 (IBR Virus)
        ( B ) STRAIN: Cooper
        ( C ) INDIVIDUAL ISOLATE: S-IBR- 000

( v i i i ) POSITION IN GENOME:
        ( B ) MAP POSITION: ~86.8 to ~87.8
        ( C ) UNITS: %G ( i x ) FEATURE:
        ( A ) NAME/KEY: CDS
        ( B ) LOCATION: 25..951

( x i ) SEQUENCE DESCRIPTION: SEQ ID NO:1:

```
TTAAGCGTTG CCGTGGCGGT CGCC ATG GTG ACT ATA GTC ACG TGT GGC CGG       51
                         Met Val Thr Ile Val Thr Cys Gly Arg
                          1               5
```

| | | | | | | | | | | | | | | | | |
|---|---|---|---|---|---|---|---|---|---|---|---|---|---|---|---|---|
| ATA | GGC | GCG | GCG | CCT | TCC | AGG | CAA | GCC | CAG | ACG | TGC | GCC | GCG | CGG | GTG | 99 |
| Ile | Gly | Ala | Ala | Pro | Ser | Arg | Gln | Ala | Gln | Thr | Cys | Ala | Ala | Arg | Val | |
| 10 | | | | 15 | | | | | 20 | | | | | | 25 | |
| TGG | CGT | TTC | CTT | GCC | GAG | CAG | AGC | CGG | GCG | CTG | ACG | GCA | AGC | CGG | CTG | 147 |
| Trp | Arg | Phe | Leu | Ala | Glu | Gln | Ser | Arg | Ala | Leu | Thr | Ala | Ser | Arg | Leu | |
| | | | | 30 | | | | | 35 | | | | | 40 | | |
| GGG | ACG | ACG | GTC | GTT | GTC | TTC | GAT | CAC | GCC | CTA | GTA | AAA | ACG | GCG | AAG | 195 |
| Gly | Thr | Thr | Val | Val | Val | Phe | Asp | His | Ala | Leu | Val | Lys | Thr | Ala | Lys | |
| | | | 45 | | | | | 50 | | | | | 55 | | | |
| GGC | TGC | ACG | TCG | ACG | TCA | ACG | TCA | AGC | CAG | CGG | CGC | GGG | TGG | CTT | TTG | 243 |
| Gly | Cys | Thr | Ser | Thr | Ser | Thr | Ser | Ser | Gln | Arg | Arg | Gly | Trp | Leu | Leu | |
| | | 60 | | | | | 65 | | | | | 70 | | | | |
| TCG | ACA | CAG | CGC | CCT | TGG | CCC | GGG | CGC | CGG | CTT | AGC | CCG | CCA | CCG | CCA | 291 |
| Ser | Thr | Gln | Arg | Pro | Trp | Pro | Gly | Arg | Arg | Leu | Ser | Pro | Pro | Pro | Pro | |
| | 75 | | | | | 80 | | | | | 85 | | | | | |
| ACC | GGC | GAG | TGG | GTC | AGC | TGG | TCG | ACG | GCT | ACA | AAC | TTG | CTG | AAA | CTC | 339 |
| Thr | Gly | Glu | Trp | Val | Ser | Trp | Ser | Thr | Ala | Thr | Asn | Leu | Leu | Lys | Leu | |
| 90 | | | | | 95 | | | | 100 | | | | | | 105 | |
| GGC | CGC | GCG | AGG | GCT | CGG | CCC | TTC | CAC | ATG | TGG | GTT | TTT | GGC | GCC | GCC | 387 |
| Gly | Arg | Ala | Arg | Ala | Arg | Pro | Phe | His | Met | Trp | Val | Phe | Gly | Ala | Ala | |
| | | | | 110 | | | | | 115 | | | | | 120 | | |
| GAT | TTG | TAC | GCG | CCT | ATT | TTT | GCG | CAC | ATT | GCC | GCC | ACG | ACG | CGC | TTG | 435 |
| Asp | Leu | Tyr | Ala | Pro | Ile | Phe | Ala | His | Ile | Ala | Ala | Thr | Thr | Arg | Leu | |
| | | | 125 | | | | | 130 | | | | | 135 | | | |
| GTT | TAC | GCG | CAG | CTG | GAC | TGT | ACG | TTT | GCG | GGA | GCG | GCG | TGG | CGG | CTC | 483 |
| Val | Tyr | Ala | Gln | Leu | Asp | Cys | Thr | Phe | Ala | Gly | Ala | Ala | Trp | Arg | Leu | |
| | | 140 | | | | | 145 | | | | | 150 | | | | |
| CCG | CGG | CGC | GGC | CCG | GCC | ATC | GCT | AGC | CCG | TGG | CCG | CCC | TAC | GAT | ACC | 531 |
| Pro | Arg | Arg | Gly | Pro | Ala | Ile | Ala | Ser | Pro | Trp | Pro | Pro | Tyr | Asp | Thr | |
| | 155 | | | | | 160 | | | | | 165 | | | | | |
| CCG | ACA | CTC | CCT | GAG | CTG | GTG | GCC | GGT | GGT | GTC | CTT | TTC | CGG | CTG | GTC | 579 |
| Pro | Thr | Leu | Pro | Glu | Leu | Val | Ala | Gly | Gly | Val | Leu | Phe | Arg | Leu | Val | |
| 170 | | | | | 175 | | | | 180 | | | | | | 185 | |
| TAC | GAA | GTC | GTA | GAC | CGC | GGG | CGG | CGC | CCC | GCC | CCG | CCA | AAC | GCG | AGC | 627 |
| Tyr | Glu | Val | Val | Asp | Arg | Gly | Arg | Arg | Pro | Ala | Pro | Pro | Asn | Ala | Ser | |
| | | | | 190 | | | | | 195 | | | | | 200 | | |
| CCC | CGT | GCC | CCA | GGG | GCT | CGC | CCC | CGC | GCG | CGC | CAT | GTG | CTA | TCC | TTT | 675 |
| Pro | Arg | Ala | Pro | Gly | Ala | Arg | Pro | Arg | Ala | Arg | His | Val | Leu | Ser | Phe | |
| | | 205 | | | | | 210 | | | | | 215 | | | | |
| AAA | GGC | CGC | ACC | CAG | CGC | CGG | CGT | TTG | GTC | ATT | TGC | TTT | GTG | ACC | GCG | 723 |
| Lys | Gly | Arg | Thr | Gln | Arg | Arg | Arg | Leu | Val | Ile | Cys | Phe | Val | Thr | Ala | |
| | | 220 | | | | | 225 | | | | | 230 | | | | |
| CCG | AGG | GAC | CAT | GTT | CCG | CCA | GGG | CAC | CCC | CAA | CCG | CGT | GGT | GAT | CAG | 771 |
| Pro | Arg | Asp | His | Val | Pro | Pro | Gly | His | Pro | Gln | Pro | Arg | Gly | Asp | Gln | |
| | 235 | | | | 240 | | | | | 245 | | | | | | |
| CAC | AGT | GCC | GTT | GAG | CAG | AGA | GGC | GAC | CGC | GAC | CGC | GAC | CGC | CGG | CAC | 819 |
| His | Ser | Ala | Val | Glu | Gln | Arg | Gly | Asp | Arg | Asp | Arg | Asp | Arg | Arg | His | |
| 250 | | | | | 255 | | | | 260 | | | | | | 265 | |
| CGG | TCC | CGG | ATG | CGA | GGG | GGG | GCT | TGG | TGG | CTG | GCG | ACT | CTT | TAC | AGT | 867 |
| Arg | Ser | Arg | Met | Arg | Gly | Gly | Ala | Trp | Trp | Leu | Ala | Thr | Leu | Tyr | Ser | |
| | | | 270 | | | | | 275 | | | | | 280 | | | |
| GCC | GCC | ACG | AGC | AAG | AAG | ACG | GCC | TGT | ATG | CTA | TCG | TCC | GCG | CGG | ACT | 915 |
| Ala | Ala | Thr | Ser | Lys | Lys | Thr | Ala | Cys | Met | Leu | Ser | Ser | Arg | Arg | Thr | |
| | | 285 | | | | | 290 | | | | | 295 | | | | |
| ATT | TTC | CGG | TGG | TGC | CCT | CGT | CCA | AGC | CCC | TGC | TGG | TGAAAGTTCC | | | | 961 |
| Ile | Phe | Arg | Trp | Cys | Pro | Arg | Pro | Ser | Pro | Cys | Trp | | | | | |
| | | 300 | | | | | 305 | | | | | | | | | |

CGCTCCCGGC GCGAGTCCCG ACCGAACTGG GGGCGCAGTT CACTTTGAAT GTGTTCCCGC 1021

GCCGCGCCGA CCGCTGCAGT TCTTTCGTCA GCTTTACGAC GGTTCATTCG TTAAGCTT 1079

( 2 ) INFORMATION FOR SEQ ID NO:2:

( i ) SEQUENCE CHARACTERISTICS:
       ( A ) LENGTH: 18 amino acids
       ( B ) TYPE: amino acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:2:

His Met Trp Val Phe Gly Ala Ala Asp Leu Tyr Ala Pro Ile Phe Ala
   1               5                   10                  15

His Ile ( 2 ) INFORMATION FOR SEQ ID NO:3:

( i ) SEQUENCE CHARACTERISTICS:
       ( A ) LENGTH: 18 amino acids
       ( B ) TYPE: amino acid
       ( C ) STRANDEDNESS: double
       ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
       ( A ) ORGANISM: Herpes Simplex Virus Type 1

( x i ) SEQUENCE DESCRIPTION: SEQ ID NO:3:

His Leu Trp Val Val Gly Ala Ala Asp Leu Cys Val Pro Phe Leu Glu
1               5                   10                  15

Tyr Ala ( 2 ) INFORMATION FOR SEQ ID NO:4:

( i ) SEQUENCE CHARACTERISTICS:
       ( A ) LENGTH: 18 amino acids
       ( B ) TYPE: amino acid
       ( C ) STRANDEDNESS: double
       ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
       ( A ) ORGANISM: Pseudorabies Virus ( x i ) SEQUENCE DESCRIPTION: SEQ ID NO:4:

His Leu Trp Ile Leu Gly Ala Ala Asp Leu Cys Asp Gln Val Leu Leu
1               5                   10                  15

Ala Ala ( 2 ) INFORMATION FOR SEQ ID NO:5:

( i ) SEQUENCE CHARACTERISTICS:
       ( A ) LENGTH: 18 amino acids
       ( B ) TYPE: amino acid
       ( C ) STRANDEDNESS: double
       ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Herpes Simplex Virus Type 2

( x i ) SEQUENCE DESCRIPTION: SEQ ID NO:5:

| His | Leu | Trp | Val | Val | Gly | Ala | Ala | Asp | Leu | Cys | Val | Pro | Phe | Phe | Glu |
|---|---|---|---|---|---|---|---|---|---|---|---|---|---|---|---|
| 1 | | | | 5 | | | | | 10 | | | | | 15 | |

| Tyr | Ala |
|---|---|

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Marek's Disease Virus ( x i ) SEQUENCE DESCRIPTION: SEQ ID NO:6:

| His | Ser | Leu | Trp | Ile | Val | Gly | Ala | Ala | Asp | Ile | Cys | Arg | Ile | Ala | Leu |
|---|---|---|---|---|---|---|---|---|---|---|---|---|---|---|---|
| 1 | | | | 5 | | | | | 10 | | | | | 15 | |

| Glu | Cys | Ile |
|---|---|---|

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TGAGCGCGCG CCGCTGCATG CTGGTGCGAA CTCACGCCGA GCGCGCGTGC GAGCAAGCTT    60

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

CTAGTAAAAA CGGCGAAGGG CTGGTGCGAA CTCACGCCGA GCGCGCGTGC GAGCAAGCTT    60

( 2 ) INFORMATION FOR SEQ ID NO:9:

( i ) SEQUENCE CHARACTERISTICS:

( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

CTAGTAAAAA CGGCGAAGGG CTGCACGTCG ACGTCAACGT CAAGCCAGCG GCGCGGGTGG        60

( 2 ) INFORMATION FOR SEQ ID NO:10:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

GATTTAGGTG ACACTATAGA ATACACGGAA TTCGAGCTCG CCCCATGG        48

( 2 ) INFORMATION FOR SEQ ID NO:11:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..12

( x i ) SEQUENCE DESCRIPTION: SEQ ID NO:11:

TTA AGT GGG ATC CCGGCGCGCA GGCGCGCACG TCGGTCGCGG TCGCGCGCCA        52
Leu Ser Gly Ile
 1

TGGGGGATCC TCTAGAGCTT GGGCTGCAGG TCCTGATTGA TACACTG        99

( 2 ) INFORMATION FOR SEQ ID NO:12:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

GCCCCGATCG TCCACACGGA GCGCGGCTGC CGACACGGAT CTGATCAAGA GACAGGATGA        60

```
GGATCGTTTC GC ATG ATT GAA CAA GAT GGA TTG CAC GCA                                    99
           Met Ile Glu Gln Asp Gly Leu His Ala
           1               5
```

( 2 ) INFORMATION FOR SEQ ID NO:13:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 64..78

( x i ) SEQUENCE DESCRIPTION: SEQ ID NO:13:

```
GGACCTTGCA CAGATAGCGT GGTCCGGCCA GGACGACGAG GCTTGCAGGA TCCTCTAGAG        60

TCG GGA GAT GGG GGA GGC TAACTGAAAC ACGGAAGGAG A                          99
    Gly Asp Gly Gly Gly
    1               5
```

( 2 ) INFORMATION FOR SEQ ID NO:14:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 61..99

( x i ) SEQUENCE DESCRIPTION: SEQ ID NO:14:

```
GTGTTGCTGC GTTCCCGACC TGCAGCCCAA GCTCTAGAGT CGACCTGCAG CCCAAGCTCA        60

GAT CTG CTC ATG CTC GCG GCC GCC ATG CCC CCG GAA GCG                      99
Asp Leu Leu Met Leu Ala Ala Ala Met Pro Pro Glu Ala
1               5               10
```

( 2 ) INFORMATION FOR SEQ ID NO:15:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

```
AGGCAGATCT GAGCTTGGCG TAATCATGGT CATAGCTGTT TCCTGTGTGA AATTGTTATC        60
```

( 2 ) INFORMATION FOR SEQ ID NO:16:

( i ) SEQUENCE CHARACTERISTICS:
    ( A ) LENGTH: 1386 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Bovine herpesvirus-1 (IBR virus)
    ( B ) STRAIN: Cooper
    ( C ) INDIVIDUAL ISOLATE: S-IBR- 000

( v i i ) IMMEDIATE SOURCE:
    ( B ) CLONE: 439-18.1 (PSY 1643)

( v i i i ) POSITION IN GENOME:
    ( B ) MAP POSITION: −86.8 to 87.8
    ( C ) UNITS: %G ( i x ) FEATURE:
    ( A ) NAME/KEY: CDS
    ( B ) LOCATION: 7..1329

( x i ) SEQUENCE DESCRIPTION: SEQ ID NO:16:

```
GCGATC ATG CCT GCC GCC CGG ACC GGC ACC TTG GCC GCC GTC GCC CTA         48
       Met Pro Ala Ala Arg Thr Gly Thr Leu Ala Ala Val Ala Leu
        1           5                  10

ATC CTG CTC TGC GGG GCC GCC GTT TTG CGG CCC CGC GCC CGA CGA CCT        96
Ile Leu Leu Cys Gly Ala Ala Val Leu Arg Pro Arg Ala Arg Arg Pro
 15              20                  25                  30

CTG TTT CGC CGA CGT GCG CCG CAC TGG CAT GGC GCC CTC CCG CCC GCT       144
Leu Phe Arg Arg Arg Ala Pro His Trp His Gly Ala Leu Pro Pro Ala
                 35                  40                  45

GGG GCC CGT CCT GAA CCT AGC GGC CTC GGA TTT GAC CTC GCG GGT TTC       192
Gly Ala Arg Pro Glu Pro Ser Gly Leu Gly Phe Asp Leu Ala Gly Phe
             50                  55                  60

GGT GCG CGC GGT GGA GCT TCG CGC GCT GCG CCC TGG CCC TCT TGG ACA       240
Gly Ala Arg Gly Gly Ala Ser Arg Ala Ala Pro Trp Pro Ser Trp Thr
         65                  70                  75

TGG CGG AGA CGG TGG TGC CCG GCG GAC CGC GAG CCS CAC GTC GTC GAC       288
Trp Arg Arg Arg Trp Cys Pro Ala Asp Arg Glu Pro His Val Val Asp
     80                  85                  90

GTC GGC TGG GCT TAC CAA GAC GGG GAC TGC ATG GTG CCT CTG GCA TAT       336
Val Gly Trp Ala Tyr Gln Asp Gly Asp Cys Met Val Pro Leu Ala Tyr
 95                 100                 105                 110

CGC CAG TAC TTT AAC TGC ACG GGG GCG CTG CCC GGC CAA AAC GTC           384
Arg Gln Tyr Phe Asn Cys Thr Gly Gly Ala Leu Pro Gly Gln Asn Val
                115                 120                 125

TGC GCC GGG CTC TCT GAG ACC CGC ATC CGC GGT GGC TTT GGA ACC TCC       432
Cys Ala Gly Leu Ser Glu Thr Arg Ile Arg Gly Gly Phe Gly Thr Ser
            130                 135                 140

GAC TAC GCG CTC TAC GGG ACG TCG CTA GTA CTG CGC CCC GGC CTG TAC       480
Asp Tyr Ala Leu Tyr Gly Thr Ser Leu Val Leu Arg Pro Gly Leu Tyr
        145                 150                 155

GAC CGC GGG ACC TAC ATC TAC TTC CTT GGA TAC GGC CCA GAC GAC ATC       528
Asp Arg Gly Thr Tyr Ile Tyr Phe Leu Gly Tyr Gly Pro Asp Asp Ile
    160                 165                 170

TAC GTG GGC AGC GTC ACG CTC ATG GTG GGC GCC GAC ATC CAC AAA TAC       576
Tyr Val Gly Ser Val Thr Leu Met Val Gly Ala Asp Ile His Lys Tyr
175                 180                 185                 190

CCC TGC GGG CTG GAC CGA GGG CTC GGT GTG GCC CTG CAC CAC AAG AGC       624
Pro Cys Gly Leu Asp Arg Gly Leu Gly Val Ala Leu His His Lys Ser
```

|                                                                                                              |      |
|--------------------------------------------------------------------------------------------------------------|------|
| GGA CCG GCC CGA CCT CTG ACA GAG GAC GAC GCC ACC GGC GAC TGG GCC<br>Gly Pro Ala Arg Pro Leu Thr Glu Asp Asp Ala Thr Gly Asp Trp Ala<br>        210                     215                     220 | 672  |
| TGC GGC TGC TTC CCC GCC CTT GTT GAG GTT GAC GCG GTG TGG GGC AAC<br>Cys Gly Cys Phe Pro Ala Leu Val Glu Val Asp Ala Val Trp Gly Asn<br>    225                     230                     235     | 720  |
| GTA AGC GCC GCA GAG CTG GGC CTG GCC GAC CCG ATC GAC TAC GCC GAC<br>Val Ser Ala Ala Glu Leu Gly Leu Ala Asp Pro Ile Asp Tyr Ala Asp<br>240                     245                     250         | 768  |
| GAA GGG GGT GAG GTC GAA GTG CTC GAG GAC GAA GCC GGG AGC GCC AGC<br>Glu Gly Gly Glu Val Glu Val Leu Glu Asp Glu Ala Gly Ser Ala Ser<br>255                     260                     265                     270 | 816 |
| GGA AAC CTG CCG CAG GAC GAC CCC GAC CCC GAC CTC GCA GAT TGC CGG<br>Gly Asn Leu Pro Gln Asp Asp Pro Asp Pro Asp Leu Ala Asp Cys Arg<br>                    275                     280                     285 | 864 |
| ACC GTC GGG CTC TTT AGC GAA AGC GAC ATG TTC CGG ACC GCC AGC GGG<br>Thr Val Gly Leu Phe Ser Glu Ser Asp Met Phe Arg Thr Ala Ser Gly<br>                290                     295                     300 | 912 |
| CCC GAA TCG CTG CTG ATC GGC GCC GTT GCC AAG GAC GTC CTG ACG GTG<br>Pro Glu Ser Leu Leu Ile Gly Ala Val Ala Lys Asp Val Leu Thr Val<br>        305                     310                     315 | 960 |
| CCC CTC AAT CTG CCG CCC GGC CGC TCT TAC GAG GCC CTG CGA AAC GCA<br>Pro Leu Asn Leu Pro Pro Gly Arg Ser Tyr Glu Ala Leu Arg Asn Ala<br>320                     325                     330         | 1008 |
| TCG CTG GAG TGC AAC TCC CGC CCG CGC GAG ACC GGC GAC GCA GCG GTG<br>Ser Leu Glu Cys Asn Ser Arg Pro Arg Glu Thr Gly Asp Ala Ala Val<br>335                     340                     345                     350 | 1056 |
| GTG GTG ATG TCT CTC CAG GAG CCC GCT CGC CTC GAG CGC CGC CCC GAT<br>Val Val Met Ser Leu Gln Glu Pro Ala Arg Leu Glu Arg Arg Pro Asp<br>                355                     360                     365 | 1104 |
| GCC CGC GCC ACC GAT CCG GAG TTT GGG CTC TTT GGC CTG CCC GAT GAC<br>Ala Arg Ala Thr Asp Pro Glu Phe Gly Leu Phe Gly Leu Pro Asp Asp<br>        370                     375                     380 | 1152 |
| CCC GCC GTG CGC GCG GCA TTC TCA TCG GCC TCG CGA TCG CTC TGC TGG<br>Pro Ala Val Arg Ala Ala Phe Ser Ser Ala Ser Arg Ser Leu Cys Trp<br>            385                     390                     395 | 1200 |
| TGC TGC TGT TTC GCT GGT GAT CGT GCT CGT CTG CGC CTG CCG GCT CGC<br>Cys Cys Cys Phe Ala Gly Asp Arg Ala Arg Leu Arg Leu Pro Ala Arg<br>    400                     405                     410     | 1248 |
| CCG CCC AGC CAA GGC TGC GCG ACG CCC CGC GCC GCC ACG TTC GCC AAG<br>Pro Pro Ser Gln Gly Cys Ala Thr Pro Arg Ala Ala Thr Phe Ala Lys<br>415                     420                     425                     430 | 1296 |
| AGC AAC CCC GCG TAC GAG CCG ATG CTC AGC GTC TGATCGCCGG CACCCCACGC<br>Ser Asn Pro Ala Tyr Glu Pro Met Leu Ser Val<br>                435                     440 | 1349 |
| CGCCCGACC CCGCTGTCCC GCGTTTACAA TAAACAG                                                                      | 1386 |

( 2 ) INFORMATION FOR SEQ ID NO:17:

( i ) SEQUENCE CHARACTERISTICS:
        ( A ) LENGTH: 34 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

(A) ORGANISM: Bovine Herpesvirus-1 (IBR Virus)

(x i) SEQUENCE DESCRIPTION: SEQ ID NO:17:

| Val | Gly | Tr ( i v ) ANTI-SENSE: NO ( x i ) SEQUENCE DESCRIPTION: SEQ ID NO:20:

CACATACGAT TTAGGTGACA CTATAGAATA CAAGCTTGGG CTGCAGGTCG ACTCTAGAGT 60

CGACCTGCAG TGAATAATAA AATGTGTGTT TGTCCGAAAT AC 102

( 2 ) INFORMATION FOR SEQ ID NO:21:

( i ) SEQUENCE CHARACTERISTICS:
( A ) LENGTH: 102 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

GCGTTTGAGA TTTCTGTCCC GACTAAATTC ATGTCGCGCG ATAGTGGTGT TTATCGCCGA 60

TAGAGATGGC GATATTGGAA AAATCGATAT TTGAAAATAT GG 102

( 2 ) INFORMATION FOR SEQ ID NO:22:

( i ) SEQUENCE CHARACTERISTICS:
( A ) LENGTH: 102 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

CATATTGAAA ATGTCGCCGA TGTGAGTTTC TGTGTAACTG ATCGCGTGTT TGGAGGCAAC 60

CGGGGCCTGC TCCCGACGGC CAGCGACGAC GTGGTGCTCA AG 102

( 2 ) INFORMATION FOR SEQ ID NO:23:

( i ) SEQUENCE CHARACTERISTICS:
( A ) LENGTH: 102 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 1..102

( x i ) SEQUENCE DESCRIPTION: SEQ ID NO:23:

ATG TCT CTC CAG GAG CCC GCT CGC CTC GAG GGC CTG CCC TCG CAG CTG 48
Met Ser Leu Gln Glu Pro Ala Arg Leu Glu Gly Leu Pro Ser Gln Leu
1               5                   10                  15

CCC GTC TTC GAG GAC ACG CAG CGC TAC GAC GCC TCC CCC GCG TCC GTG 96
Pro Val Phe Glu Asp Thr Gln Arg Tyr Asp Ala Ser Pro Ala Ser Val
            20                  25                  30

```
AGC TGG                                                                                                  102
Ser Trp
```

( 2 ) INFORMATION FOR SEQ ID NO:24:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..42

( i x ) FEATURE:
        ( A ) NAME/KEY: CDS
        ( B ) LOCATION: 43..63

( i x ) FEATURE:
        ( A ) NAME/KEY: CDS
        ( B ) LOCATION: 64..102

( x i ) SEQUENCE DESCRIPTION: SEQ ID NO:24:

```
CCC GTG AGC AGC ATG ATC GTC GTC ATC GCC GGC ATC GGG ATC CTG GCC           48
Pro Val Ser Ser Met Ile Val Val Ile Ala Gly Ile Gly Ile Leu Ala
 1               5                  10                       1

ATC GTG CTG GTC ATC CAT ATG GCG ATC ATC AGG GCC CGG GCC CGG AAC           96
Ile Val Leu Val Ile His Met Ala Ile Ile Arg Ala Arg Ala Arg Asn
         5               1              5                  10

GAC GGC                                                                  102
Asp Gly
```

( 2 ) INFORMATION FOR SEQ ID NO:25:

( i ) SEQUENCE CHARACTERISTICS:
        ( A ) LENGTH: 75 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

```
GGGCCAGTAC CGGCGCCTGG TGTCCGTCGA CTCTAGAGTC GACCTGCAGC CCAAGCTTTG         60

GCGTAATCAT GGTCA                                                          75
```

( 2 ) INFORMATION FOR SEQ ID NO:26:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

ACATACGATT TAGGTGACAC TATAGAATAC AAGCTTAACG AATGAACCGT CGTAAAG    57

( 2 ) INFORMATION FOR SEQ ID NO:27:

( i ) SEQUENCE CHARACTERISTICS:
        ( A ) LENGTH: 96 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..12

( x i ) SEQUENCE DESCRIPTION: SEQ ID NO:27:

GTC GAA GTG CTC GAAATTCGAG CTCGCCCGGG GATCCTCTAG AGTCGACCTG    52
Val Glu Val Leu
 1

CAGGTCGACT CTAGAGGATC TCGACGGACA CCAGGCGCCG GTAC    96

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

Val Glu Val Leu
 1

( 2 ) INFORMATION FOR SEQ ID NO:29:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:29:

GGGCGGGGCC GGGTCAGCCG GATCTAGAGT CCCAGGACCC AACGCTGCCC GAGTTTG    57

( 2 ) INFORMATION FOR SEQ ID NO:30:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

TCCCAGTCAC GACGTTGTAA AACGACGGGA TCCATGGTCC CGGTGTCTTC TATGGAG 57

( 2 ) INFORMATION FOR SEQ ID NO:31:

( i ) SEQUENCE CHARACTERISTICS:
            ( A ) LENGTH: 57 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: CDS
            ( B ) LOCATION: 49..57

( x i ) SEQUENCE DESCRIPTION: SEQ ID NO:31:

ATTCACTGCA GGTCGACTCT AGAGGATCCC CGGGCGAGCT CGAATTTC GAG CGC CGC 57
                                                                           Glu Arg Arg
                                                                            1

( 2 ) INFORMATION FOR SEQ ID NO:32:

( i ) SEQUENCE CHARACTERISTICS:
            ( A ) LENGTH: 57 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: CDS
            ( B ) LOCATION: 1..27

( x i ) SEQUENCE DESCRIPTION: SEQ ID NO:32:

GCG CGC GCG TAC AAC GCC ACG GTC ATA GGGCGAGCTC GAATTCGTAA 47
Ala Arg Ala Tyr Asn Ala Thr Val Ile
 1                    5

TCATGGTCAT 57

( 2 ) INFORMATION FOR SEQ ID NO:33:

( i ) SEQUENCE CHARACTERISTICS:
            ( A ) LENGTH: 57 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:33:

ATACACATAC GATTTAGGTG ACACTATAGA ATACAAGCTC GCGTGTTTGG AGGCAAC 57

( 2 ) INFORMATION FOR SEQ ID NO:34:

( i ) SEQUENCE CHARACTERISTICS:
            ( A ) LENGTH: 102 base pairs
            ( B ) TYPE: nucleic acid (C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

TCGGGGTAGC CCCAATTCGA GCTCGCCCGG GGATCCTCTA GAGTCGACCT GCAGGTCGAC    60

TCTAGAGGAT CTCGACGGAC ACCAGGCGCC GGTACTGGCC CT    102

(2) INFORMATION FOR SEQ ID NO:35:

(i) SEQUENCE CHARACTERISTICS:
      (A) LENGTH: 84 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 67..84

(xi) SEQUENCE DESCRIPTION: SEQ ID NO:35:

CGGGGTAGCC CCAATTCGAG CTCGCCCGGG GATCCTCTAG AGGATCCCCG GGCGAGCTCG    60

AATTTC GAG CGC CGC CCC GAT GCC    84
      Glu Arg Arg Pro Asp Ala
       1           5

(2) INFORMATION FOR SEQ ID NO:36:

(i) SEQUENCE CHARACTERISTICS:
      (A) LENGTH: 2040 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Bovine herpesvirus-1 (IBR virus)
      (B) STRAIN: Cooper
      (C) INDIVIDUAL ISOLATE: S-IBR- 000

(vii) IMMEDIATE SOURCE:
      (B) CLONE:PSY 1644, PSY 1645

(viii) POSITION IN GENOME:
      (B) MAP POSITION: −86.8 to 87.8
      (C) UNITS: %G (ix) FEATURE:
      (A) NAME/KEY: CDS
      (B) LOCATION: 85..1935

(xi) SEQUENCE DESCRIPTION: SEQ ID NO:36:

GCGGGCAAGG CGGAGGAAGA CCGGGGGCAG GAGCTGCGTG GAGGGCGGAG CCGTTGAGCG    60

GCCCGACCGC CGCCGGGTTG TTAA ATG GGT CTC GCG CGG CTC GTG GTT CCA    111
                                     Met Gly Leu Ala Arg Leu Val Val Pro
                                     1            5

| | | | | | | | | | | | | | | | | |
|---|---|---|---|---|---|---|---|---|---|---|---|---|---|---|---|---|
| CAC | CGC | GCC | GGA | GAA | CCA | GCG | CGC | AGC | TTC | GCT | GCG | TGT | GTC | CCG | CGA | 159 |
| His | Arg | Ala | Gly | Glu | Pro | Ala | Arg | Ser | Phe | Ala | Ala | Cys | Val | Pro | Arg | |
| 10 | | | | 15 | | | | | 20 | | | | | | 25 | |
| GCT | GCG | TTC | CGG | GGA | ACG | GCG | CGC | GCG | AGA | GGG | TTC | GAA | AAG | GGC | ATT | 207 |
| Ala | Ala | Phe | Arg | Gly | Thr | Ala | Arg | Ala | Arg | Gly | Phe | Glu | Lys | Gly | Ile | |
| | | | | 30 | | | | | 35 | | | | | 40 | | |
| TGG | CAA | TGC | AAC | CCA | CCG | CGC | CGC | CCC | GGC | SSG | GTT | GCG | CCG | CTG | CTG | 255 |
| Trp | Gln | Cys | Asn | Pro | Pro | Arg | Arg | Pro | Gly | Xxx | Val | Ala | Pro | Leu | Leu | |
| | | | 45 | | | | | 50 | | | | | 55 | | | |
| CTG | CCG | CAG | TTA | TTG | CTT | TTC | GGG | CTG | ATG | GCC | GAG | GCC | AAG | CCC | GCG | 303 |
| Leu | Pro | Gln | Leu | Leu | Leu | Phe | Gly | Leu | Met | Ala | Glu | Ala | Lys | Pro | Ala | |
| | | 60 | | | | | 65 | | | | 70 | | | | | |
| ACC | GAA | ACC | CCG | GGC | TCG | GCT | TCG | GTC | GAC | ACG | GTC | TTC | ACG | GCG | CGC | 351 |
| Thr | Glu | Thr | Pro | Gly | Ser | Ala | Ser | Val | Asp | Thr | Val | Phe | Thr | Ala | Arg | |
| | 75 | | | | | 80 | | | | | 85 | | | | | |
| GCT | GGC | GCG | CCC | GTC | TTT | CTC | CCA | GGG | CCC | GCG | GCG | CGC | CCG | GAC | GTG | 399 |
| Ala | Gly | Ala | Pro | Val | Phe | Leu | Pro | Gly | Pro | Ala | Ala | Arg | Pro | Asp | Val | |
| 90 | | | | | 95 | | | | 100 | | | | | | 105 | |
| CGC | GCC | GTT | CGC | GGC | TGG | AGC | GTC | CTC | GCG | GCC | GCC | TGC | TCG | CCG | CCC | 447 |
| Arg | Ala | Val | Arg | Gly | Trp | Ser | Val | Leu | Ala | Ala | Ala | Cys | Ser | Pro | Pro | |
| | | | | 110 | | | | | 115 | | | | | 120 | | |
| GTG | CCG | GAG | CCC | GTC | TGC | CTC | GAC | GAC | CGC | GAG | TGC | TTC | ACC | GAC | GTG | 495 |
| Val | Pro | Glu | Pro | Val | Cys | Leu | Asp | Asp | Arg | Glu | Cys | Phe | Thr | Asp | Val | |
| | | | 125 | | | | | 130 | | | | | 135 | | | |
| GCC | CTG | GAC | GCG | GCC | TGC | CTG | CGA | ACC | GCC | CGC | GTG | GCC | CCG | CTG | GCC | 543 |
| Ala | Leu | Asp | Ala | Ala | Cys | Leu | Arg | Thr | Ala | Arg | Val | Ala | Pro | Leu | Ala | |
| | | 140 | | | | | 145 | | | | | 150 | | | | |
| ATC | GCG | GAG | CTC | GCC | GAG | CGG | CCC | GAC | TCA | ACG | GGC | GAC | AAA | GAG | TTT | 591 |
| Ile | Ala | Glu | Leu | Ala | Glu | Arg | Pro | Asp | Ser | Thr | Gly | Asp | Lys | Glu | Phe | |
| 155 | | | | | | 160 | | | | | 165 | | | | | |
| GTT | CTC | GCC | GAC | CCG | CAC | GTC | TCG | GCG | CAG | CTG | GGT | CGC | AAC | GCG | ACC | 639 |
| Val | Leu | Ala | Asp | Pro | His | Val | Ser | Ala | Gln | Leu | Gly | Arg | Asn | Ala | Thr | |
| 170 | | | | | 175 | | | | | 180 | | | | | 185 | |
| GGG | GTG | CTG | ATC | GCG | GCC | GCA | GCC | GAG | GAG | GAC | GGC | GGC | GTG | TAC | TTC | 687 |
| Gly | Val | Leu | Ile | Ala | Ala | Ala | Ala | Glu | Glu | Asp | Gly | Gly | Val | Tyr | Phe | |
| | | | | 190 | | | | | 195 | | | | | 200 | | |
| CTG | TAC | GAC | CGG | CTC | ATC | GGC | GAC | GCC | GGC | GAC | GAG | GAG | ACG | CAG | TTG | 735 |
| Leu | Tyr | Asp | Arg | Leu | Ile | Gly | Asp | Ala | Gly | Asp | Glu | Glu | Thr | Gln | Leu | |
| | | | 205 | | | | | 210 | | | | | 215 | | | |
| GCG | CTG | ACG | CTG | CAG | GTC | GCG | ACG | GCC | GGC | GCG | CAG | GGC | GCC | GCG | CGG | 783 |
| Ala | Leu | Thr | Leu | Gln | Val | Ala | Thr | Ala | Gly | Ala | Gln | Gly | Ala | Ala | Arg | |
| | | 220 | | | | | 225 | | | | | 230 | | | | |
| GAC | GAG | GAG | AGG | GAA | CCA | GCG | ACC | GGG | CCC | ACC | CCC | GGC | CCG | CCG | CCC | 831 |
| Asp | Glu | Glu | Arg | Glu | Pro | Ala | Thr | Gly | Pro | Thr | Pro | Gly | Pro | Pro | Pro | |
| | | 235 | | | | | 240 | | | | | 245 | | | | |
| CAC | CGC | ACG | ACG | ACA | CGC | GCG | CCC | CCG | CGG | CGG | CAC | GGC | GCG | CGC | TTC | 879 |
| His | Arg | Thr | Thr | Thr | Arg | Ala | Pro | Pro | Arg | Arg | His | Gly | Ala | Arg | Phe | |
| 250 | | | | | 255 | | | | | 260 | | | | | 265 | |
| CGC | GTG | CTG | CCG | TAC | CAC | TCC | CAC | GTA | TAC | ACC | CCG | GGC | GAT | TCC | TTT | 927 |
| Arg | Val | Leu | Pro | Tyr | His | Ser | His | Val | Tyr | Thr | Pro | Gly | Asp | Ser | Phe | |
| | | | | 270 | | | | | 275 | | | | | 280 | | |
| CTG | CTA | TCG | GTG | CGT | CTG | CAG | TCT | GAG | TTT | TTC | GAC | GAG | GCT | CCC | TTC | 975 |
| Leu | Leu | Ser | Val | Arg | Leu | Gln | Ser | Glu | Phe | Phe | Asp | Glu | Ala | Pro | Phe | |
| | | | 285 | | | | | 290 | | | | | 295 | | | |
| TCG | GCC | AGC | ATC | GAC | TGG | TAC | TTC | CTG | CGG | ACG | GCC | GGC | GAC | TGC | GCG | 1023 |
| Ser | Ala | Ser | Ile | Asp | Trp | Tyr | Phe | Leu | Arg | Thr | Ala | Gly | Asp | Cys | Ala | |
| | | | 300 | | | | | 305 | | | | | 310 | | | |
| CTC | ATC | CGC | ATA | TAC | GAG | ACG | TGC | ATC | TTC | CAC | CCC | GAG | GCA | CCG | GCC | 1071 |
| Leu | Ile | Arg | Ile | Tyr | Glu | Thr | Cys | Ile | Phe | His | Pro | Glu | Ala | Pro | Ala | |
| | | | 315 | | | | 320 | | | | | 325 | | | | |

| | | | | | | | | | | | | | | | | |
|---|---|---|---|---|---|---|---|---|---|---|---|---|---|---|---|---|
| TGC | CTG | CAC | CCC | GCC | GAC | GCG | CAG | TGC | AGC | TTC | GCG | TCG | CCG | TAC | CGC | 1119 |
| Cys 330 | Leu | His | Pro | Ala | Asp 335 | Ala | Gln | Cys | Ser | Phe 340 | Ala | Ser | Pro | Tyr | Arg 345 | |
| TCC | GAG | ACC | GTG | TAC | AGC | CGG | CTG | TAC | GAG | CAG | TGC | CGC | CCG | GAC | CCT | 1167 |
| Ser | Glu | Thr | Val | Tyr 350 | Ser | Arg | Leu | Tyr | Glu 355 | Gln | Cys | Arg | Pro | Asp 360 | Pro | |
| GCC | GGT | CGC | TGG | CCG | CAC | GAG | TGC | GAG | GGC | GCC | GCG | TAC | GCG | GCG | CCC | 1215 |
| Ala | Gly | Arg | Trp 365 | Pro | His | Glu | Cys | Glu 370 | Gly | Ala | Ala | Tyr | Ala 375 | Ala | Pro | |
| GTT | GCG | CAC | CTG | CGT | CCC | GCC | AAT | AAC | AGC | GTA | GAC | CTG | GTC | TTT | GAC | 1263 |
| Val | Ala | His 380 | Leu | Arg | Pro | Ala | Asn | Asn 385 | Ser | Val | Asp | Leu 390 | Val | Phe | Asp | |
| GAC | GCG | CCG | GCT | GCG | GCC | TCC | GGG | CTT | TAC | GTC | TTT | GTG | CTG | CAG | TAC | 1311 |
| Asp | Ala 395 | Pro | Ala | Ala | Ala | Ser 400 | Gly | Leu | Tyr | Val | Phe 405 | Val | Leu | Gln | Tyr | |
| AAC | GGC | CAC | GTG | GAA | GCT | TGG | GAC | TAC | TGC | CTA | GTC | GTT | ACT | TCG | GAC | 1359 |
| Asn 410 | Gly | His | Val | Glu | Ala 415 | Trp | Asp | Tyr | Cys | Leu 420 | Val | Val | Thr | Ser | Asp 425 | |
| CGT | TTG | GTG | CGC | GCG | GTC | ACC | GAC | CAC | ACG | CGC | CCC | GAG | GCC | GCA | GCC | 1407 |
| Arg | Leu | Val | Arg | Ala 430 | Val | Thr | Asp | His | Thr 435 | Arg | Pro | Glu | Ala | Ala 440 | Ala | |
| GCC | GAC | GCT | CCC | GAG | CCA | GGC | CCA | CCG | CTC | ACC | AGC | GAG | CCG | GCG | GGG | 1455 |
| Ala | Asp | Ala | Pro 445 | Glu | Pro | Gly | Pro | Pro 450 | Leu | Thr | Ser | Glu | Pro 455 | Ala | Gly | |
| GSG | CCC | ACC | GGG | CCC | GCG | CCC | TGG | CTT | GTG | GTG | CTG | GTG | GGC | GCG | CTT | 1503 |
| Xxx | Pro | Thr 460 | Gly | Pro | Ala | Pro | Trp 465 | Leu | Val | Val | Leu | Val 470 | Gly | Ala | Leu | |
| GGA | CTC | GCG | GGA | CTG | GTG | GGC | ATC | GCA | GCC | CTC | GCC | GTT | CGG | GTG | TGC | 1551 |
| Gly | Leu 475 | Ala | Gly | Leu | Val | Gly 480 | Ile | Ala | Ala | Leu | Ala 485 | Val | Arg | Val | Cys | |
| GCG | CGC | CGC | GCA | AGC | CAG | AAG | CGC | ACC | TAC | GAC | ATC | CTC | AAC | CCC | TTC | 1599 |
| Ala 490 | Arg | Arg | Ala | Ser | Gln 495 | Lys | Arg | Thr | Tyr | Asp 500 | Ile | Leu | Asn | Pro | Phe 505 | |
| GGG | CCC | GTA | TAC | ACC | AGC | TTG | CCG | ACC | AAC | GAG | CCG | CTC | GAC | GTG | GTG | 1647 |
| Gly | Pro | Val | Tyr | Thr 510 | Ser | Leu | Pro | Thr | Asn 515 | Glu | Pro | Leu | Asp | Val 520 | Val | |
| GTG | CCA | GTT | AGC | GAC | GAC | GAA | TTT | TCC | CTC | GAC | GAA | GAC | TCT | TTT | GCG | 1695 |
| Val | Pro | Val | Ser 525 | Asp | Asp | Glu | Phe | Ser 530 | Leu | Asp | Glu | Asp | Ser 535 | Phe | Ala | |
| GAT | GAC | GAC | AGC | GAC | GAT | GAC | GGG | CCC | GCT | AGC | AAC | CCC | CCT | GCG | GAT | 1743 |
| Asp | Asp | Asp 540 | Ser | Asp | Asp | Asp | Gly 545 | Pro | Ala | Ser | Asn | Pro 550 | Pro | Ala | Asp | |
| GCC | TAC | GAC | CTC | GCC | GGC | GCC | CCA | GAG | CCA | ACT | AGC | GGG | TTT | GCG | CGA | 1791 |
| Ala | Tyr 555 | Asp | Leu | Ala | Gly | Ala 560 | Pro | Glu | Pro | Thr | Ser 565 | Gly | Phe | Ala | Arg | |
| GCC | CCC | GCC | AAC | GGC | ACG | CGC | TCG | AGT | CGC | TCT | GGG | TTC | AAA | GTT | TGG | 1839 |
| Ala 570 | Pro | Ala | Asn | Gly | Thr 575 | Arg | Ser | Ser | Arg | Ser 580 | Gly | Phe | Lys | Val | Trp 585 | |
| TTT | AGG | GAC | CCG | CTT | GAA | GAC | GAT | GCC | GCG | CCA | GCG | CGG | ACC | CCG | GCC | 1887 |
| Phe | Arg | Asp | Pro | Leu 590 | Glu | Asp | Asp | Ala | Ala 595 | Pro | Ala | Arg | Thr | Pro 600 | Ala | |
| GCA | CCA | GAT | TAC | ACC | GTG | GTA | GCA | GCG | CGA | CTC | AAG | TCC | ATC | CTC | CGC | 1935 |
| Ala | Pro | Asp | Tyr 605 | Thr | Val | Val | Ala | Ala 610 | Arg | Leu | Lys | Ser | Ile 615 | Leu | Arg | |

TAGGCGCCCC CCCCCGCGCG CTGTGCCGTC TGACGGAAAG CACCCGCGTG TAGGGCTGCA 1995

TATAAATGGA GCGCTCACAC AAAGCCTCGT GCGGCTGCTT CGAAG 2040

( 2 ) INFORMATION FOR SEQ ID NO:37:

( i ) SEQUENCE CHARACTERISTICS:
    ( A ) LENGTH: 50 amino acids
    ( B ) TYPE: amino acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Herpes Simplex Virus Type 1

( x i ) SEQUENCE DESCRIPTION: SEQ ID NO:37:

```
Trp Leu Arg Phe Asp Val Pro Thr Ser Cys Ala Glu Met Arg Ile Tyr
 1               5                  10                  15

Glu Ser Cys Leu Tyr His Pro Gln Leu Pro Glu Cys Leu Ser Pro Ala
                20                  25                  30

Asp Ala Pro Cys Ala Ala Ser Thr Trp Thr Ser Arg Leu Ala Val Arg
             35                  40                  45

Ser Tyr
     50
```

( 2 ) INFORMATION FOR SEQ ID NO:38:

( i ) SEQUENCE CHARACTERISTICS:
        ( A ) LENGTH: 52 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Pseudorabies Virus ( x i ) SEQUENCE DESCRIPTION: SEQ ID NO:38:

```
Trp Tyr Tyr Ala Arg Ala Pro Pro Arg Cys Leu Leu Tyr Tyr Val Tyr
 1               5                  10                  15

Glu Pro Cys Ile Tyr His Pro Arg Ala Pro Glu Cys Leu Arg Pro Val
                20                  25                  30

Asp Pro Ala Cys Ser Phe Thr Ser Pro Ala Arg Ala Ala Leu Val Ala
             35                  40                  45

Arg Arg Ala Tyr
         50
```

( 2 ) INFORMATION FOR SEQ ID NO:39:

( i ) SEQUENCE CHARACTERISTICS:
        ( A ) LENGTH: 52 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Varicella-Zoster Virus ( x i ) SEQUENCE DESCRIPTION: SEQ ID NO:39:

```
Trp  Leu  Tyr  Val  Pro  Ile  Asp  Pro  Thr  Cys  Gln  Pro  Met  Arg  Leu  Tyr
1              5                        10                       15

Ser  Thr  Cys  Leu  Tyr  His  Pro  Asn  Ala  Pro  Gln  Cys  Leu  Ser  His  Met
               20                       25                       30

Asn  Ser  Gly  Cys  Thr  Phe  Thr  Ser  Pro  His  Leu  Ala  Gln  Arg  Val  Ala
          35                       40                       45

Ser  Thr  Val  Tyr
          50
```

( 2 ) INFORMATION FOR SEQ ID NO:40:

( i ) SEQUENCE CHARACTERISTICS:
        ( A ) LENGTH: 52 amino acids
        ( B ) TYPE: amino acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bovine Herpesvirus-1 (IBR Virus)

( x i ) SEQUENCE DESCRIPTION: SEQ ID NO:40:

```
Trp Tyr Phe Leu Arg Thr Ala Gly Asp Cys Ala Leu Ile Arg Ile Tyr
1               5                   10                  15

Glu Thr Cys Ile Phe His Pro Glu Ala Pro Ala Cys Leu His Pro Ala
            20                  25                  30

Asp Ala Gln Cys Ser Phe Ala Ser Pro Tyr Arg Ser Glu Thr Val Tyr
        35                  40                  45

Ser Arg Leu Tyr
    50
```

( 2 ) INFORMATION FOR SEQ ID NO:41:

( i ) SEQUENCE CHARACTERISTICS:
( A ) LENGTH: 84 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION: 34..84

( x i ) SEQUENCE DESCRIPTION: SEQ ID NO:41:

```
TTGGGCTGCA GGTCGACTCT AGAGGATCCC CTA TGG TAC AAG ATC GAG AGC GGG     54
                                     Trp Tyr Lys Ile Glu Ser Gly
                                     1               5

TGC GCC CGG CCG CTG TAC TAC ATG GAG TAC                              84
Cys Ala Arg Pro Leu Tyr Tyr Met Glu Tyr
        10                  15
```

( 2 ) INFORMATION FOR SEQ ID NO:42:

( i ) SEQUENCE CHARACTERISTICS:
( A ) LENGTH: 84 base pairs
( B ) TYPE: nucleic acid (C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1..84

(xi) SEQUENCE DESCRIPTION: SEQ ID NO:42:

| TCC | GGG | CTT | TAC | GTC | TTT | GTG | CTG | CAG | TAC | AAC | GGC | CAC | GTG | GAA | GCT | 48 |
| Ser | Gly | Leu | Tyr | Val | Phe | Val | Leu | Gln | Tyr | Asn | Gly | His | Val | Glu | Ala | |
| 1 | | | | 5 | | | | | 10 | | | | | 15 | | |

| TGG | GAC | TAC | AGC | CTA | GTC | GTT | ACT | TCG | GAC | CGT | TTG | 84 |
| Trp | Asp | Tyr | Ser | Leu | Val | Val | Thr | Ser | Asp | Arg | Leu | |
| | | | 20 | | | | | 25 | | | | |

(2) INFORMATION FOR SEQ ID NO:43:

(i) SEQUENCE CHARACTERISTICS:
(A) LENGTH: 84 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

CCTTCACCGC CGCCGGAAGG CTCCATCGTG TCCATCCCCA TCCTCGAGCT CGAATTGGGG    60

ATCCTCTAGA GTCGACCTGC AGCC    84

(2) INFORMATION FOR SEQ ID NO:44:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 28..33

(xi) SEQUENCE DESCRIPTION: SEQ ID NO:44:

CTATAGAATA CACGGAATTC GAGCTCG CCC GGG TGAGCGGCCT AGGCCCTCCC    53
                              Pro Gly
                               1

CCGACCG    60

(2) INFORMATION FOR SEQ ID NO:45:

(i) SEQUENCE CHARACTERISTICS:
(A) LENGTH: 90 base pairs
(B) TYPE: nucleic acid
(C) STRANDEDNESS: double
(D) TOPOLOGY: linear ( i i ) MOLECULE TYPE: DNA (genomic)

( i i i ) HYPOTHETICAL: NO ( i v ) ANTI-SENSE: NO ( i x ) FEATURE:
                      ( A ) NAME/KEY: CDS
                      ( B ) LOCATION: 1..33

( x i ) SEQUENCE DESCRIPTION: SEQ ID NO:45:

```
ATG  GCC  GAG  GCC  AAG  CCC  GCG  ACC  GAA  ACC  CCG  GGGATCCTCT  AGAGTCGACG      53
Met  Ala  Glu  Ala  Lys  Pro  Ala  Thr  Glu  Thr  Pro
 1             5                       10

TCTGGGGCGC  GGGGGTGGTG  CTCTTCGAGA  CGCTGCC                                         90
```

( 2 ) INFORMATION FOR SEQ ID NO:46:

( i ) SEQUENCE CHARACTERISTICS:
                      ( A ) LENGTH: 90 base pairs
                      ( B ) TYPE: nucleic acid
                      ( C ) STRANDEDNESS: double
                      ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                      ( A ) NAME/KEY: CDS
                      ( B ) LOCATION: 28..48

( i x ) FEATURE:
                      ( A ) NAME/KEY: CDS
                      ( B ) LOCATION: 49..90

( x i ) SEQUENCE DESCRIPTION: SEQ ID NO:46:

```
ACCTTTGCGC  ATCTCCACAG  CTCAACA  ATG  AAG  TGG  GCA  ACG  TGG  ATC  GAT            51
                                Met  Lys  Trp  Ala  Thr  Trp  Ile  Asp
                                 1              5                   1

CCC  GTC  GTT  TTA  CAA  CGT  CGT  GAC  TGG  GAA  AAC  CCT  GGC                    90
Pro  Val  Val  Leu  Gln  Arg  Arg  Asp  Trp  Glu  Asn  Pro  Gly
               5                        10
```

( 2 ) INFORMATION FOR SEQ ID NO:47:

( i ) SEQUENCE CHARACTERISTICS:
                      ( A ) LENGTH: 216 base pairs
                      ( B ) TYPE: nucleic acid
                      ( C ) STRANDEDNESS: double
                      ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
                      ( A ) NAME/KEY: CDS
                      ( B ) LOCATION: 1..84

( i x ) FEATURE:
                      ( A ) NAME/KEY: CDS
                      ( B ) LOCATION: 134..190

( x i ) SEQUENCE DESCRIPTION: SEQ ID NO:47:

```
TGG  AGC  CCG  TCA  GTA  TCG  GCG  GAA  ATC  CAG  CTG  AGC  GCC  GGT  CGC  TAC     48
Trp  Ser  Pro  Ser  Val  Ser  Ala  Glu  Ile  Gln  Leu  Ser  Ala  Gly  Arg  Tyr
 1              5                        10                       15
```

```
CAT  TAC  CAG  TTG  GTC  TGG  TGT  CAA  AAA  GAT  CTA  GAA  TAAGCTAGAG           94
His  Tyr  Gln  Leu  Val  Trp  Cys  Gln  Lys  Asp  Leu  Glu
               20                        25

GATCGATCCC  CTATGGCGAT  CATCAGGGCC  CGATCCCCT  ATG  GCG  ATC  ATC  AGG          148
                                                Met  Ala  Ile  Ile  Arg
                                                 1                   5

GCC  CGG  GCC  CGG  AAC  GAC  GGC  TAC  CGC  CAC  GTG  GCC  TCC  GCC            190
Ala  Arg  Ala  Arg  Asn  Asp  Gly  Tyr  Arg  His  Val  Ala  Ser  Ala
                    10                        15

TGACCCGGCC  CCGCCGACT  CCCCCG                                                    216
```

( 2 ) INFORMATION FOR SEQ ID NO:48:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 49..90

( x i ) SEQUENCE DESCRIPTION: SEQ ID NO:48:

```
GGCGCCTGGT  GTCCGTCGAC  TCTAGAGTCG  ACCTGCAGCC  CAAGCTCT  AGC  AAC  CCC          57
                                                          Ser  Asn  Pro
                                                                     1

CCT  GCG  GAT  GCC  TAC  GAC  CTC  GCC  GGC  GCC  CCA                            90
Pro  Ala  Asp  Ala  Tyr  Asp  Leu  Ala  Gly  Ala  Pro
          5                        10
```

( 2 ) INFORMATION FOR SEQ ID NO:49:

( i ) SEQUENCE CHARACTERISTICS:
        ( A ) LENGTH: 1880 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Parainfluenza-3 virus ( i x ) FEATURE:
        ( A ) NAME/KEY: CDS
        ( B ) LOCATION: 73..1788

( x i ) SEQUENCE DESCRIPTION: SEQ ID NO:49:

```
AGGAACAAAG  TTGTTCAACA  CAGCAGCAGC  GAACAGACCC  AAAGGCAGCG  CAGAGGCGAC           60

ACCGAACCCA  AA  ATG  GAA  TAT  TGG  AAA  CAC  ACA  AAC  AGC  ACA  AAA  AAC     108
                Met  Glu  Tyr  Trp  Lys  His  Thr  Asn  Ser  Thr  Lys  Asn
                 1             5                           10

ACC  AAC  AAT  GAA  ACC  GAA  ACA  ACC  AGA  GGC  AAA  CAC  AGT  AGC  AAG  GTT  156
Thr  Asn  Asn  Glu  Thr  Glu  Thr  Thr  Arg  Gly  Lys  His  Ser  Ser  Lys  Val
               15                       20                       25

ACA  AAT  ATC  ATA  ATG  TAC  ACC  TTC  TGG  ACA  ATA  ACA  TCA  ACA  ATA  TTA  204
Thr  Asn  Ile  Ile  Met  Tyr  Thr  Phe  Trp  Thr  Ile  Thr  Ser  Thr  Ile  Leu
          30                       35                       40
```

```
TTA  GTC  ATT  TTT  ATA  ATG  ATA  TTG  ACA  AAC  TTA  ATT  CAA  GAG  AAC  AAT        252
Leu  Val  Ile  Phe  Ile  Met  Ile  Leu  Thr  Asn  Leu  Ile  Gln  Glu  Asn  Asn
 45                 50                           55                           60

CAT  AAT  AAA  TTA  ATG  TTG  CAG  GAA  ATA  AGA  AAA  GAA  TTC  GCG  GCA  ATA        300
His  Asn  Lys  Leu  Met  Leu  Gln  Glu  Ile  Arg  Lys  Glu  Phe  Ala  Ala  Ile
                         65                      70                       75

GAC  ACC  AAG  ATT  CAG  AGG  ACC  TCG  GAT  GAC  ATT  GGA  ACC  TCA  ATA  CAG        348
Asp  Thr  Lys  Ile  Gln  Arg  Thr  Ser  Asp  Asp  Ile  Gly  Thr  Ser  Ile  Gln
               80                           85                      90

TCA  GGA  ATA  AAT  ACA  AGA  CTT  CTC  ACA  ATT  CAG  AGT  CAT  GTT  CAA  AAC        396
Ser  Gly  Ile  Asn  Thr  Arg  Leu  Leu  Thr  Ile  Gln  Ser  His  Val  Gln  Asn
               95                      100                     105

TAT  ATC  CCA  CTA  TCA  CTA  ACA  CAA  CAA  ATG  TCA  GAT  CTC  AGA  AAA  TTT        444
Tyr  Ile  Pro  Leu  Ser  Leu  Thr  Gln  Gln  Met  Ser  Asp  Leu  Arg  Lys  Phe
     110                      115                     120

ATC  AAT  GAT  CTA  ACA  AAT  AAA  AGA  GAA  CAT  CAA  GAA  GTG  CCA  ATA  CAG        492
Ile  Asn  Asp  Leu  Thr  Asn  Lys  Arg  Glu  His  Gln  Glu  Val  Pro  Ile  Gln
125                      130                     135                          140

AGA  ATG  ACT  CAT  GAT  AGA  GGT  ATA  GAA  CCC  CTA  AAT  CCA  GAC  AAG  TTC        540
Arg  Met  Thr  His  Asp  Arg  Gly  Ile  Glu  Pro  Leu  Asn  Pro  Asp  Lys  Phe
                    145                      150                     155

TGG  AGG  TGT  ACA  TCT  GGT  AAC  CCA  TCT  CTA  ACA  AGT  AGT  CCT  AAG  ATA        588
Trp  Arg  Cys  Thr  Ser  Gly  Asn  Pro  Ser  Leu  Thr  Ser  Ser  Pro  Lys  Ile
               160                      165                     170

AGG  TTA  ATA  CCA  GGG  CCA  GGT  TTA  TTA  GCA  ACA  TCT  ACT  ACA  GTA  AAT        636
Arg  Leu  Ile  Pro  Gly  Pro  Gly  Leu  Leu  Ala  Thr  Ser  Thr  Thr  Val  Asn
          175                      180                     185

GGC  TGT  ATT  AGA  ATC  CCA  TCG  TTA  GCA  ATC  AAT  CAT  TTA  ATC  TAC  GCT        684
Gly  Cys  Ile  Arg  Ile  Pro  Ser  Leu  Ala  Ile  Asn  His  Leu  Ile  Tyr  Ala
     190                      195                     200

TAC  ACC  TCT  AAT  CTT  ATC  ACC  CAG  GGC  TGT  CAA  AAT  ATA  GGG  AAA  TCT        732
Tyr  Thr  Ser  Asn  Leu  Ile  Thr  Gln  Gly  Cys  Gln  Asn  Ile  Gly  Lys  Ser
205                      210                     215                          220

TAC  CAA  GTA  CTA  CAA  ATA  GGG  ATA  ATT  ACT  ATA  AAT  TCG  GAC  CTA  GTA        780
Tyr  Gln  Val  Leu  Gln  Ile  Gly  Ile  Ile  Thr  Ile  Asn  Ser  Asp  Leu  Val
                    225                      230                     235

CCT  GAT  TTA  AAT  CCC  AGA  GTC  ACA  CAT  ACA  TTT  AAT  ATT  GAT  GAT  AAT        828
Pro  Asp  Leu  Asn  Pro  Arg  Val  Thr  His  Thr  Phe  Asn  Ile  Asp  Asp  Asn
               240                      245                     250

AGG  AAA  TCT  TGC  TCT  CTG  GCA  CTA  TTG  AAT  ACA  GAT  GTT  TAT  CAG  TTA        876
Arg  Lys  Ser  Cys  Ser  Leu  Ala  Leu  Leu  Asn  Thr  Asp  Val  Tyr  Gln  Leu
          255                      260                     265

TGC  TCA  ACA  CCA  AAA  GTT  GAT  GAG  AGA  TCC  GAT  TAT  GCA  TCA  ACA  GGT        924
Cys  Ser  Thr  Pro  Lys  Val  Asp  Glu  Arg  Ser  Asp  Tyr  Ala  Ser  Thr  Gly
     270                      275                     280

ATT  GAG  GAT  ATT  GTA  CTT  GAC  ATT  GTC  ACT  AAT  AAT  GGA  TTA  ATT  ATA        972
Ile  Glu  Asp  Ile  Val  Leu  Asp  Ile  Val  Thr  Asn  Asn  Gly  Leu  Ile  Ile
285                      290                     295                          300

ACA  ACA  AGG  TTT  ACA  AAT  AAT  AAT  ATA  ACT  TTT  GAT  AAA  CCG  TAT  GCA       1020
Thr  Thr  Arg  Phe  Thr  Asn  Asn  Asn  Ile  Thr  Phe  Asp  Lys  Pro  Tyr  Ala
                    305                      310                     315

GCA  TTG  TAT  CCA  TCA  GTA  GGA  CCA  GGA  ATC  TAT  TAT  AAG  GGT  AAA  GTT       1068
Ala  Leu  Tyr  Pro  Ser  Val  Gly  Pro  Gly  Ile  Tyr  Tyr  Lys  Gly  Lys  Val
               320                      325                     330

ATC  TTT  CTC  GGA  TAT  GGA  GGT  CTA  GAG  CAT  GAA  GAA  AAC  GGA  GAC  GTA       1116
Ile  Phe  Leu  Gly  Tyr  Gly  Gly  Leu  Glu  His  Glu  Glu  Asn  Gly  Asp  Val
          335                      340                     345

ATA  TGT  AAT  ACA  ACT  GGT  TGT  CCT  GGC  AAA  ACA  CAG  AGA  GAC  TGT  AAT       1164
Ile  Cys  Asn  Thr  Thr  Gly  Cys  Pro  Gly  Lys  Thr  Gln  Arg  Asp  Cys  Asn
     350                      355                     360
```

| | | | | | | | | | | | | | | | | |
|---|---|---|---|---|---|---|---|---|---|---|---|---|---|---|---|---|
| CAG | GCT | TCT | TAT | AGC | CCA | TGG | TTC | TCA | AAT | AGG | AGA | ATG | GTA | AAC | TCT | 1212 |
| Gln | Ala | Ser | Tyr | Ser | Pro | Trp | Phe | Ser | Asn | Arg | Arg | Met | Val | Asn | Ser | |
| 365 | | | | 370 | | | | | 375 | | | | | | 380 | |
| ATT | ATT | GTT | GTT | GAT | AAA | GGC | ATA | GAT | GCA | ACT | TTT | AGC | TTG | AGG | GTG | 1260 |
| Ile | Ile | Val | Val | Asp | Lys | Gly | Ile | Asp | Ala | Thr | Phe | Ser | Leu | Arg | Val | |
| | | | | 385 | | | | | 390 | | | | | 395 | | |
| TGG | ACT | ATT | CCA | ATG | AGC | CAA | AAT | TAT | TGG | GGA | TCA | GAA | GGA | AGA | TTA | 1308 |
| Trp | Thr | Ile | Pro | Met | Ser | Gln | Asn | Tyr | Trp | Gly | Ser | Glu | Gly | Arg | Leu | |
| | | | 400 | | | | | 405 | | | | | 410 | | | |
| CTT | TTA | TTA | GGT | GAC | AGA | ATA | TAC | ATA | TAT | ACT | AGA | TCC | ACA | AGT | TGG | 1356 |
| Leu | Leu | Leu | Gly | Asp | Arg | Ile | Tyr | Ile | Tyr | Thr | Arg | Ser | Thr | Ser | Trp | |
| | | 415 | | | | | 420 | | | | | 425 | | | | |
| CAC | AGT | AAA | TTA | CAG | TTA | GGG | GTA | ATT | GAT | ATT | TCT | GAT | TAT | AAT | AAT | 1404 |
| His | Ser | Lys | Leu | Gln | Leu | Gly | Val | Ile | Asp | Ile | Ser | Asp | Tyr | Asn | Asn | |
| | 430 | | | | | 435 | | | | | 440 | | | | | |
| ATA | AGA | ATA | AAT | TGG | ACT | TGG | CAT | AAT | GTA | CCA | TCA | CGG | CCA | GGA | AAT | 1452 |
| Ile | Arg | Ile | Asn | Trp | Thr | Trp | His | Asn | Val | Pro | Ser | Arg | Pro | Gly | Asn | |
| 445 | | | | | 450 | | | | | 455 | | | | | 460 | |
| GAT | GAA | TGT | CCA | TGG | GGT | CAT | TCA | TGC | CCA | GAC | GGA | TGT | ATA | ACA | GGA | 1500 |
| Asp | Glu | Cys | Pro | Trp | Gly | His | Ser | Cys | Pro | Asp | Gly | Cys | Ile | Thr | Gly | |
| | | | | 465 | | | | | 470 | | | | | 475 | | |
| GTT | TAC | ACT | GAT | GCA | TAT | CCG | CTA | AAC | CCA | TCG | GGG | AGT | GTT | GTA | TCA | 1548 |
| Val | Tyr | Thr | Asp | Ala | Tyr | Pro | Leu | Asn | Pro | Ser | Gly | Ser | Val | Val | Ser | |
| | | | 480 | | | | | 485 | | | | | 490 | | | |
| TCA | GTA | ATT | CTT | GAC | TCA | CAA | AAG | TCT | AGA | GAA | AAC | CCA | ATC | ATT | ACC | 1596 |
| Ser | Val | Ile | Leu | Asp | Ser | Gln | Lys | Ser | Arg | Glu | Asn | Pro | Ile | Ile | Thr | |
| | | 495 | | | | | 500 | | | | | 505 | | | | |
| TAC | TCA | ACA | GCT | ACA | AAT | AGA | ATA | AAT | GAA | TTA | GCT | ATA | TAT | AAC | AGA | 1644 |
| Tyr | Ser | Thr | Ala | Thr | Asn | Arg | Ile | Asn | Glu | Leu | Ala | Ile | Tyr | Asn | Arg | |
| | 510 | | | | | 515 | | | | | 520 | | | | | |
| ACA | CTT | CCA | GCT | GCA | TAT | ACA | ACA | ACA | AAT | TGT | ATC | ACA | CAT | TAT | GAT | 1692 |
| Thr | Leu | Pro | Ala | Ala | Tyr | Thr | Thr | Thr | Asn | Cys | Ile | Thr | His | Tyr | Asp | |
| 525 | | | | | 530 | | | | | 535 | | | | | 540 | |
| AAA | GGG | TAT | TGT | TTT | CAT | ATA | GTA | GAA | ATA | AAT | CAC | AGA | AGT | TTG | AAT | 1740 |
| Lys | Gly | Tyr | Cys | Phe | His | Ile | Val | Glu | Ile | Asn | His | Arg | Ser | Leu | Asn | |
| | | | | 545 | | | | | 550 | | | | | 555 | | |
| ACG | TTT | CAA | CCT | ATG | TTA | TTC | AAA | ACA | GAA | GTT | CCA | AAA | AAC | TGC | AGC | 1788 |
| Thr | Phe | Gln | Pro | Met | Leu | Phe | Lys | Thr | Glu | Val | Pro | Lys | Asn | Cys | Ser | |
| | | | 560 | | | | | 565 | | | | | 570 | | | |

TAAATGATCA TCGCATATCG GATGCCAGAT GACATTAAAA GAGACCACCA GACAGACAAC    1848

ACAGGAGATG ATGCAAGATA TAAAGGAATA AT    1880

( 2 ) INFORMATION FOR SEQ ID NO:50:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:50:

GGGAATTCTG CAGGTCACAT CATACAATTC TAATCTAAG    39

( 2 ) INFORMATION FOR SEQ ID NO:51:

( i ) SEQUENCE CHARACTERISTICS:

-continued ( A ) LENGTH: 43 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:51:

GGGAATTCTG CAGGCTTTAA AAGAGAGAAT TTCCGTTTGG CTA 43